(12) United States Patent
Lawu

(10) Patent No.: US 10,799,338 B2
(45) Date of Patent: Oct. 13, 2020

(54) WIDE DEPTH OF FOCUS VORTEX INTRAOCULAR LENSES AND ASSOCIATED METHODS

(71) Applicant: Hoya Corporation, Tokyo (JP)

(72) Inventor: Tjundewo Lawu, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 15/449,893

(22) Filed: Mar. 3, 2017

(65) Prior Publication Data

US 2017/0196682 A1 Jul. 13, 2017

Related U.S. Application Data

(63) Continuation-in-part of application No. PCT/IB2015/056780, filed on Sep. 4, 2015.

(60) Provisional application No. 62/046,530, filed on Sep. 5, 2014.

(51) Int. Cl.
*A61F 2/16* (2006.01)
*G02C 7/04* (2006.01)

(52) U.S. Cl.
CPC ............ *A61F 2/164* (2015.04); *A61F 2/1618* (2013.01); *A61F 2/1637* (2013.01); *G02C 7/045* (2013.01); *A61F 2002/1681* (2013.01); *A61F 2002/1696* (2015.04); *A61F 2240/004* (2013.01); *A61F 2250/0053* (2013.01); *G02C 7/042* (2013.01)

(58) Field of Classification Search
None
See application file for complete search history.

(56) References Cited

U.S. PATENT DOCUMENTS

| | | | |
|---|---|---|---|
| 4,504,982 A | 3/1985 | Burk | |
| 2003/0117577 A1* | 6/2003 | Jones | G02C 7/042 351/159.41 |
| 2006/0176572 A1* | 8/2006 | Fiala | A61F 2/16 359/643 |
| 2009/0210054 A1* | 8/2009 | Weeber | A61F 2/1613 623/6.11 |
| 2014/0293426 A1 | 10/2014 | Dobschal et al. | |

FOREIGN PATENT DOCUMENTS

| | | |
|---|---|---|
| EP | 622653 A1 | 11/1994 |
| WO | WO 2009017403 A1 | 2/2009 |
| WO | WO 2012156081 A1 | 11/2012 |
| WO | WO 2015022216 A1 | 2/2015 |

OTHER PUBLICATIONS

International Application No. PCT/IB2015/056780: International Search Report, dated Mar. 10, 2016.
International Application No. PCT/IB2015/056780: Written Opinion of the International Search Authority, dated Mar. 10, 2016.

* cited by examiner

*Primary Examiner* — David H Willse
*Assistant Examiner* — Javier G Blanco
(74) *Attorney, Agent, or Firm* — Henricks Slavin LLP

(57) ABSTRACT

A wide range depth of focus vortex IOL or other optical device or element and processes for manufacturing same.

18 Claims, 41 Drawing Sheets

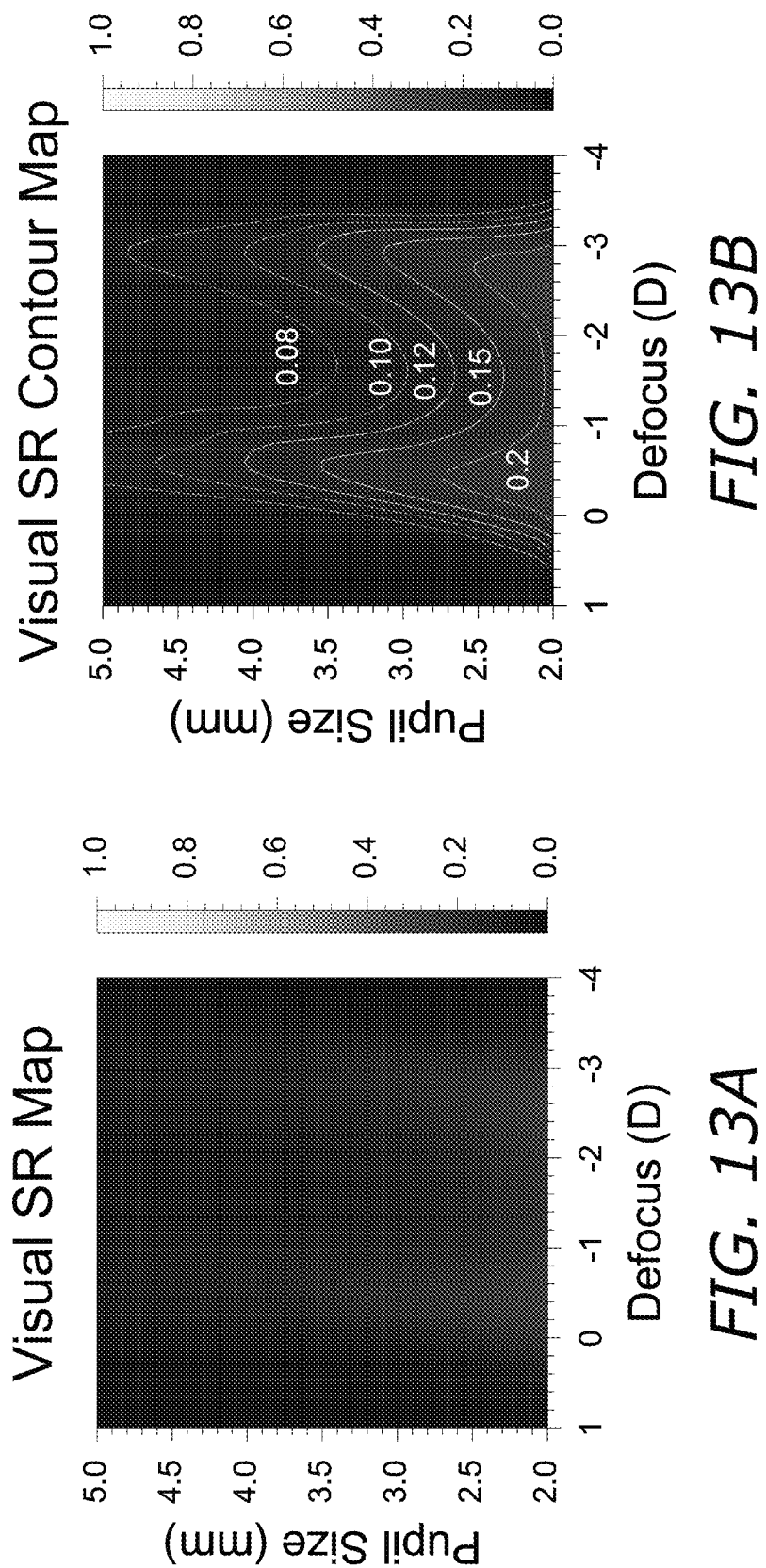

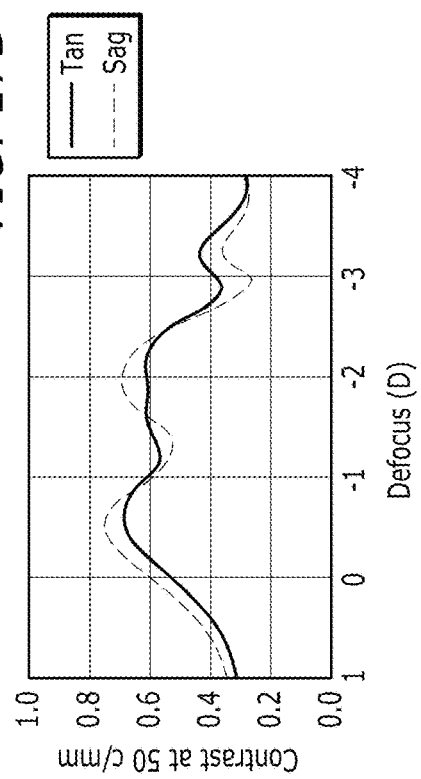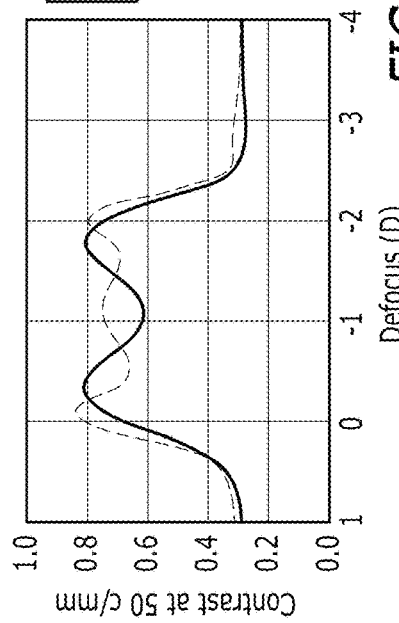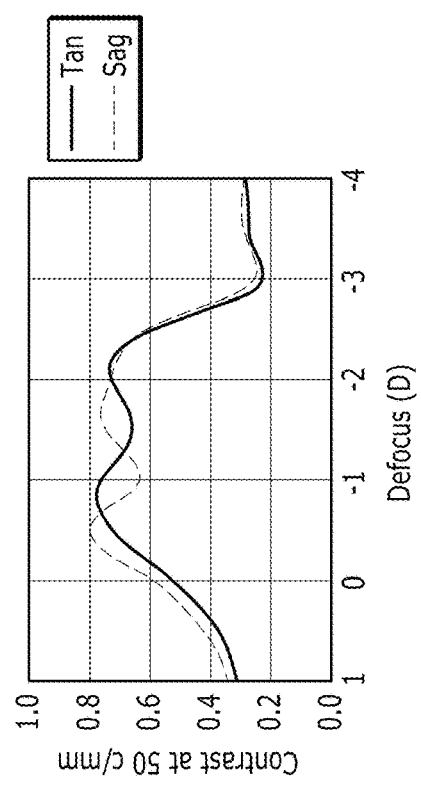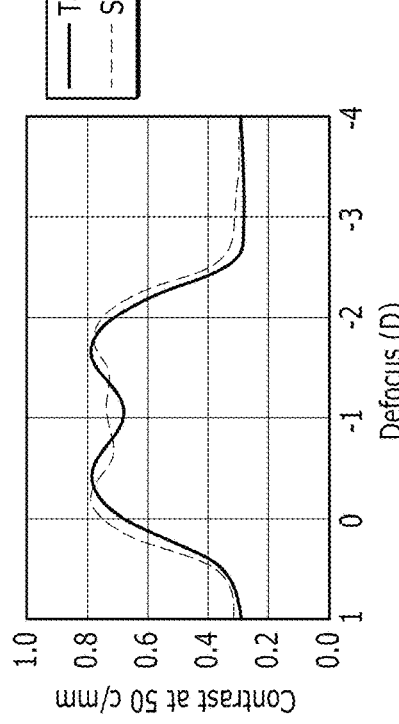
FIG. 17A  FIG. 17B
FIG. 18A  FIG. 18B

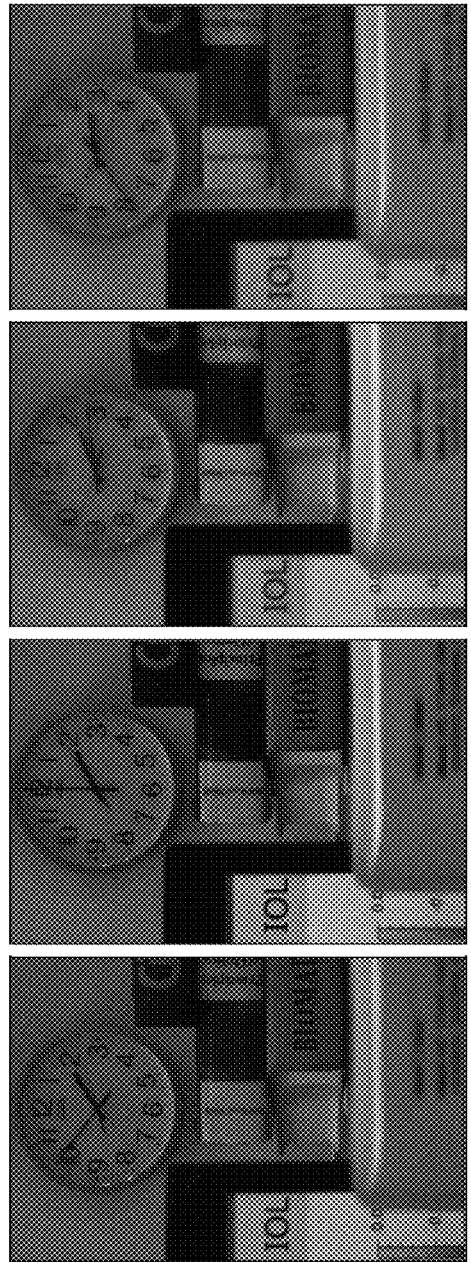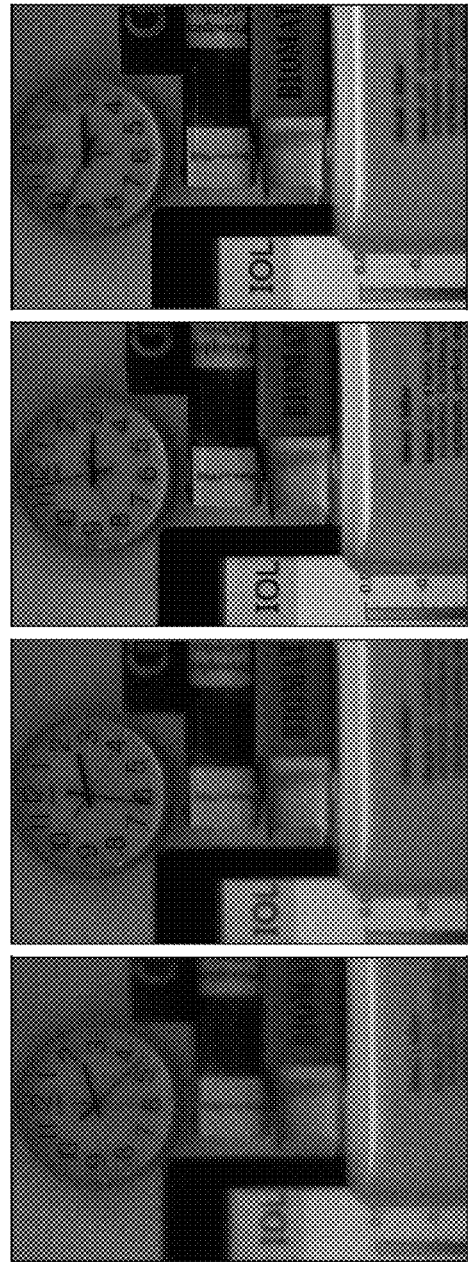
FIG. 39

WIDE DEPTH OF FOCUS VORTEX INTRAOCULAR LENSES AND ASSOCIATED METHODS

CROSS-REFERENCE TO RELATED APPLICATIONS

This is a continuation-in-part of International Application PCT/IB2015/056780, with an international filing date of Sep. 4, 2015, which claims the priority of U.S. provisional Application No. 62/046,530, entitled "Wide Depth of Focus Vortex Intraocular Lenses and Associated Methods" filed on Sep. 5, 2014, the full disclosures of which are incorporated herein by reference.

TECHNICAL FIELD

The present inventions (or invention) relate(s) generally to optical devices or elements such as intraocular lenses and processes for manufacturing same.

BACKGROUND ART

The visual impairment caused by cataract can lead to a significant reduction in patients' quality of life. Driving, reading, or performing other daily-life activities that depend on visual performance can become extremely difficult for these patients. D. Espindle, B. Crawford, A. Maxwell, K. Rajagopalan, R. Barnes, B. Harris, and K. Hileman, "Quality-of-life improvements in cataract patients with bilateral blue light-filtering intraocular lenses: Clinical trial," *J. Cataract Refract. Surg.*, 31, 1952-1959 (2005).

The use of intraocular lenses (IOLs) is a common option to restore the refractive power of the eye in aphakic patients after cataract surgery. A monofocal with spherical design is the mainstream of the current optical designs for an IOL because the design has many functions required for an IOL moderately, is easy to manufacture, and is convenient for managing powers. However, an IOL is also being developed with attention being paid to a specific function (e.g., enabling an eye to see an object more clearly, or to see both distance and near objects) and with an aim for enhancing the function.

In relation to the specific function of enabling an eye to see an object more clearly, a typical aberration reduction type IOL is directed to improve the contrast, while sacrificing the visible distance range. When a spherical IOL is inserted into an eye, focal points are not concentrated on the retina because the aberration of the cornea itself and the aberration of the IOL overlap each other. An aberration reduction type IOL is directed to reduce these aberrations. The spherical aberrations of the cornea and of the IOL increase with increased pupil size. In other words, although influence due to the spherical aberration is small if a width of a light ray entering the eye is narrow, it could be significant if the width of the light ray is large. For example, a driver has a pupil diameter equal to or greater than 3.2 mm when s/he drives a car at night. Such pupil diameter is greatly affected by the spherical aberration such that the contrast of an object is deteriorated, which might be dangerous for driving a car. Technologies directed to solve this kind of problem are known (for example, see U.S. Pat. No. 4,504,982; Published Japanese Translation of a PCT Application No. 2003-534565; Japanese Patent Application Laid Open No. 2006-14818). However, they have a disadvantage in that they provide a smaller visible distance range compared with the spherical lens due to smaller depth of focus. These aberration correction lenses are directed to reduce the spherical aberration which would otherwise increase with increasing distance away from the optical axis. That is, when an IOL is placed into an eye, the optical axis of the IOL is not always aligned with the optical axis of the ocular (eyeball). Instead, it is common that the axes are offset from each other, and it has been reported in literature, textbooks, and the like that an axis offset of 0.3 mm in average is generated, and that in the case where the pupil diameter is large, deterioration in contrast in the aberration reduction type IOL caused by an axis offset is much greater compared with that in a spherical lens. See G. E. Altmann, L. D. Nichamin, S. S. Lane, and J. S. Pepose, "Optical performance of 3 intraocular lens designs in the presence of decentration," *J. Cataract Refract. Surg.*, 31, 574-85 (2005); R. Montés-Micó, T. Ferrer-Blasco, and A. Cerviño, "Analysis of the possible benefits of aspheric intraocular lenses: Review of the literature," *J. Cataract Refract. Surg.*, 35, 172-181 (2009); J. T. Holladay, P. A. Piers, G. Koranyi, M. van der Mooren, and N. E. Norrby, "A new intraocular lens design to reduce spherical aberration of pseudophakic eyes," *J. Refract. Surg.*, 18, 683-691 (2002); S. Barbero, S. Marcos, and I. Jiménez-Alfaro, "Optical aberrations of intraocular lenses measured in vivo and in vitro," *J. Opt. Soc. Am. A, Opt. Image Sci. Vis.*, 20, 1841-51 (2003).

In relation to the specific function of enabling an eye to see both distance and near objects, the designs of typical multifocal IOLs, in which the technology is directed for seeing distance and intermediate or near objects, differ depending on which distance priority is given to. In any of the designs, however, the light distribution for each distance is smaller compared with a case of a spherical lens which captures light with the entire lens. As a result, despite an increased visible distance range, the contrast of such lens is deteriorated (for example, see Japanese Patent Application Laid Open No. S60-85744).

In Published Japanese Translation of a PCT Application No. 2000-511439, the invention described therein is directed to provide a wider visible distance range compared with a spherical lens, for example, by employing a greater depth of focus for a near object, however, it does not provide a visible distance range covering all of distance, intermediate, and near objects. An IOL according to Published Japanese Translation of a PCT Application No. 2000-511439 results in a deteriorated contrast compared with a spherical lens, as well as halos, glares, waxy visions or other dysphotopsia shortages. See also M. A. Woodward, J. B. Randleman, and R. D. Stulting, "Dissatisfaction after multifocal intraocular lens implantation," *J. Cataract Refract. Surg.*, 35, 992-997 (2009); N. E. de Vries, C. A. B. Webers, W. R. H. Touwslager, N. J. C. Bauer, J. de Brabander, T. T. Berendschot, and R. M. M. A. Nuijts, "Dissatisfaction after implantation of multifocal intraocular lenses," *J. Cataract Refract. Surg.*, 37, 859-865 (2011); N. E. de Vries and R. M. M. A. Nuijts, "Multifocal intraocular lenses in cataract surgery: Literature review of benefits and side effects," *J. Cataract Refract. Surg.*, 39, 268-278 (2013).

There have been some attempts to overcome the above problems. One of the approaches involves using spherical aberrations (4th and 6th order spherical aberrations) to spread the depth of focus. See Y. Benard, N. Lopez-Gil, and R. Legras, "Subjective depth of field in presence of 4th-order and 6th-order Zernike spherical aberration using adaptive optics technology," *J. Cataract Refract. Surg.*, 36, 2129-2138 (2010); F. Yi, D. r. Iskander, and M. Collins, "Depth of focus and visual acuity with primary and secondary spherical aberration," *Vision Research*, 51, 1648-1658

(2011). However, as mentioned above, the remaining spherical aberrations in the ocular system may reduce the visual contrast, especially in a large pupil diameter. In such a design, by compromising contrast reduction and depth of focus, the depth of focus could be extended only up to about 0.75 D, or total visual depth of focus becomes about 1.5 D to 1.75 D. A wider depth of focus of about 3 diopters is necessary for whole visual distance range.

A light sword optical element (LSOE), an approach to design a wide range depth of focus, has been proposed in 1990 by Prof. A. Kolodziejczyk et al., where additionally an angular modulation of a transmittance was implemented. See A. Kolodziejczyk, S. Bará, Z. Jaroszewicz, and M. Sypek, "The light sword optical element—a new diffraction structure with extended depth of focus," *J. Mod. Opt.*, 37, 1283-1286 (1990). The proposed lens (in Kolodziejczyk et al.) indicated superiority of the diffractive LSOE over the other diffractive elements with radial modulation of the transmittance in an optical set-up simulating a human eye. Nevertheless, diffractive elements including those focusing light in a line segment suffer from substantial chromatic aberration. In relation to theoretical and other evaluations of refractive LSOE, see J. A. Garcia, S. Bará, M. G. Garcia, Z. Jaroszewicz, A. Kolodziejczyk, and K. Petelczyc, "Imaging with extended focal depth by means of the refractive light sword optical element," *Opt. Express*, 16, 18371-18378 (2008); K. Petelczyc, J. A. Garcia, S. Bará, Z. Jaroszewicz, K. Kakarenko, A. Kolodziejczyk, and M. Sypek, "Strehl ratios characterizing optical elements designed for presbyopia compensation," *Opt. Express*, 19, 8693-8699 (2011); K. Petelczyc, S. Bará, A. C. Lopez, Z. Jaroszewicz, K. Kakarenko, A. Kolodziejczyk, and M. Sypek, "Imaging properties of the light sword optical element used as a contact lens in a presbyopic eye model," *Opt. Express*, 19, 25602-25616 (2011); A. A. Gallego, S. Bará, Z. Jaroszewicz, and A. Kolodziejczyk, "Visual Strehl performance of IOL designs with extended depth of focus," *Optom. Vis. Sci.*, 89, 1702-1707 (2012).

It would be helpful (e.g., for aphakic patients after cataract surgery and for presbyopia compensation) to be able to provide an IOL having a wide range depth of focus (e.g., a depth of focus of about 3 diopters or more) or having a relatively less wide depth of focus and, additionally, that is not unacceptably compromised in its imaging properties (or image quality) by one or more deficiencies associated with prior approaches/designs.

It would be helpful to be able to manufacture such an IOL utilizing a cast molding procedure or a lathe cut procedure.

SUMMARY OF THE INVENTION

Embodiments described herein relate to technologies and methodologies for providing a wide range depth of focus intraocular lens (IOL). In an example implementation described herein, an optical device or optical element is provided in the form of a "vortex IOL", a true multifocal IOL design, composed entirely of refractive optical element with spiral or helical structure having the ability to control the refractive foci of the incident light. From both analytical and experimental results determined by the present inventor(s), this kind of IOL in example embodiments and implementations enables extending the depth of focus up to 4 diopters and therefore could be very beneficial for aphakic patients after cataract surgery and presbyopia compensation. In example embodiments and implementations, the vortex IOL restores not only visual function at distance but also at different distances. Other embodiments described herein relate to technologies and methodologies for providing an IOL that has a relatively less wide depth of focus.

In an example embodiment, an optical device includes an intraocular lens (IOL) composed of entirely refractive optical element(s) implementing an angular modulation of a transmittance of said lens.

In an example embodiment, an optical device includes an intraocular lens (IOL) composed of entirely refractive optical element(s) implementing an angular modulation of a transmittance of said lens; wherein the lens provides total visual depth of focus (DOF) for the optical device of about 1.0 D to 2.0 D.

In an example embodiment, an optical device includes an intraocular lens (IOL) composed of entirely refractive optical element(s) implementing an angular modulation of a transmittance of said lens; wherein the azimuthal power distribution principally implements a distance vision zone and an intermediate vision zone.

In an example embodiment, an optical device includes an intraocular lens (IOL) comprising an entirely refractive multifocal optical element implemented to control the refractive foci of incident light.

In an example embodiment, an optical device includes an intraocular lens (IOL) comprising an entirely refractive optical element with spiral or helical structure implemented to control the refractive foci of incident light.

In an example embodiment, an optical device includes an intraocular lens (IOL) composed of entirely refractive optical element(s) implementing amplitude apodization from the center to one or more edge, periphery or optical boundary of said lens.

In an example embodiment, an optical device includes an intraocular lens (IOL) having entirely refractive optical element(s) including one or more surfaces implementing an azimuthal power distribution, and a peripheral optic portion that is devoid, or substantially devoid, of azimuthal power distribution and implemented to provide a refractive focus corresponding to far or intermediate vision.

In an example embodiment, a process for manufacturing an optical device includes the step(s) of: molding and/or cutting a material to form an intraocular lens (IOL) implementing an angular modulation of a transmittance of said lens, the lens including one or more surfaces implementing an azimuthal power distribution, and entirely or substantially eliminating any discontinuity along said azimuthal power distribution.

In example embodiments and implementations, the diffractive LSOE design serves as a basis for refractive optics for vortex IOL (or other optical devices) designs. Therefore, informally and for illustrative purposes only, the LSOE design can be thought of being "modified" to provide a refractive counterpart (of the diffractive LSOE) for the refractive optics for vortex IOL design, the aforementioned designs thusly being referred to herein in some instances as "vortex IOL" and "modified vortex IOL", respectively.

BRIEF DESCRIPTION OF THE DRAWINGS

FIG. 1A shows the power map distribution and FIG. 1B shows its azimuthal plot.

FIG. 2A shows the power map distribution and FIG. 2B shows its azimuthal plot.

FIG. 3A shows the power map distribution and FIG. 3B shows its azimuthal plot.

FIG. 4A shows the power map distribution and FIG. 4B shows its azimuthal plot.

FIG. 5A shows the power map distribution and FIG. 5B shows its azimuthal plot.

FIG. 6A shows the power map distribution and FIG. 6B shows its azimuthal plot.

FIGS. 13A and 13B respectively show the visual Strehl ratio map and the visual Strehl ratio contour map (with contour lines) for modified vortex IOL with ΔP=4.0 D in spherical design.

FIGS. 17A and 17B show the visual defocus responses calculated at 3.0 mm pupil size and at 4.5 mm pupil size, respectively, for modified vortex IOL with ΔP=3.0 D in spherical design.

FIGS. 18A and 18B show the visual defocus responses calculated at 3.0 mm pupil size and at 4.5 mm pupil size, respectively, for modified vortex IOL with ΔP=3.0 D in aspheric design.

FIG. 27A shows the fringes for a vortex IOL and FIG. 27B shows the fringes for a modified vortex IOL.

FIG. 28A shows the modulation map for a vortex IOL and FIG. 28B shows the modulation map for a modified vortex IOL.

FIG. 29A shows a vortex IOL and FIG. 29B shows a modified vortex IOL.

FIG. 30A shows the USAF image for a vortex IOL and FIG. 30B shows the USAF image for a modified vortex IOL.

FIG. 31A shows the USAF image for a vortex IOL and FIG. 31B shows the USAF image for a modified vortex IOL.

FIG. 39 shows 3D scene images for eight different IOLs at 3.0 mm pupil size.

FIG. 43A shows the power map distribution and FIG. 43B shows its azimuthal plot.

FIG. 44A shows the power map distribution and FIG. 44B shows its azimuthal plot.

DISCLOSURE OF INVENTION

Figures 1A, 1B:
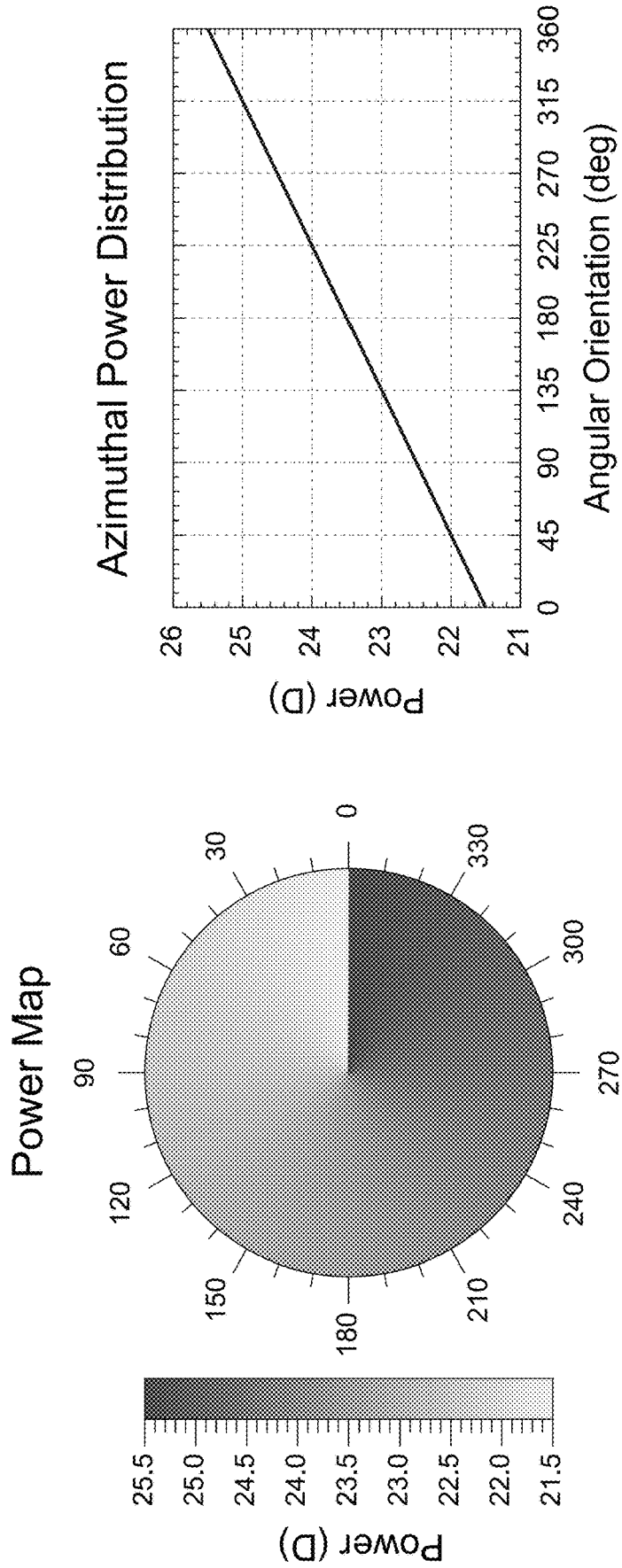
FIGS. 1A and 1B show the optical power distribution for vortex IOL according to the IOL power stretched from 21.5 D to 25.5 D.

Example embodiments of the invention(s) described herein involve intraocular lenses (IOLs) implemented in the form of new, and heretofore unknown, entirely refractive optical element(s) designs. It is contemplated that the principles of the present invention(s) are applicable to optical element(s) for and may be appropriately adapted in various implementations to other optical devices including but not limited to contact lenses.

An example embodiment of an optical design, referred to herein as a "Vortex IOL", a true multifocal IOL design which provides a wide range of depth of focus, is now described. In example implementations, the Vortex IOL is composed entirely of refractive optical element with vortic, spiral, or helical structure having the ability to control the refractive foci of the incident light. By way of example, the refractive optical element is the refractive counterpart of a diffractive optical element (e.g., the refractive counterpart of an IOL optical element previously known only to exist in the form of or inclusive of diffractive element).

The optical design and the numerical analysis of the optical characteristics of the Vortex IOL are described and compared to the optical imaging elements currently available in the world-wide market. The comparisons were performed using an anatomically accurate finite model eye, which was modified to include the IOL except the human crystalline lens model.

Vortex IOL Description

The presbyopic eye compensated by a vortex IOL optical structure based on the LSOE design (A. Kolodziejczyk, S. Bará, Z. Jaroszewicz, and M. Sypek, "The light sword optical element—a new diffraction structure with extended depth of focus," *J. Mod. Opt.*, 37, 1283-1286 (1990), which is hereby incorporated by reference) provides the following optical path difference (OPD):

$$OPD(r,\theta) = -\frac{r^2}{2\left(f + \Delta f \frac{\theta}{2\pi}\right)}. \quad (1)$$

where r and θ are the radial and the azimuthal coordinate in the polar coordinate system, respectively. Then, each infinitesimal angular sector corresponds to a spherical lens with a focal length of f−Δf θ/(2π). Therefore, the LSOE focuses an incident plane wave into a focal segment stretched from f up to f+Δf behind the LSOE structure.

In example embodiments, the LSOE design is "modified" to (e.g., serves as a basis for) a refractive optics for vortex IOL (or other optical device) design. A simple lens equation (see F. A. Jenkins and H. E. White, "*Fundamentals of optics,*" 4th ed., 81-87, McGraw-Hill, Singapore (1985), which is hereby incorporated by reference) can be used to derive the apex radii for the aspheric anterior surface and the radii for the spherical posterior surface. The calculation of lens dioptric power, P, in aqueous is described by the following equation:

$$P = \left(\frac{n_{IOL} - n_{Aqueous}}{r_A}\right) + \left(\frac{n_{Aqueous} - n_{IOL}}{r_P}\right) - \frac{CT}{n_{IOL}}\left(\frac{n_{IOL} - n_{Aqueous}}{r_A}\right)\left(\frac{n_{Aqueous} - n_{IOL}}{r_P}\right). \quad (2)$$

where P is the dioptric power, $n_{IOL}$ is the refractive index of the IOL optics material, $n_{Aqueous}$ is the refractive index of the IOL surrounding medium, $r_A$ and $r_P$ are the radius curvature of the anterior and posterior of the IOL in meters, respectively, and CT is the center thickness of the IOL in meters. The vortex IOL is designed such that each line angular element corresponds to a dioptric power of P+ΔP θ/(2π), where θ is the azimuthal coordinate in the polar coordinate system as mentioned previously. Therefore, the vortex IOL itself focuses an incident plane wave segment stretched from P up to P+ΔP.

"Modified" Vortex IOL

Figures 2A, 2B:
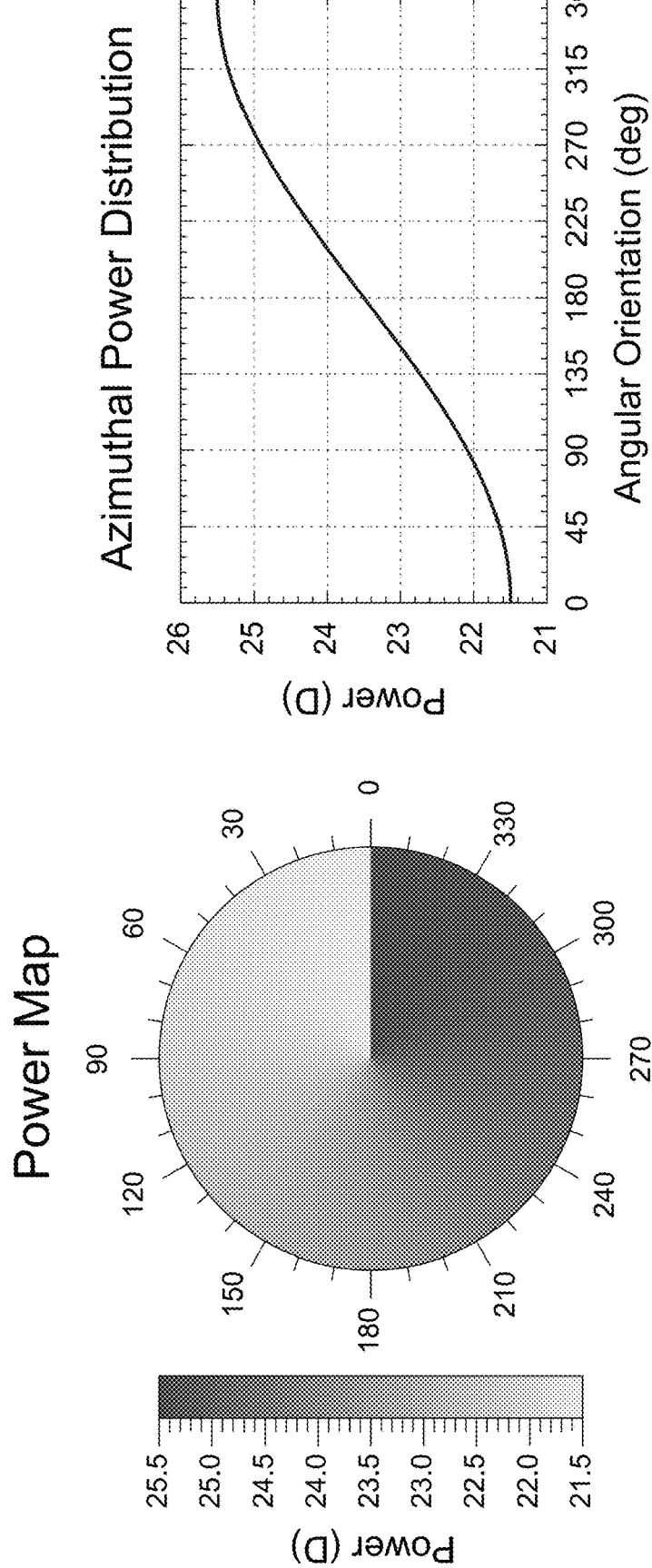
FIGS. 2A and 2B show the optical power distribution for modified vortex IOL according to the IOL power stretched from 21.5 D to 25.5 D.

A new Vortex IOL design aimed for restoring not only visual function at distance but also at different distances has been developed and is described herein. In example embodiments, the azimuthal distribution of the lens dioptric power is provided, adapted, and/or implemented as a non-linear distribution, such that the foci for distance and near objects are dominant. A sinusoidal or an error function, for example, could be effective for this purpose. An example for a line angular element with a sinusoidal azimuthal power distribution corresponds to a dioptric power of P+ΔP*0.5 [1−cos (θ/2)]. FIGS. 1 and 2 respectively show the optical power distribution for a linear and a sinusoidal modified vortex IOL according to the IOL power stretched from 21.5 D to 25.5 D, or with a ΔP of 4.0 D.

Figures 3A, 3B:
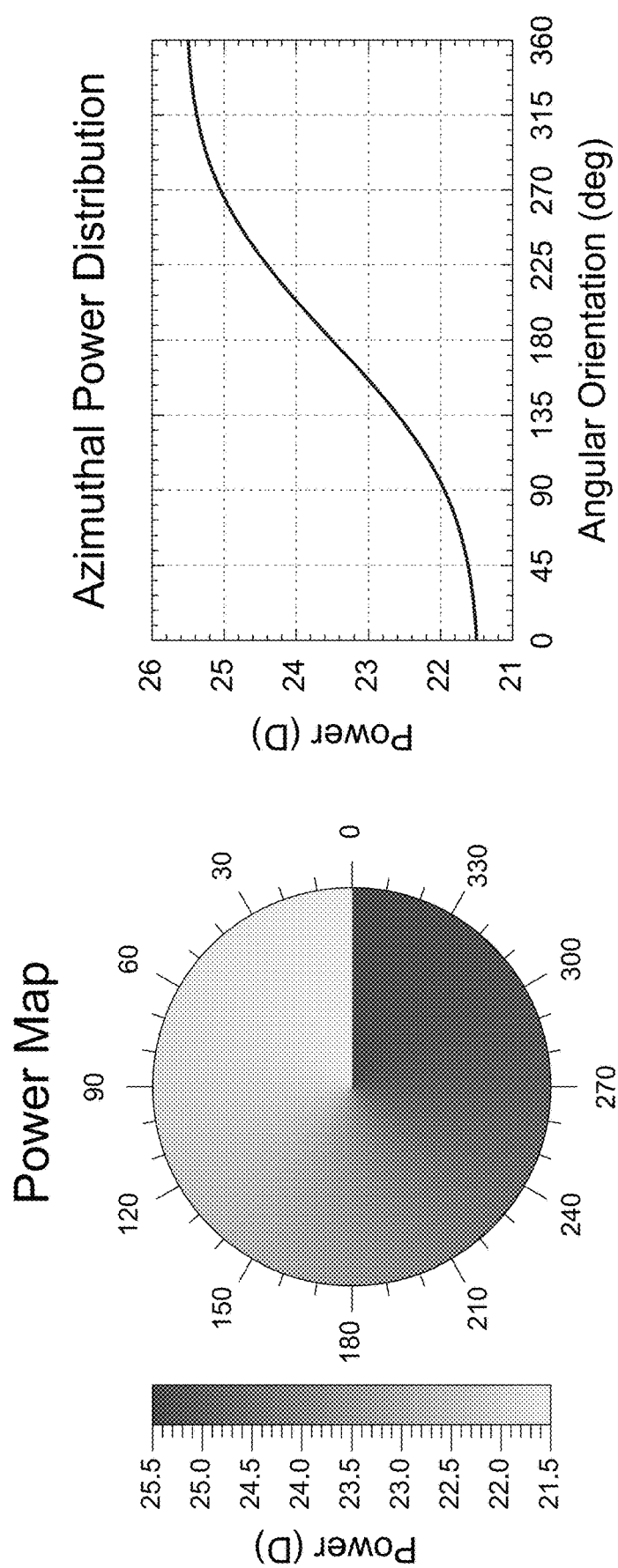
FIGS. 3A and 3B show the optical power distribution for modified vortex IOL according to the IOL power stretched from 21.5 D to 25.5 D using an error function with σ=0.3.
Figures 4A, 4B:
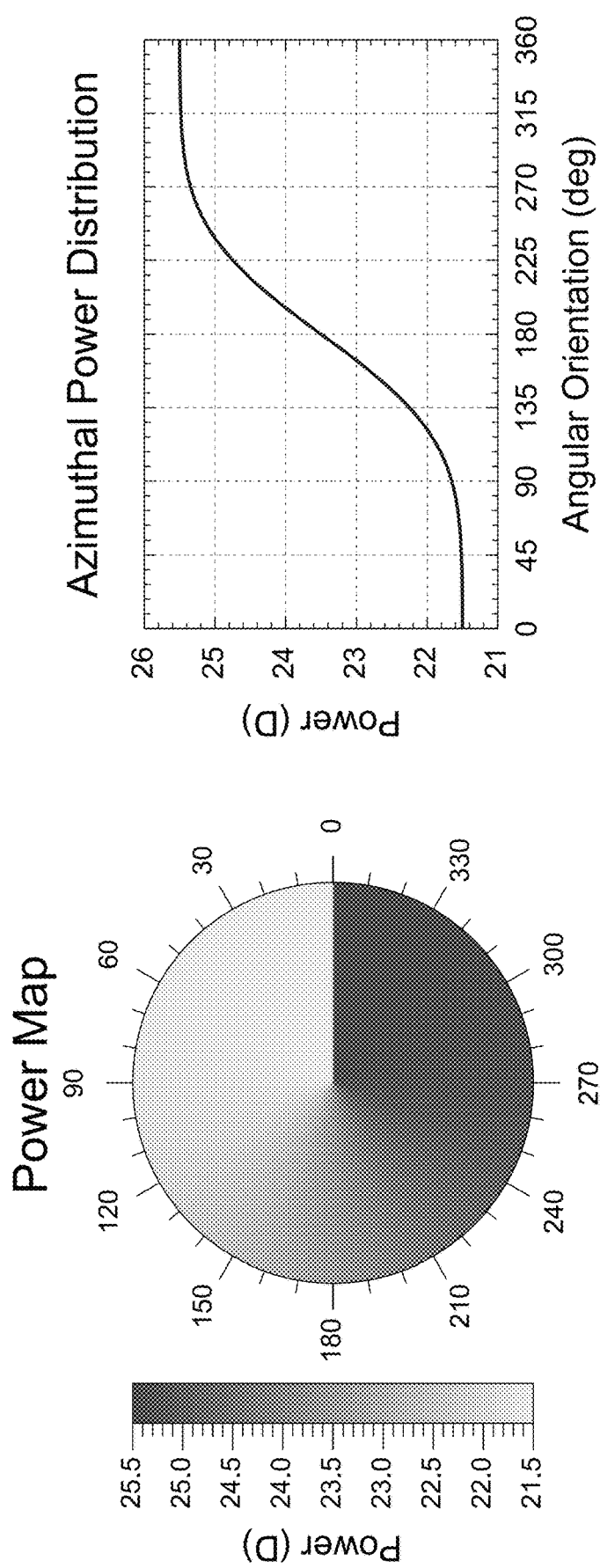
FIGS. 4A and 4B show the optical power distribution for modified vortex IOL according to the IOL power stretched from 21.5 D to 25.5 D using an error function with σ=0.2.

FIGS. 3 and 4 show other examples with an error function azimuthal power distribution corresponds to a dioptric power of P+ΔP*0.5 erfc[(π−θ)/(2πσ)], where erfc is a complementary error function in terms of the parameter σ and expressed in Eq. 3.

$$erfc(x) = 1 - \frac{2}{\sqrt{\pi}}\int_0^2 \exp(-t^2)dt. \quad (3)$$

Vortex IOL with Surface Step Reduction

FIGS. 1 and 2 show that a vortex IOL will have rapidly changed surface step profile at the boundary between the angular sectors corresponding to the lowest dioptric power and the highest dioptric power, respectively. In order to minimize this surface step, in example embodiments, an azimuthal power distribution is implemented for 0≤θ<2π−α, where α is a small angle not excessing π/6 or 30°, which can be viewed as in effect introducing an angular separation (zone) between the lowest dioptric power sector and the highest dioptric power sector. The rest (or remainder) of the azimuthal power distribution, that is for 2π−α≤θ<2π, can be similar to the opposite of its azimuthal power distribution (for 0≤θ<2π−α), which is stretching from high to low dioptric power. For α≠0, this vortex IOL with surface step reduction can be mathematically expressed as $$P_{Vortex} = \begin{cases} P + \Delta P \dfrac{\theta}{2\pi - \alpha}, & \text{for } 0 \le \theta < 2\pi - \alpha, \\ P + \Delta P \dfrac{2\pi - \theta}{\alpha}, & \text{for } 2\pi - \alpha \le \theta < 2\pi. \end{cases} \quad (4)$$

and $$P_{M-Vortex} = \begin{cases} P + \Delta P * 0.5\left[1 - \cos\left(\dfrac{\pi\theta}{2\pi - \alpha}\right)\right], & \text{for } 0 \le \theta < 2\pi - \alpha \\ P + \Delta P * 0.5\left[1 - \cos\left(\dfrac{\pi(2\pi - \theta)}{\alpha}\right)\right], & \text{for } 2\pi - \alpha \le \theta < 2\pi \end{cases}, \quad (5)$$

where $P_{Vortex}$ and $P_{M-Vortex}$ are the power profiles for a linear and a sinusoidal modified vortex IOL, respectively. The equation for an error function modified vortex IOL can be obtained by a similar approach and mathematically expressed as $$P_{M-Vortex} = \begin{cases} P + \Delta P * 0.5\, erfc\left[\dfrac{(\pi - 0.5\alpha) - \theta}{(2\pi - \alpha)\sigma}\right], & \text{for } 0 \le \theta < 2\pi - \alpha \\ P + \Delta P * 0.5\, erfc\left[\dfrac{\theta - (2\pi - 0.5\alpha)}{\alpha\sigma}\right], & \text{for } 2\pi - \alpha \le \theta < 2\pi \end{cases}, \quad (6)$$

Figures 5A, 5B:
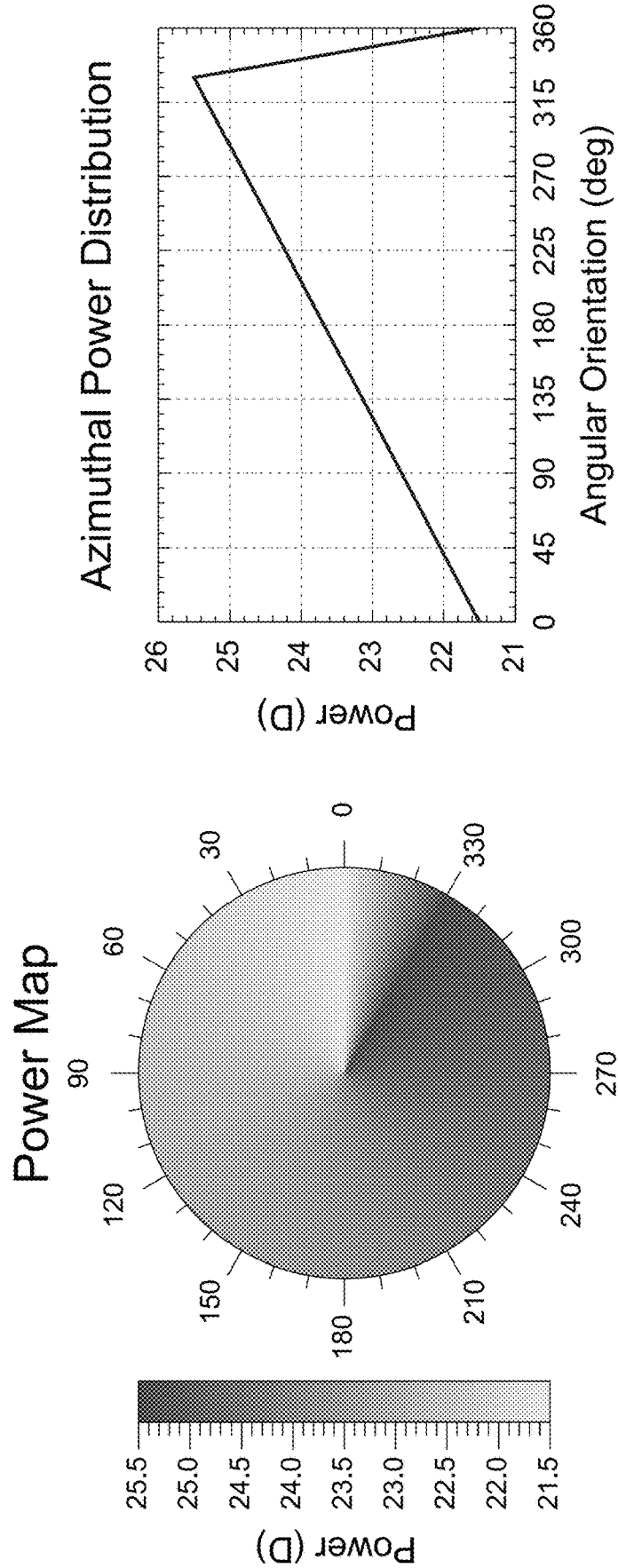
FIGS. 5A and 5B show the optical power distribution for vortex IOL with surface step reduction of α=30° according to the IOL power stretched from 21.5 D to 25.5 D.
Figures 6A, 6B:
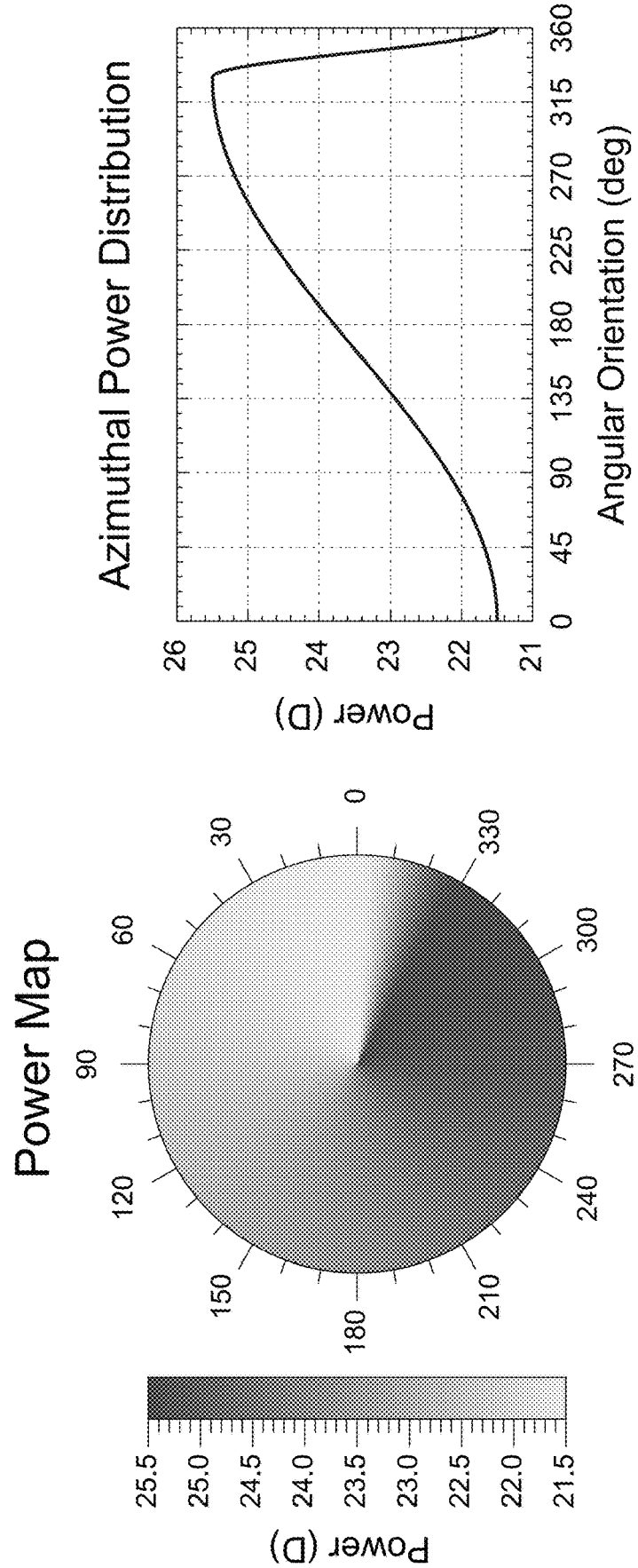
FIGS. 6A and 6B show the optical power distribution for modified vortex IOL with surface step reduction of α=30° according to the IOL power stretched from 21.5 D to 25.5 D.
Figure 7B:
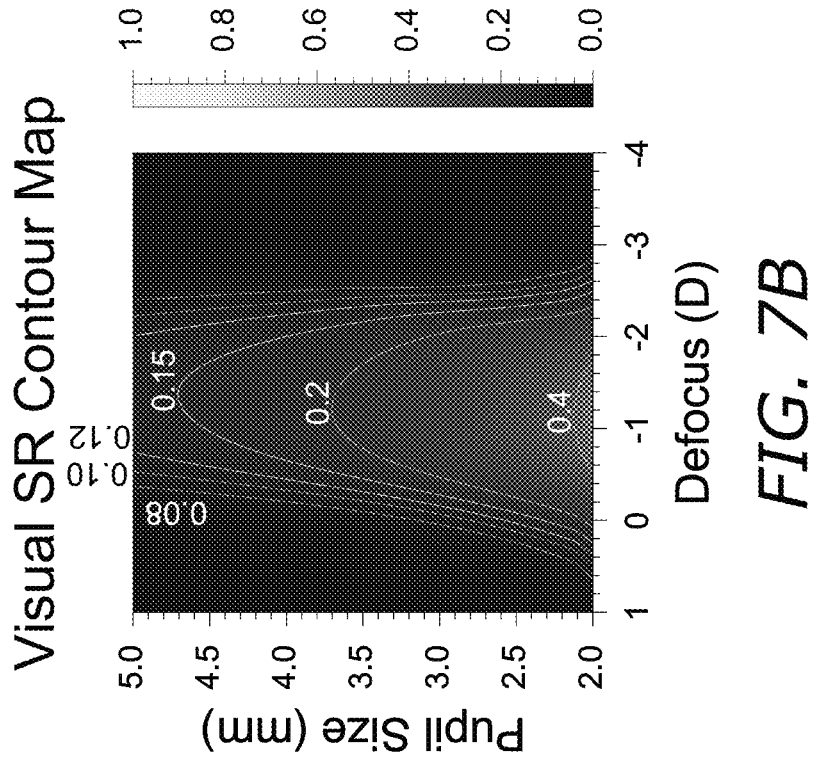
FIGS. 7A and 7B respectively show the visual Strehl ratio map and the visual Strehl ratio contour map (with contour lines) for vortex IOL with ΔP=3.0 D in spherical design.
Figure 7A:
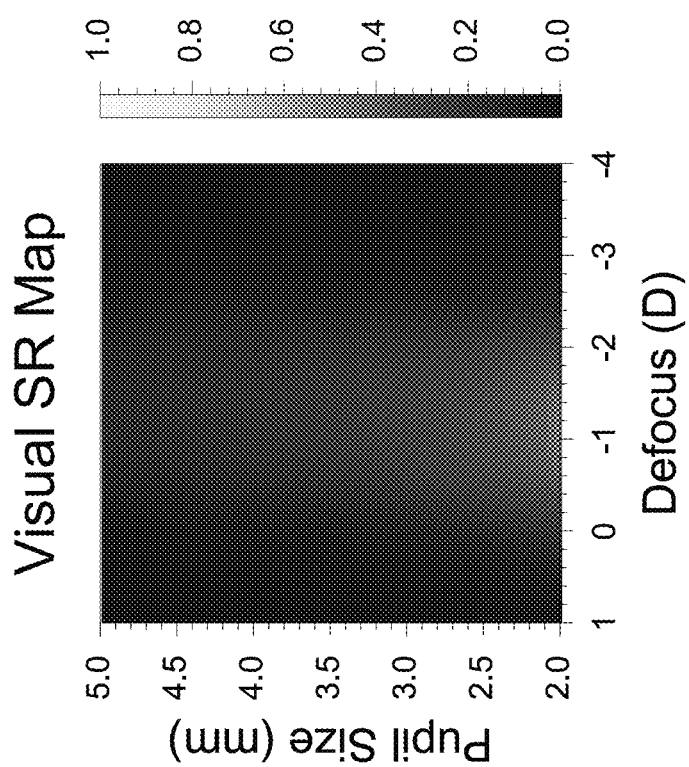
Figures 8A, 8B:
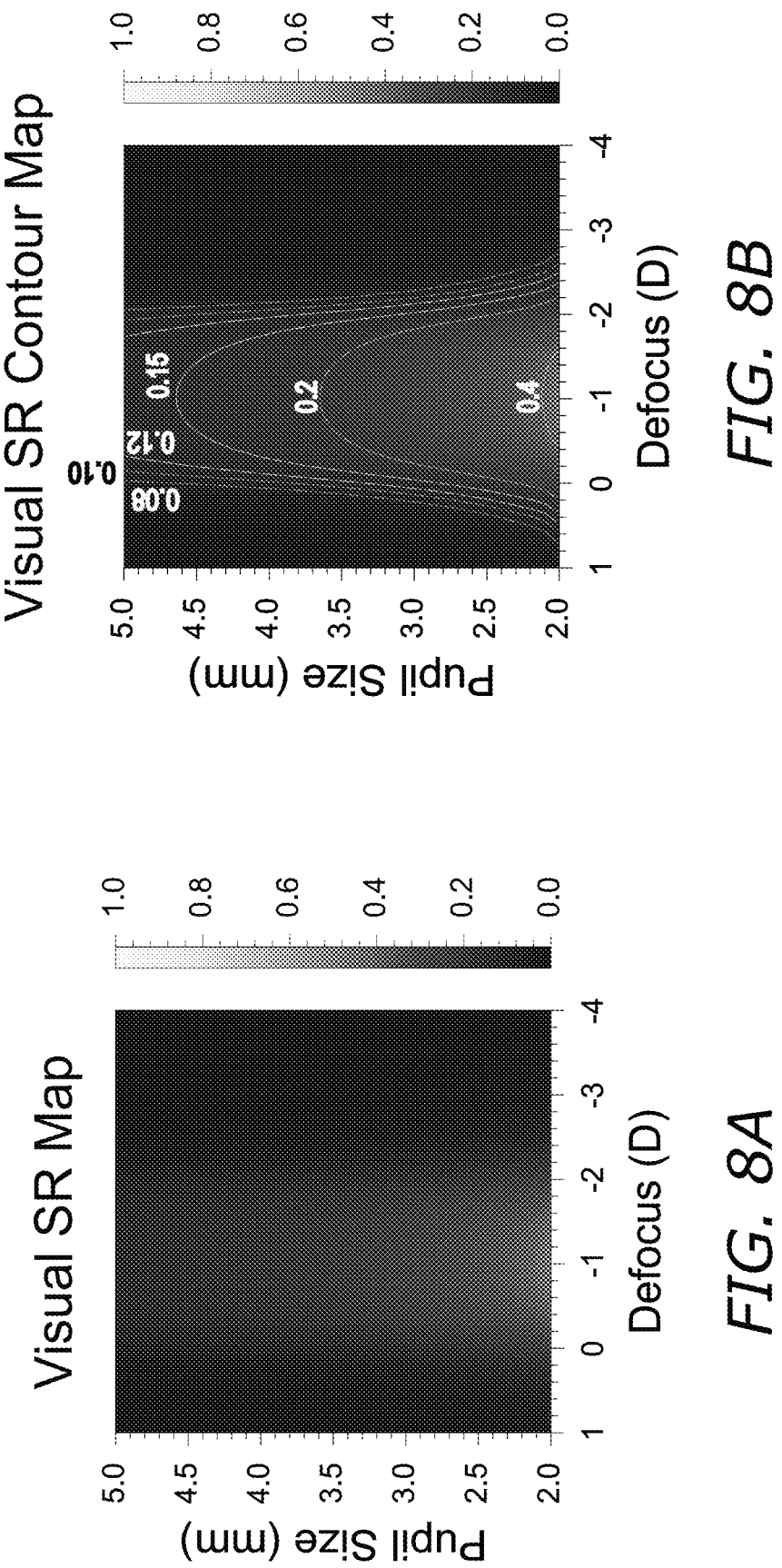
FIGS. 8A and 8B respectively show the visual Strehl ratio map and the visual Strehl ratio contour map (with contour lines) for vortex IOL with ΔP=3.0 D in aspheric design.
Figures 9A, 9B:
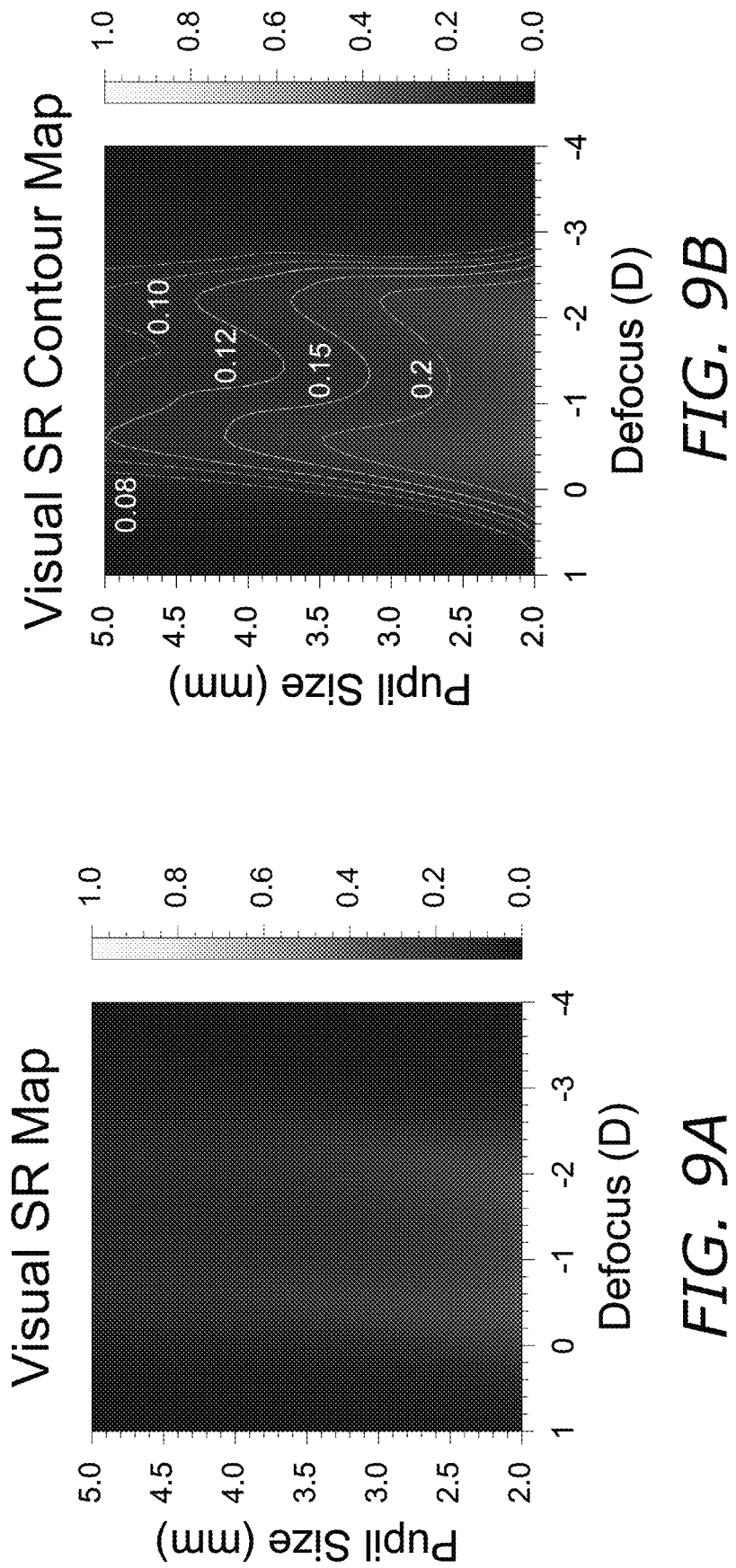
FIGS. 9A and 9B respectively show the visual Strehl ratio map and the visual Strehl ratio contour map (with contour lines) for modified vortex IOL with ΔP=3.0 D in spherical design.
Figures 10A, 10B:
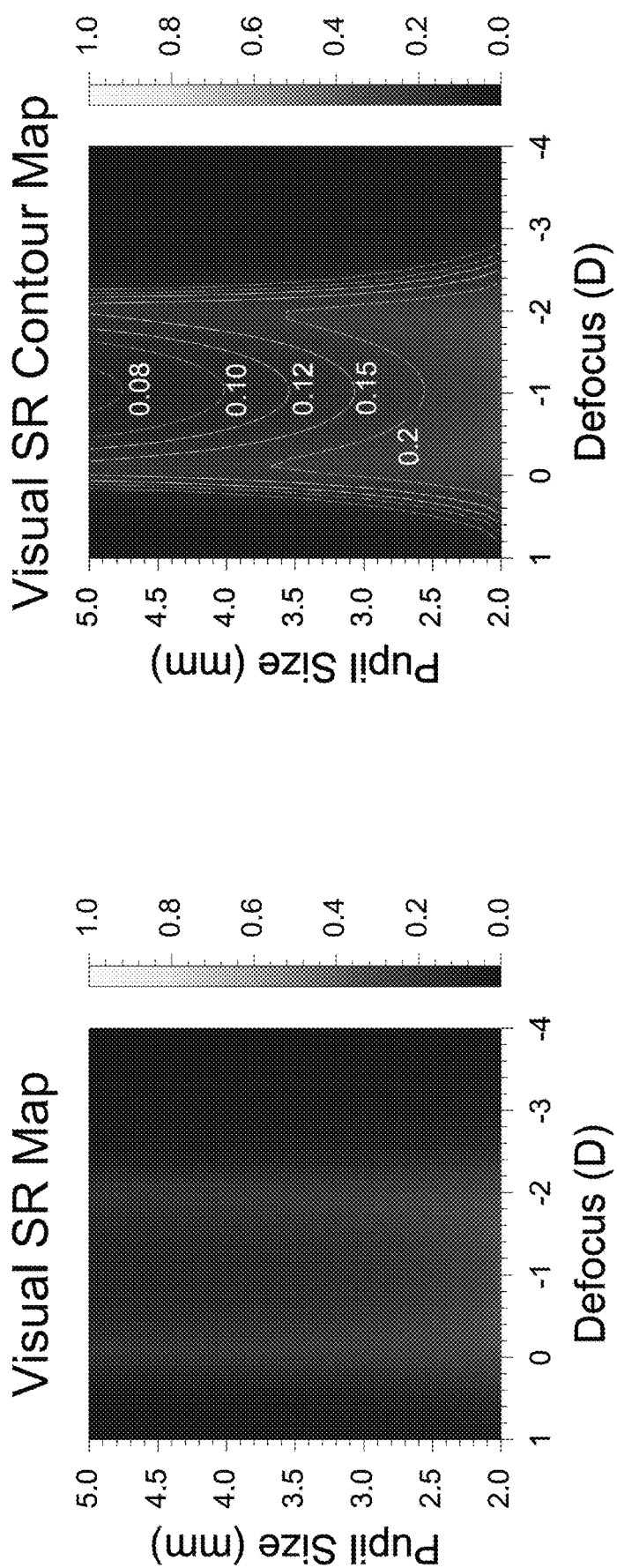
FIGS. 10A and 10B respectively show the visual Strehl ratio map and the visual Strehl ratio contour map (with contour lines) for modified vortex IOL with ΔP=3.0 D in aspheric design.
Figures 11A, 11B:
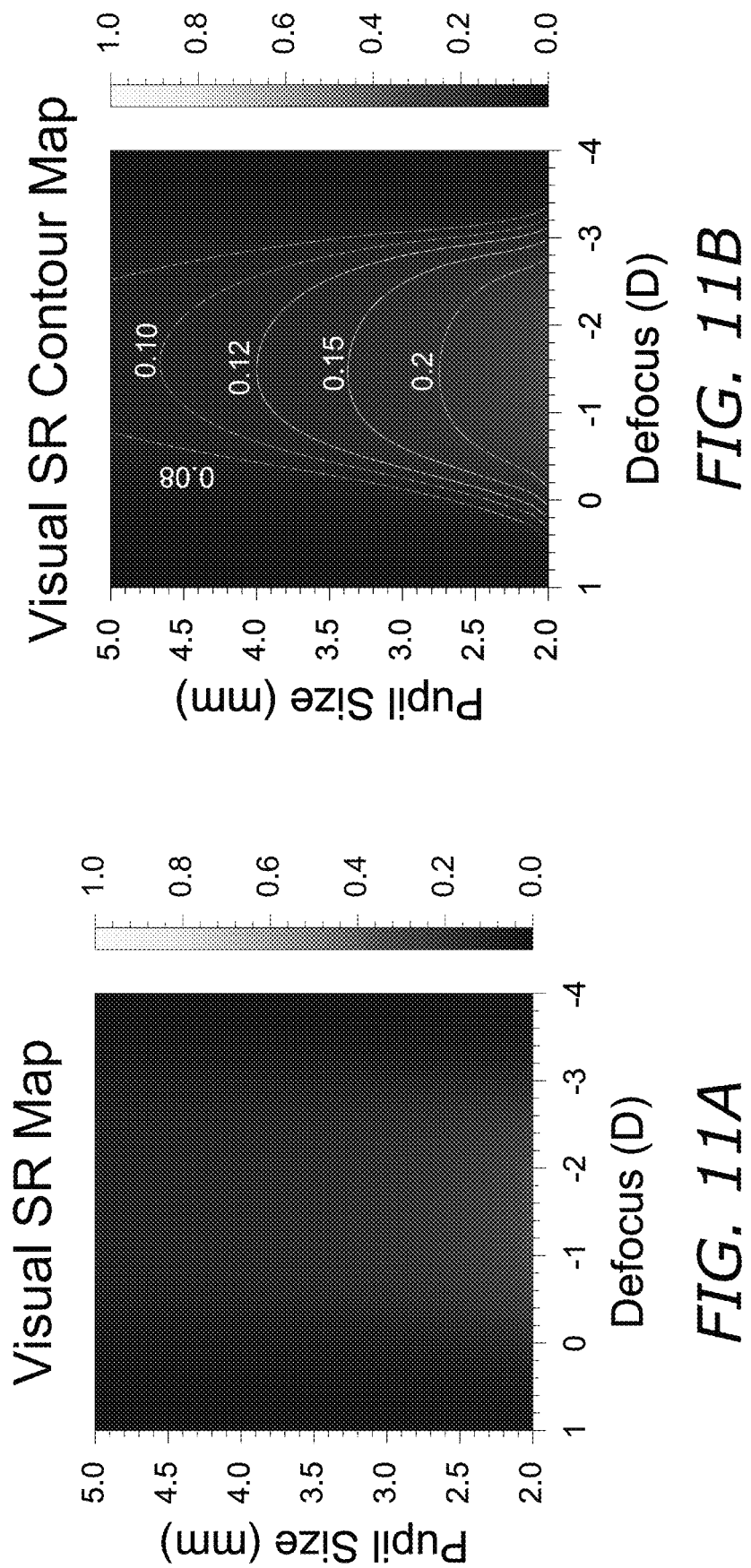
FIGS. 11A and 11B respectively show the visual Strehl ratio map and the visual Strehl ratio contour map (with contour lines) for vortex IOL with ΔP=4.0 D in spherical design.
Figures 12A, 12B:
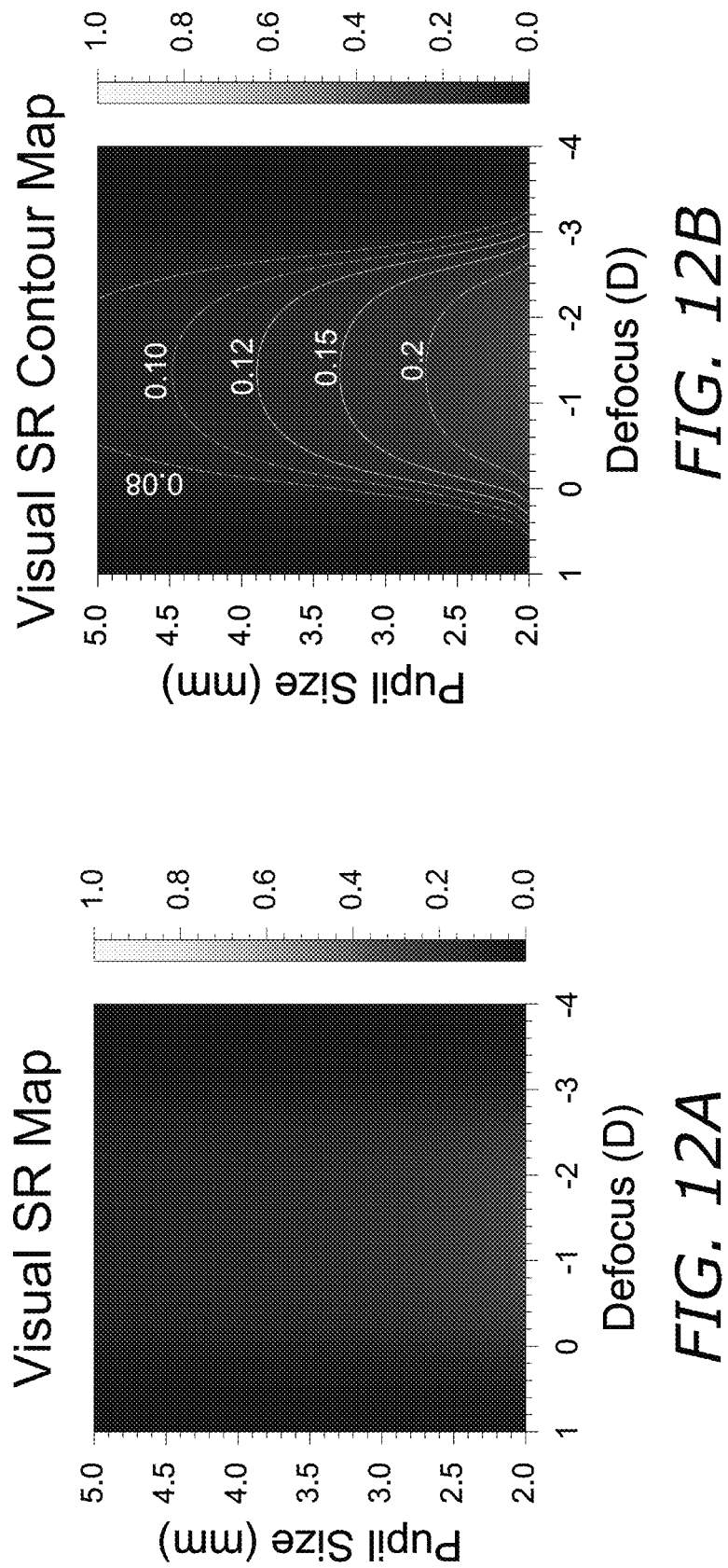
FIGS. 12A and 12B respectively show the visual Strehl ratio map and the visual Strehl ratio contour map (with contour lines) for vortex IOL with ΔP=4.0 D in aspheric design.
Figure 14B:
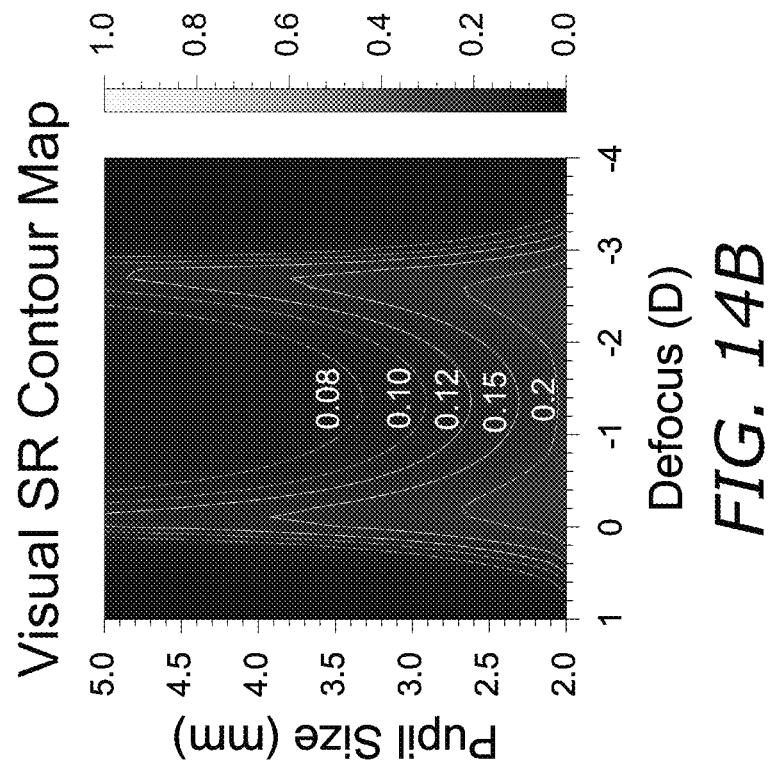
FIGS. 14A and 14B respectively show the visual Strehl ratio map and the visual Strehl ratio contour map (with contour lines) for modified vortex IOL with ΔP=4.0 D in aspheric design.
Figure 14A:
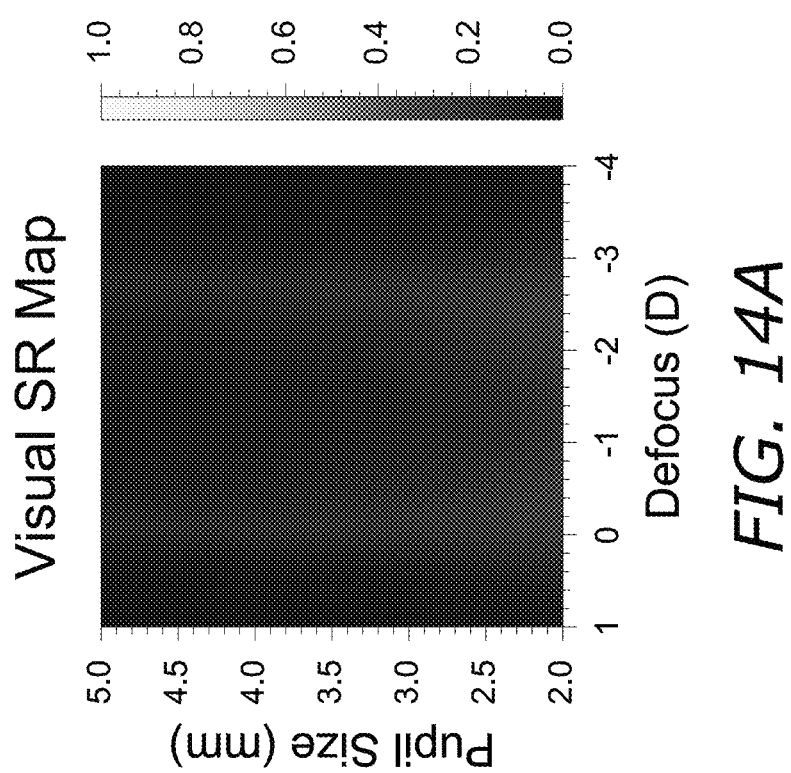
Figure 15A:
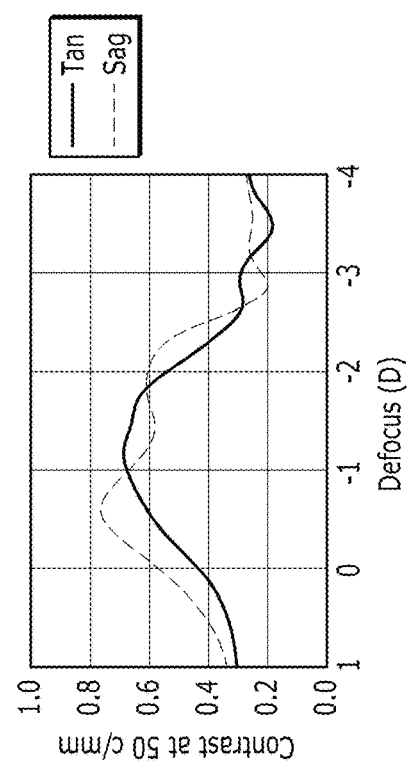
FIGS. 15A and 15B show the visual defocus responses calculated at 3.0 mm pupil size and at 4.5 mm pupil size, respectively, for vortex IOL with ΔP=3.0 D in spherical design.
Figure 15B:
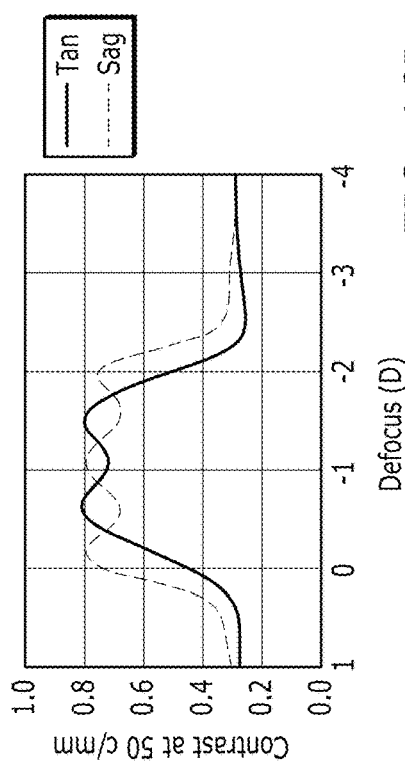
Figure 16A:
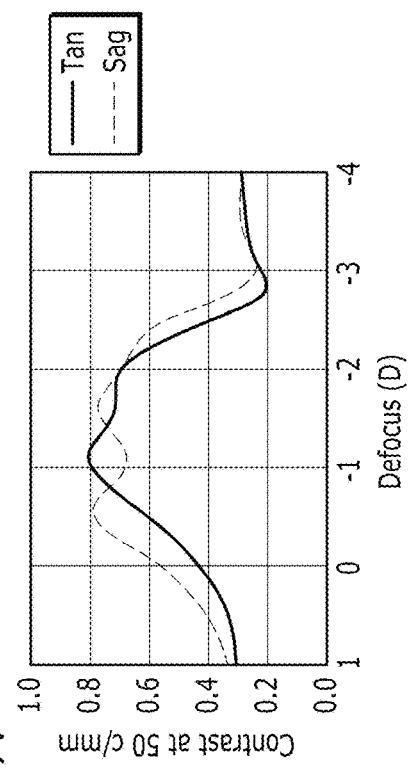
FIGS. 16A and 16B show the visual defocus responses calculated at 3.0 mm pupil size and at 4.5 mm pupil size, respectively, for vortex IOL with ΔP=3.0 D in aspheric design.
Figure 16B:
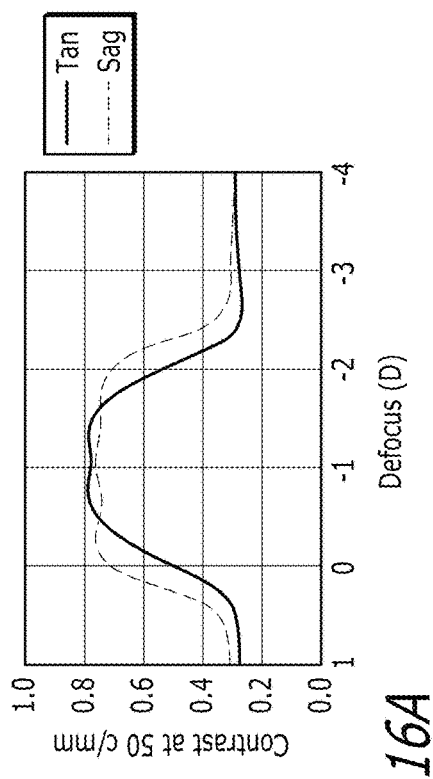
Figure 19A:
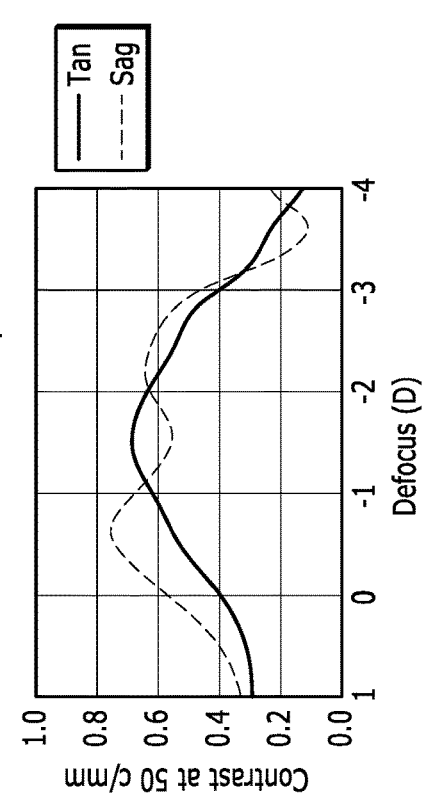
FIGS. 19A and 19B show the visual defocus responses calculated at 3.0 mm pupil size and at 4.5 mm pupil size, respectively, for vortex IOL with ΔP=4.0 D in spherical design.
Figure 19B:
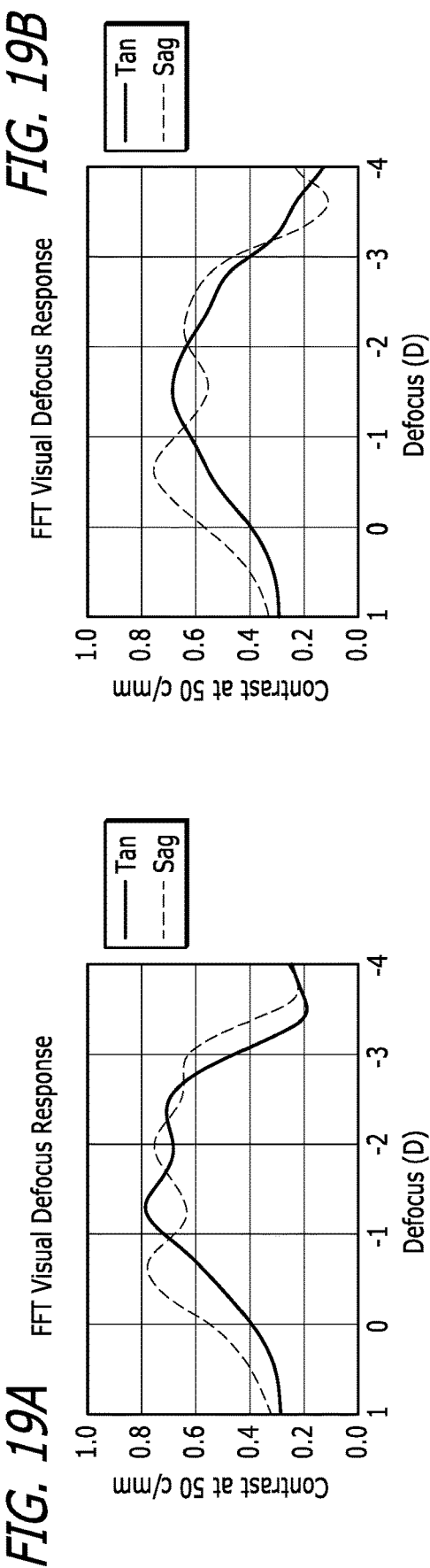
Figure 20A:
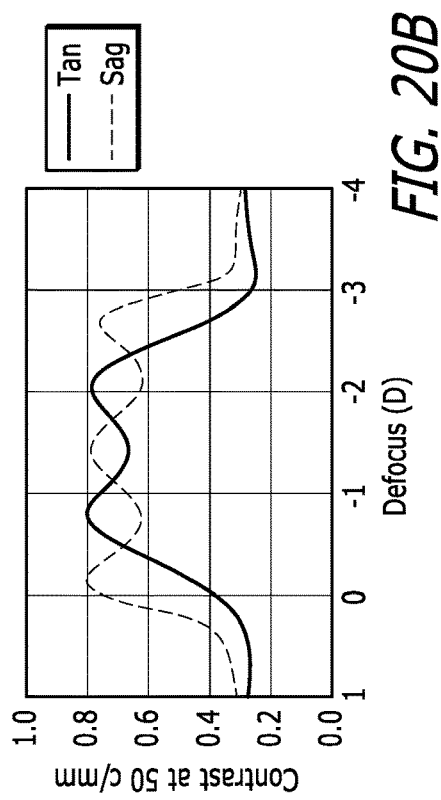
FIGS. 20A and 20B show the visual defocus responses calculated at 3.0 mm pupil size and at 4.5 mm pupil size, respectively, for vortex IOL with ΔP=4.0 D in aspheric design.
Figure 20B:
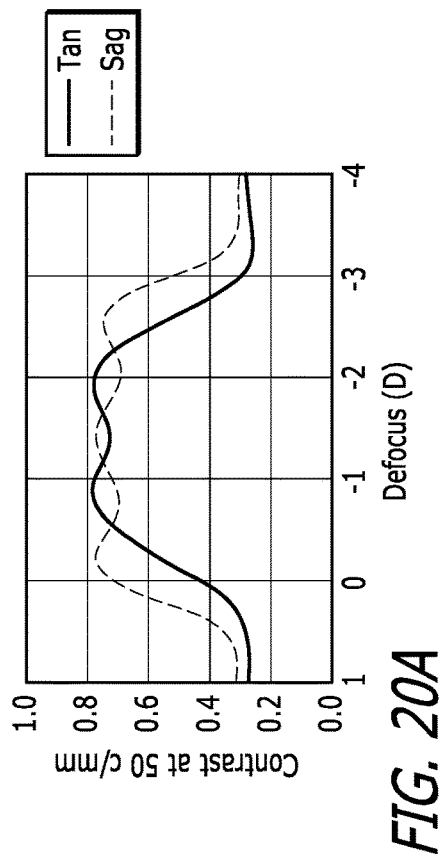
Figure 21A:
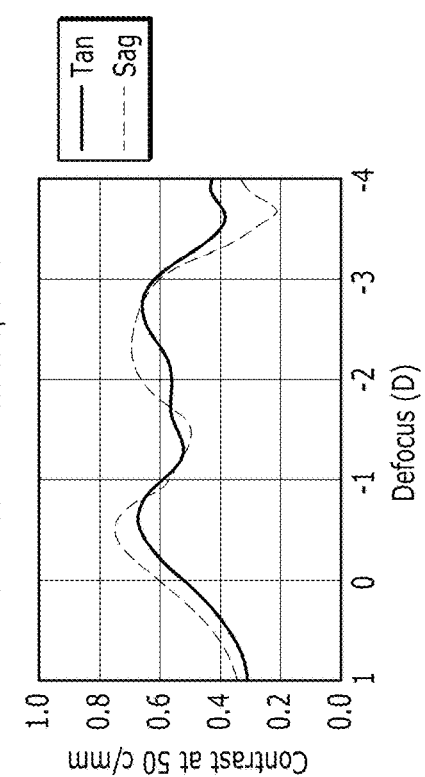
FIGS. 21A and 21B show the visual defocus responses calculated at 3.0 mm pupil size and at 4.5 mm pupil size, respectively, for modified vortex IOL with ΔP=4.0 D in spherical design.
Figure 21B:
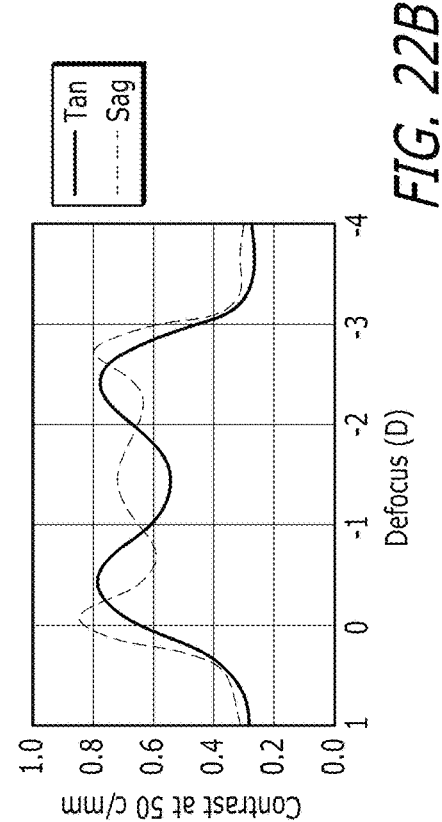
Figure 22A:
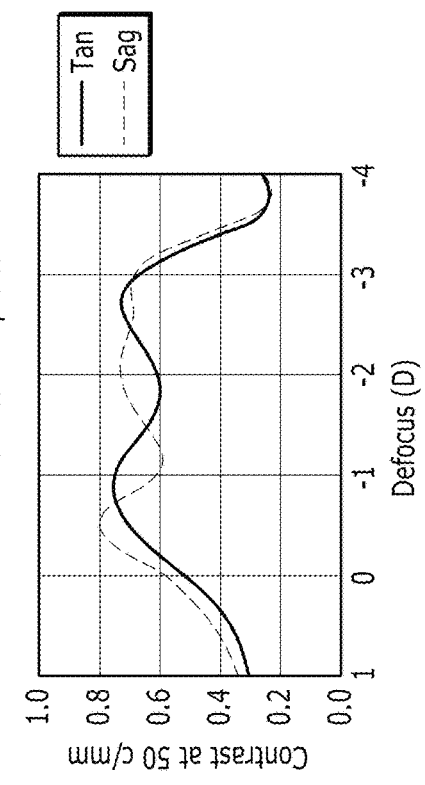
FIGS. 22A and 22B show the visual defocus responses calculated at 3.0 mm pupil size and at 4.5 mm pupil size, respectively, for modified vortex IOL with ΔP=4.0 D in aspheric design.
Figure 22B:
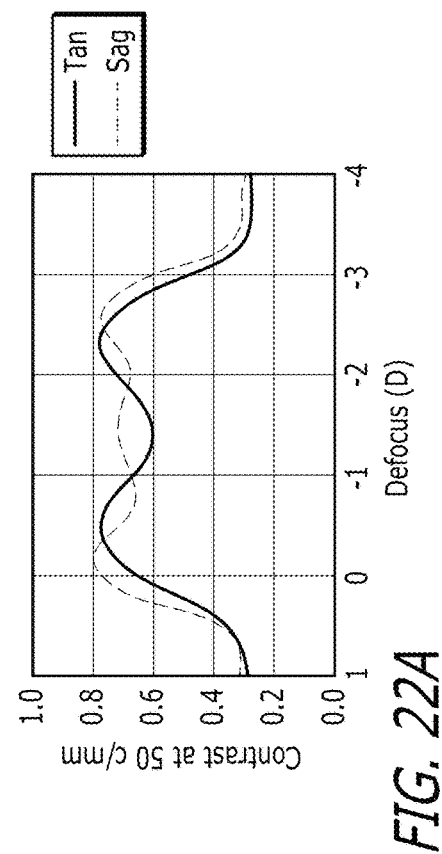

In example implementations, the profile of at least a portion of said lens is implemented using erfc function that includes smoothing (step reduction) for eliminating the discontinuity at 0 degree. This smoothing is also used so the lens can be manufactured without or substantially without any "overshot", i.e., oscillations in the lathe cut machine movements near the step (before stable condition of movement control is achieved). FIGS. 5 and 6 respectively show the optical power distribution for a linear and a sinusoidal modified vortex IOL with surface step reduction of α=30° according to the IOL power stretched from 21.5 D to 25.5 D, or with a ΔP of 4.0 D.

An azimuthal power distribution (such as described herein, for example, or otherwise) can be implemented for 0≤θ<2π−α, where α is a small angle within a range of angles (e.g., between a minimum and a maximum angle, one or more of which may be determined or identified depending upon design/implementation particulars, required optical properties, manufacturing procedures and materials involved, and other factors). Accordingly, it is envisioned that in example embodiments an azimuthal power distribution is implemented for $0 \leq \theta < 2\pi - \alpha$, where $\alpha$ is an angle having a value (such as 30°, 18°, or 10°). It is envisioned that in example embodiments an azimuthal power distribution is implemented for $0 \leq 0 < 2\pi - \alpha$, where $\alpha$ is a nonzero angle, within a range of angles. For instance, in example embodiments, an azimuthal power distribution is implemented for $0 \leq \theta < 2\pi - \alpha$, where $\alpha$ is an angle within a range of angles (for example, $0° < \alpha \leq 30°$).

Optical Properties of Vortex IOL in a Hypothetical Model Eye

Before further analyzing the optical properties of this new vortex IOL design, an exemplary ocular system with an IOL in it will be described.

A hypothetical model eye having optical properties that are similar to the average human eye (e.g., corneal shape and on-axis performance) may be used to evaluate in-situ performance of the vortex IOL design or any other optics designs, with the 21.5 D spherical IOL replacing the crystalline lens. One suitable model eye is the Liou and Brennan model eye (H. L. Liou and N. A. Brennan, "Anatomically accurate, finite model eye for optical modeling," *J. Opt. Soc. Am. A, Opt. Image Sci. Vis.*, 14, 1684-1695 (1997)) described in Table 1. Note that the focal plane was calculated at marginal ray height or the ray that travels from the center of the object, the pupil semi-diameter may be varied, and all values shown were rounded to two decimal places, except for the refractive indices.

TABLE 1

Optical surface data for Liou-Brennan model eye with IOL.

| Surface | Comment | Radius | Thickness | Glass | Semi-Diameter | Conic |
|---|---|---|---|---|---|---|
| OBJ | Object | Infinity | Infinity | — | 0.00 | 0.00 |
| 1 | Anterior cornea | 7.77 | 0.50 | 1.376 | 6.00 | −0.18 |
| 2 | Posterior cornea | 6.40 | 3.16 | 1.336 | 6.00 | −0.60 |
| STO | Pupil | Infinity | 1.34 | 1.336 | 1.50 | 0.00 |
| 4 | Anterior IOL | 18.40 | 0.64 | 1.544 | 3.00 | 0.00 |
| 5 | Posterior IOL | −20.30 | 18.19 | 1.336 | 3.00 | 0.00 |
| IMA | Image plane | −8.10 | — | — | — | — |

The optical performance discussed below were obtained using the ZEMAX® optical design program (ZEMAX Development Corporation). The refractive indices for optical components were chosen for e-ray (0.546074 μm of wavelength). The wavefront data from ZEMAX then send to MATLAB program for wavefront modulation. Then, the optical properties are analyzed by modulating the transmittance of Fourier optics modulated by a light amplitude distribution equals to $\exp(-0.122\ r^2)$ corresponding to the Stiles-Crawford effect (N. Singh, "*Variation of the Stiles-Crawford effect with accommodation and myopia*," Ph.D. Thesis, School of Optometry, Institute of Health and Biomedical Innovation, Queensland Univ. Tech., Ch. 2 (2009)).

Vortex IOL Design

Suitable material for the Vortex IOL includes, but is not limited to, HOYA material A, which is a hydrophobic acrylic material (U.S. Pat. No. 7,714,090) and the discussion herein (where appropriate) assumes the use of this material. Other suitable materials include, but are not limited to, PMMA and other silicone or acrylic materials, which are appropriate for IOL.

A spherical IOL with 21.5 D refractive power is designed with a 0.17 mm edge thickness at 6.0 mm diameter. The material of this IOL is HOYA material A, which has 1.544 refractive index at e-ray of wavelength and at 35 Celsius degrees temperature. The refractive index of the aqueous humour used for calculation is 1.336. The posterior radius of curvature is fixed at −20.30 mm and the anterior radius of curvature is then calculated using Eq. 2. For the aspheric portion of the design, the posterior apex radius is fixed and the 4-th and 6-th order aspheric coefficients are optimized to meet the aberration requirement, i.e., to compensate the corneal spherical aberration such that no spherical aberration in the ocular system is used for the design. The obtained design parameters for anterior radius, posterior radius, center thickness, and the asphericity are summarized in Table 2.

TABLE 2

IOL optical design parameters.

| Type of IOL | Anterior Radius (mm) | Posterior Radius (mm) | Center Thickness (mm) | Posterior Aspheric Coefficients | |
|---|---|---|---|---|---|
| | | | | 4-th order | 6-th order |
| Spherical | 18.40 | −20.30 | 0.64 | 0 | 0 |
| Aspheric | 18.40 | −20.30 | 0.64 | 5.905646574071e−4 | −2.958988365971e−6 |

$\Delta P$ of 3.0 and 4.0 D vortex IOL design as well as modified vortex IOL design both with surface step reduction of $\alpha=9°$ will be used for numerical analysis. In order to compare the performance of the vortex IOL designs, the Strehl ratio, defocus response, and imaging properties of a set of Landolt C optotypes are chosen.

Simulation Results

A Strehl ratio is a measure of the quality of optical image formation, originally proposed by Karl Strehl (1864-1940) after whom the term is named. It is used variously in situations where optical resolution is compromised due to lens aberrations or due to imaging through the turbulent atmosphere, the Strehl ratio has a value between 0 and 1, with a "perfect" (unaberrated) optical system attaining the value of unity.

In a recent study, Thibos et al. proposed visual Strehl ratio as an optical metric that is an integration of inner product of the PSF with a neural weighting function normalized to the diffraction-limited case. See L. N. Thibos, X. Hong, A. Bradley, R. A. Applegate, "Accuracy and precision of objective refraction from wavefront aberrations," *J. Vision*, 4, 329-351 (2004). The visual Strehl ratio can be expressed as $$VSR = \frac{\iint_{PSF} PSF(x,y)N(x,y)dxdy}{\iint_{PSF} PSF_{DL}(x,y)N(x,y)dxdy}, \quad (7)$$

where N(x,y) is a bivariate neural weighting function equal to the inverse Fourier transform of the neural contrast sensitivity function for the interference fringes proposed by Champbell and Green. See F. W. Campbell and D. G. Green, "Optical and retinal factors affecting visual resolution," *J. Physiol.* 181, 576-593 (1965). Mannos and Sakrison proposed an analytical model of the contrast sensitivity function (CSF) as the following equation.

$$CSF=2.6(0.0192+0.114f)\exp[-(0.114f)^{1.1}], \quad (8)$$

where f is the spatial frequency in cycles per degree. See J. L. Mannos and D. J. Sakrison, "The effects of a visual fidelity criterion on the encoding of images," *IEEE Trans. Inform. Theory,* 20, 525-535 (1974). This serves as an approximation based on observers' judgments of images and will be used to calculate the visual Strehl ratio and other optical properties.

FIGS. 7A and 7B and FIGS. 8A and 8B are the visual Strehl ratio map results for spherical and aspheric vortex IOL design, respectively, with ΔP=3.0 D. Left figure plots the visual Strehl ratio as a function of defocus and pupil size in 2D map and right figure includes also the contour lines with 2D map similar to the left figure. The contour lines have 3 colors. The upper (green colored) contour lines represent the visual Strehl ratio with values of 0.2, 0.4, 0.6, and 0.8 (denoted thereon), the intermediate (yellow colored) contour lines represent the visual Strehl ratio with values of 0.12 and 0.15 (denoted thereon) and the lower (red colored) contour lines represent the visual Strehl ratio with value of 0.08 and 0.10 (denoted thereon). The areas within the upper (green) and intermediate (yellow) contour lines represent as good and moderate image formation, whereas the areas within the lower (red) contour lines represent as poor image formation. FIGS. 9A and 9B and FIGS. 10A and 10B are the visual Strehl ratio map results for spherical and aspheric modified vortex IOL design, respectively, with ΔP=3.0 D. FIGS. 11A-14B are similar and correspond to FIGS. 7A-10B, respectively, except with ΔP=4.0 D instead of 3.0 D.

The visual defocus response results for the situations of FIGS. 7A-14B are shown in FIGS. 15A-22B, respectively. Left figures (FIGS. 15A, 16A, 17A, 18A, 19A, 20A, 21A and 22A) show plots of the visual defocus response calculated at 3.0 mm pupil size and right figures (FIGS. 15B, 16B, 17B, 18B, 19B, 20B, 21B and 22B) show plots at 4.5 mm pupil size.

Figure 23:
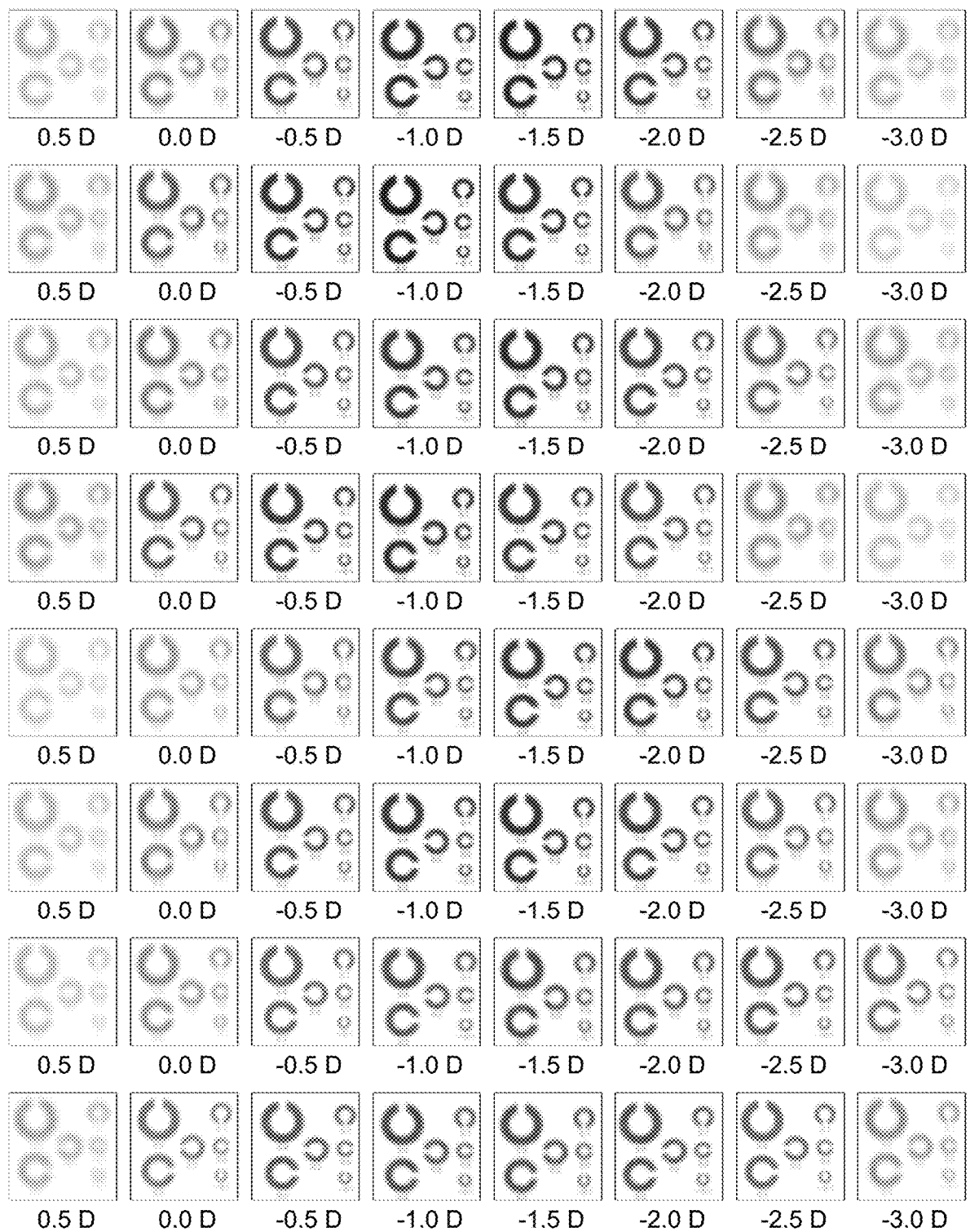
FIG. 23 shows Landolt C visual images for vortex IOLs at 3.0 mm pupil size. The first four images from the top are spherical, aspheric, modified spherical, and modified aspheric with ΔP=3.0 D. The next four images continuing downward are spherical, aspheric, modified spherical, and modified aspheric with ΔP=4.0 D.
Figure 24:
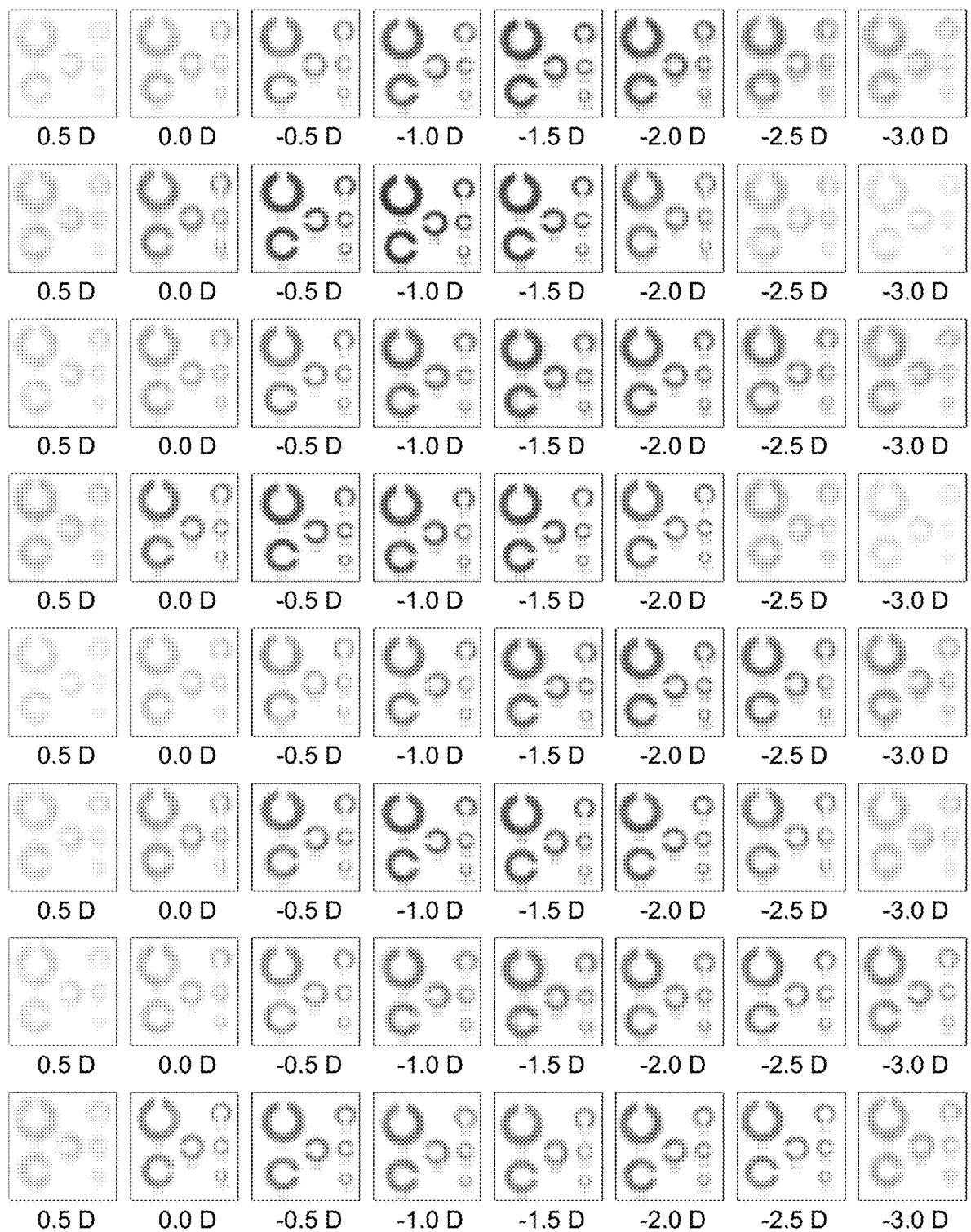
FIG. 24 shows Landolt C visual images for vortex IOLs at 4.5 mm pupil size. The first four images from the top are spherical, aspheric, modified spherical, and modified aspheric with ΔP=3.0 D. The next four images continuing downward are spherical, aspheric, modified spherical, and modified aspheric with ΔP=4.0 D.

FIGS. 23 and 24 show the vortex IOL Landolt C visual images obtained for the situations of FIGS. 7A-14B, at 3.0 mm and 4.5 mm pupil sizes, respectively. For each figure, the first four images from the top are spherical, aspheric, modified spherical, and modified aspheric with ΔP=3.0 D, and the next four images continuing downward are spherical, aspheric, modified spherical, and modified aspheric with ΔP=4.0 D. The smallest and the biggest "C" represent −0.1 and 0.4 LogMAR visual acuity.

These results show that the vortex IOL design offers a wide depth of focus at an acceptable imaging level (e.g., providing total visual depth of focus (DOF) for the optical device of about 2.0 D to 3.0 D, with DOF being the dioptric range for which the visual Strehl ratio of the optical device is greater than 0.12 at 3 mm pupil size diameter).

Prototypes and Experimental Results

In order to verify the vortex IOL design, prototypes of both vortex and modified vortex IOL design were manufactured, including prototypes made from PMMA material and implementing an aspheric portion to compensate the spherical aberrations such that there is no spherical aberration in the lens itself at 21.5 D. The design parameters are summarized in Table 3.

TABLE 3

IOL optical design parameters for protoyping.

| Type of IOL | Anterior Radius (mm) | Posterior Radius (mm) | Center Thickness (mm) | Posterior Aspheric Coefficients | |
|---|---|---|---|---|---|
| | | | | 4-th order | 6-th order |
| Aspheric | 14.43 | −14.70 | 0.79 | 1.06085968624e−4 | 8.175315662629e−8 |

Manufacturing the Prototypes

Figure 25A:
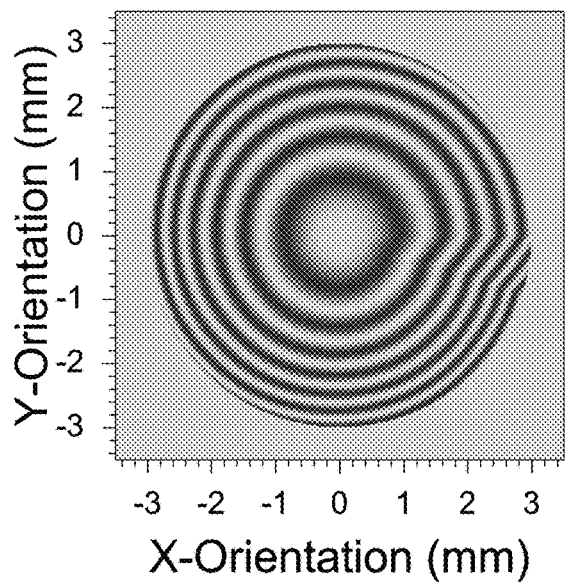
FIGS. 25A and 25B are the surface sag maps for vortex IOL and modified vortex IOL, respectively, of the ΔP of 4.0 D vortex surfaces with surface step reduction of α=18°.
Figure 25B:
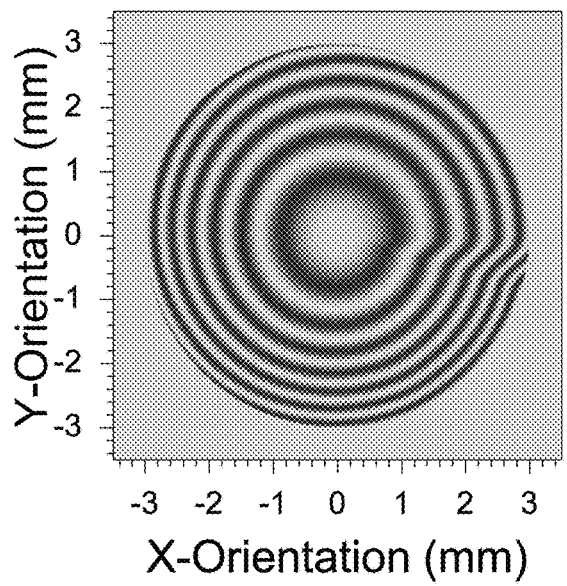
Figure 26A:
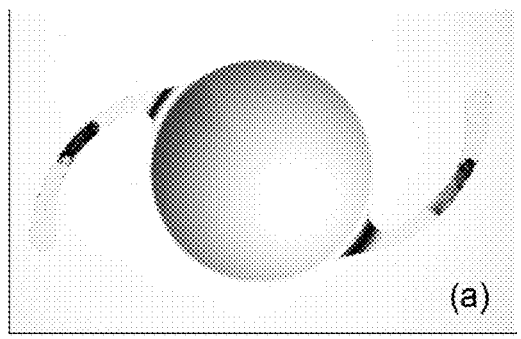
FIGS. 26A and 26B are photographs of the prototypes of vortex IOL and modified vortex IOL, respectively.
Figure 26B:
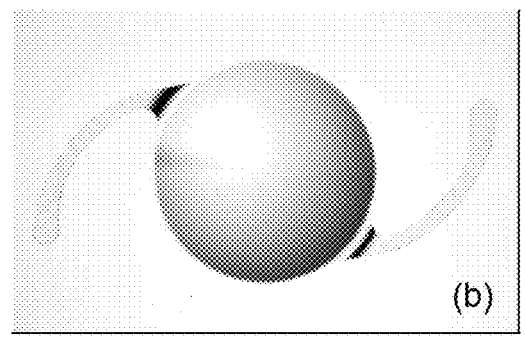

The prototypes were manufactured (machined with a lathe cut machine) for ΔP of 4.0 D vortex as well as modified vortex IOL designs both with surface step reduction of α=18°. The machining of these prototypes was done at HOYA Medical Singapore, Pte. Ltd., Singapore. The parameters for controlling the machine were 100 rpm speed and 1 mm per minute feed rate for optics part and 300 rpm speed and 8 mm per minute feed rate for haptics. FIGS. 25A and 25B are the surface sag maps for vortex IOL and modified vortex IOL, respectively, of the ΔP of 4.0 D vortex surfaces with surface step reduction of α=18°. FIGS. 26A and 26B show photographs of fabricated prototypes of vortex IOL and modified vortex IOL, respectively.

Test Facility

The measurements of these tests were performed at the HOYA Corporation Medical Division, Tokyo, Japan.

Test Instrument/Apparatus and Procedures

The instruments and apparatus used by these tests were as follows:

| | | |
|---|---|---|
| IOL Lens Mapper | Lambda-X NIMO TR0815 | (TT-056-001) |
| IOL Automatic Measurement System | Trioptics Optispheric IOL | (TT-064-001) |
| ISO Model Eye | Trioptics Model Eye | (TT-067-001) |
| Apertures for ISO Model Eye | Trioptics Apertures | 3.0 mm and 4.5 mm |
| HOYA Imaging System | HOYA in-house production | |
| Apertures for Imaging System | HOYA in-house production | 3.0 mm and 4.5 mm |

The tests were performed immersed in distilled water based on the ISO International Standard: ISO11979-2:2006 (E). The test methods utilized (procedure, equipment, conditions of test, etc.) are specified in the HOYA Testing Work Instruction WIDS/AB Ver. 4.1 and NIMO TR0815 Intraocular Lens Mapper Software User guide Ver. 4.8.3.

Test Results

Figure 27A:
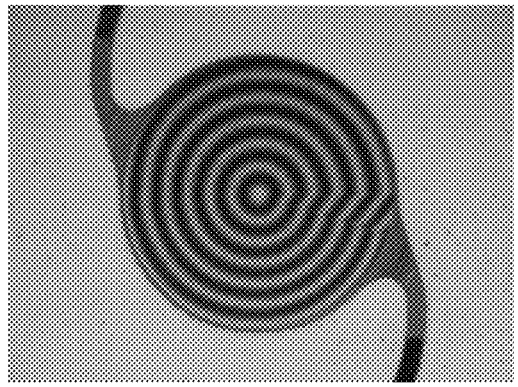
FIGS. 27A and 27B show the Schlieren fringes of the fabricated vortex IOLs.
Figure 27B:
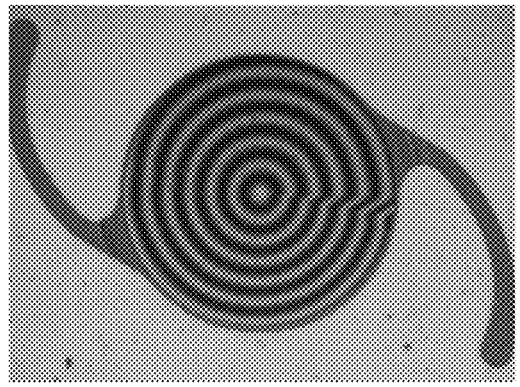
Figure 28A:
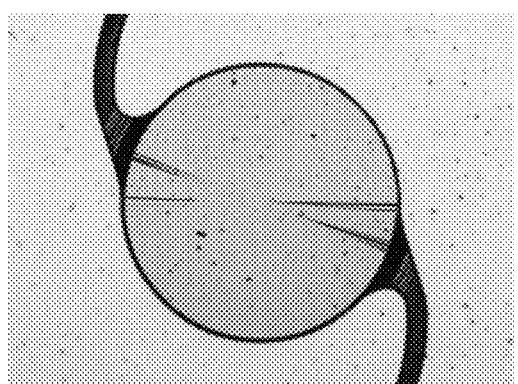
FIGS. 28A and 28B show the modulation maps of the fabricated vortex IOLs.
Figure 28B:
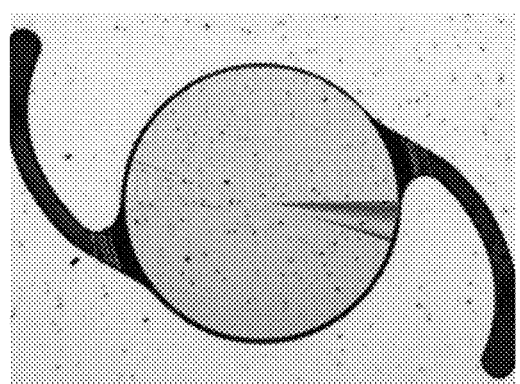

The Lambda-X NIMO TR0815 high resolution power mapper and wavefront analyser was used for mapping the power of vortex IOLs. The NIMO TR0815 measures lenses based on a quantitative deflectometry technique combining the principles of Schlieren and the phase-shifting, allowing to measure light beam deviations with great accuracy and precision. Also, the lens under test is imaged on a high resolution camera providing NIMO TR0815 an ability to visualize the local defects on the lens. FIGS. 27A and 27B show the Schlieren fringes (representing light beam deviations) of vortex and modified vortex IOLs, respectively. These maps were similar to those shown in FIGS. 25A and 25B. The modulation maps of these fabricated IOLs are shown in FIGS. 28A and 28B, where manufacturing errors for both IOLs are detected in the modulation map site corresponding to the surface step. The manufacturing errors of modified vortex IOL were less compared to those of vortex IOL, the optical device implementing methodology described herein entirely or substantially eliminating any discontinuity along the azimuthal power distribution of the modified vortex IOL.

Figure 29A:
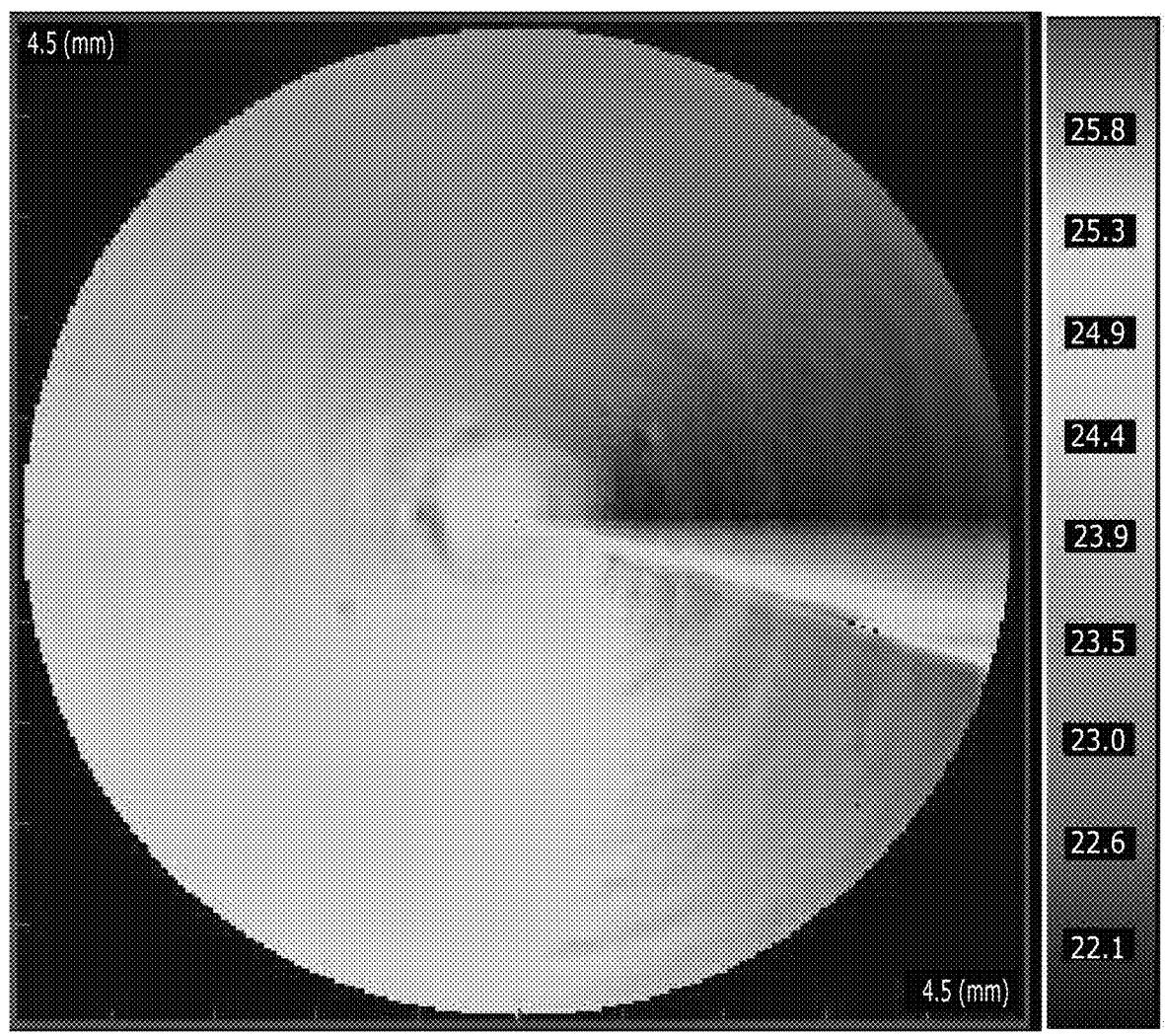
FIGS. 29A and 29B show the power maps of the ΔP of 4.0 D of the fabricated vortex IOLs.
Figure 29B:
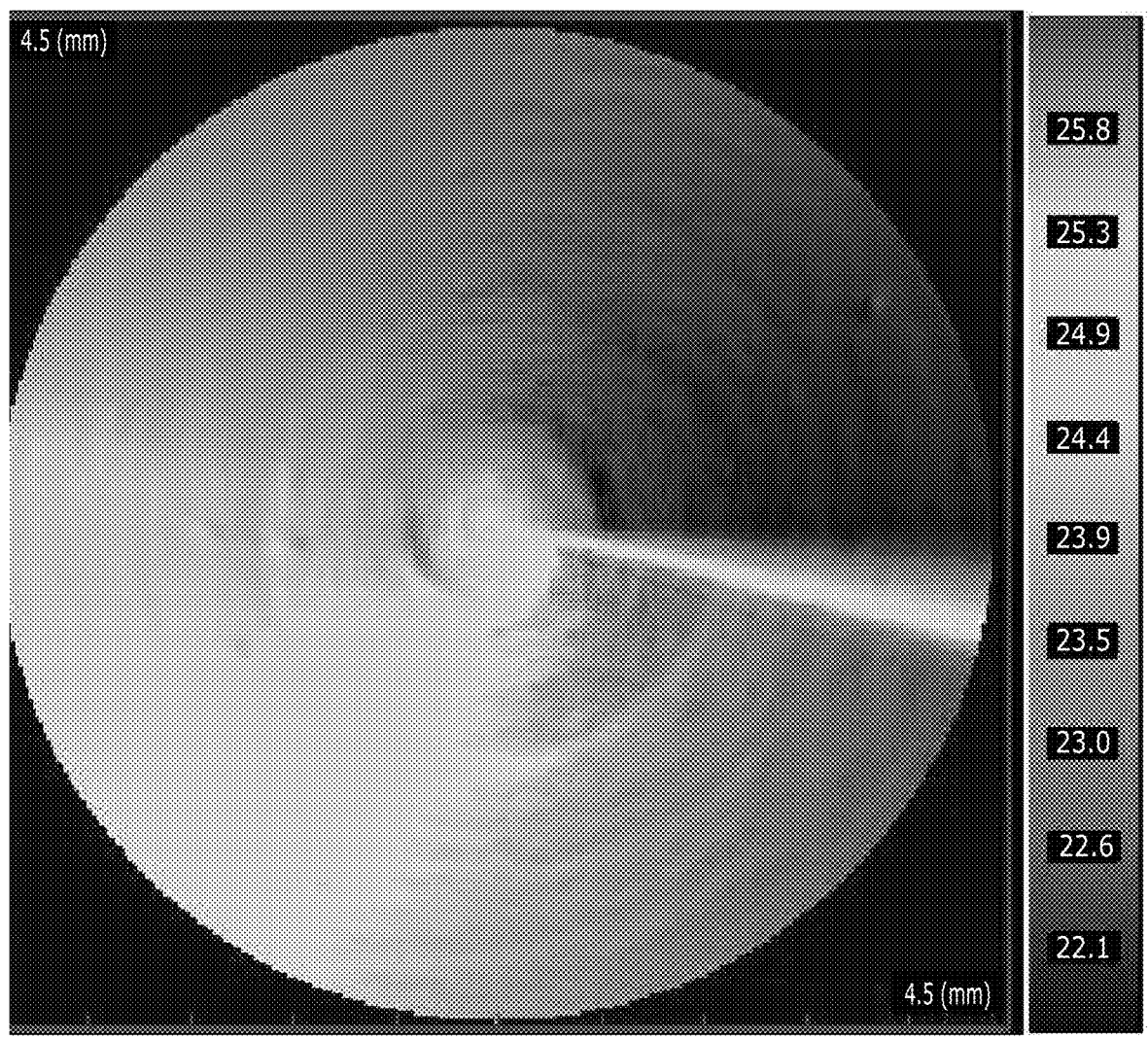

FIGS. 29A and 29B show the power maps of the ΔP of 4.0 D of the fabricated vortex and modified vortex IOL, respectively. As the measurements were taken with the IOLs immersed in distilled water, then, theoretically, the IOLs power will be spread from 21.91 D to 25.98 D. Although the IOLs were not perfectly manufactured, the power distributions (FIGS. 29A and 29B) of the fabricated IOLs were similar to the theoretical values.

Figure 30A:
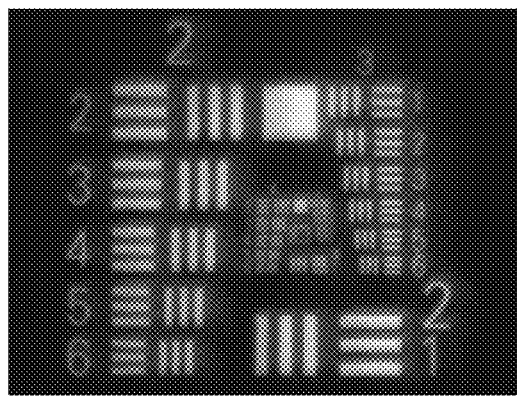
FIGS. 30A and 30B show USAF Target images of the fabricated vortex IOLs in the ISO model eye at 3.0 mm pupil size.
Figure 30B:
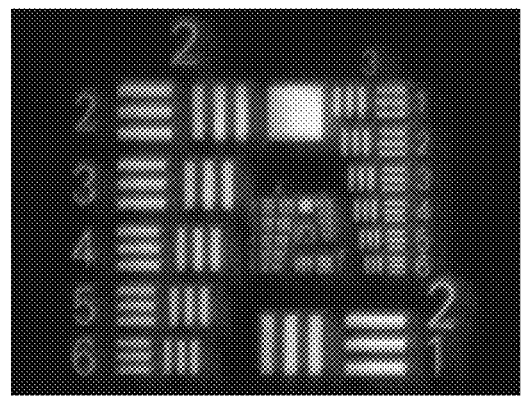
Figure 31A:
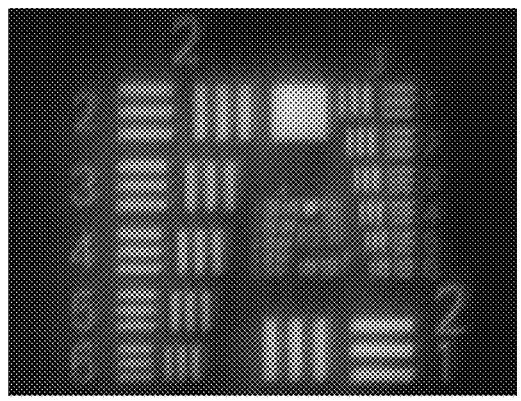
FIGS. 31A and 31B show USAF Target images of the fabricated vortex IOLs in the ISO model eye at 4.5 mm pupil size.
Figure 31B:
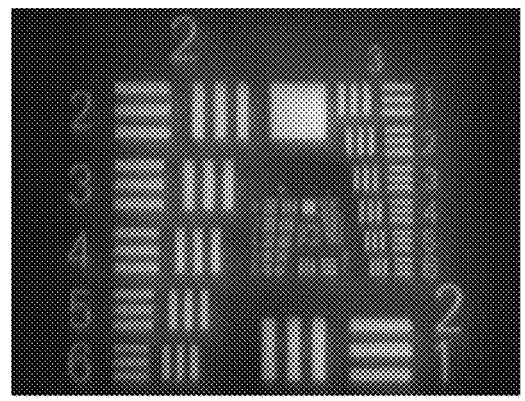

The USAF target images were investigated using Trioptics Optispheric IOL. FIGS. 30A and 30B and FIGS. 31A and 31B show USAF Target images of the fabricated vortex IOLs in the ISO model eye at 3.0 mm and 4.5 mm pupil sizes, respectively. FIGS. 30A and 31A show the USAF images for a vortex IOL. FIGS. 30B and 31B show the USAF images for a modified vortex IOL.

Referring to FIGS. 30A and 30B, at the smaller pupil size (3.0 mm), the USAF target images have acceptable resolution for a visual system. However, when the pupil size is larger (4.5 mm) the image obtained with the fabricated vortex IOL (in FIG. 31A) was deteriorated, while the image with the modified vortex IOL (in FIG. 31B) was good. The cause of this deterioration was due to the error in fabrication of the vortex IOL, such error being mainly attributable to instability of the lathe cut machine used for fabrication, and the effect (image deterioration) could be emphasized at larger pupil sizes.

Figure 32:
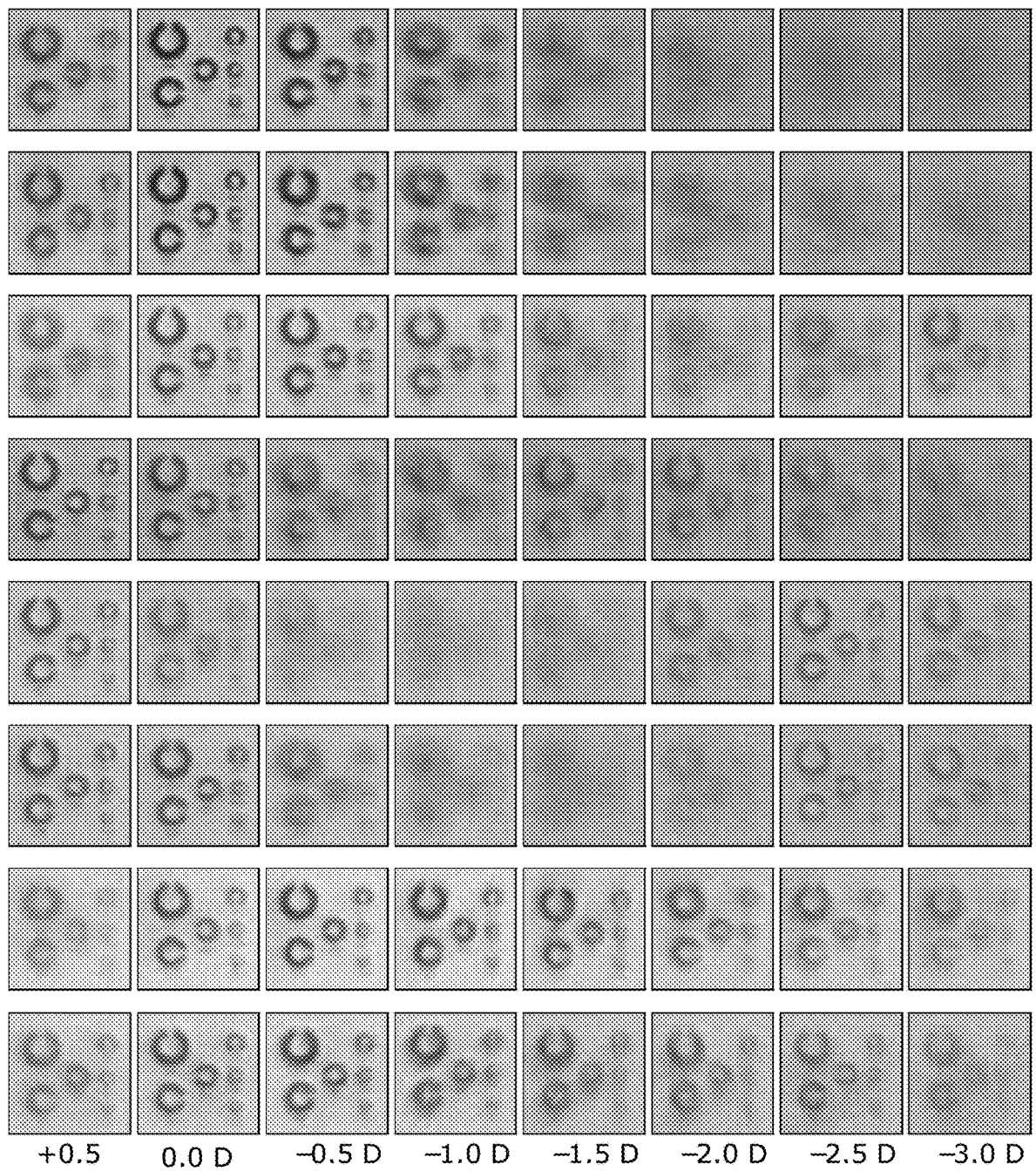
FIG. 32 shows Landolt C images for eight different IOLs at 3.0 mm pupil size. The IOLs from top to bottom are: 1. A typical spherical IOL, 2. HOYA extended depth of focus IOL (751 model), 3. AMO refractive multifocal IOL (NXG1), 4. Topcon MPlus refractive sector multifocal IOL (LS-312), 5. AMO Tecnis diffractive multifocal IOL (ZMA00), 6. Alcon ReSTOR apodized diffractive multifocal IOL (SA60D3), 7. Prototype of vortex IOL, and 8. Prototype of modified vortex IOL. The dioptric power of all IOLs were 20.0 D, except 21.5 D for vortex IOLs.
Figure 33:
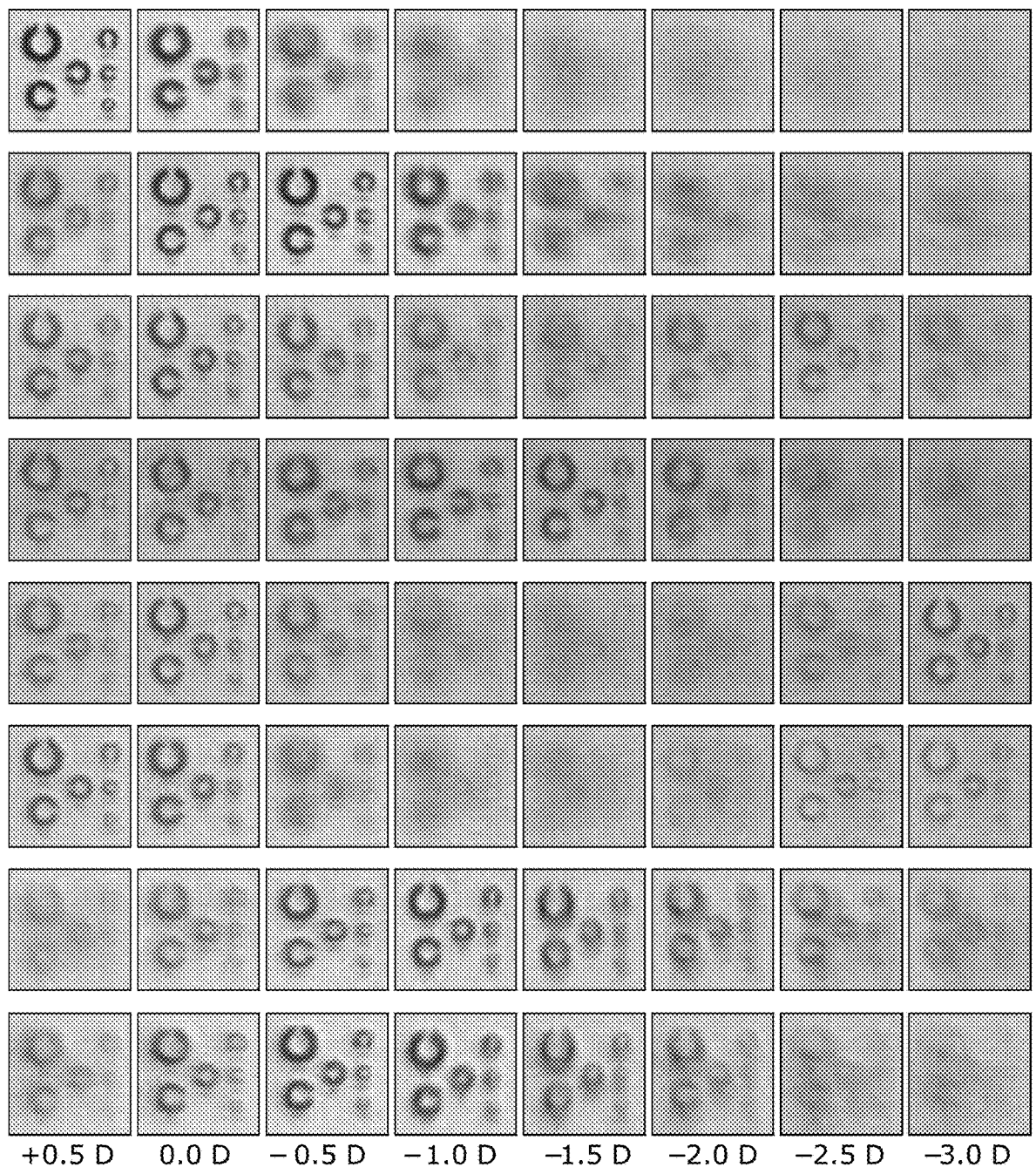
FIG. 33 shows Landolt C images for eight different IOLs at 3.0 mm pupil size with 0.5 mm IOL decentration. The IOLs from top to bottom are: 1. A typical spherical IOL, 2. HOYA extended depth of focus IOL (751 model), 3. AMO refractive multifocal IOL (NXG1), 4. Topcon MPlus refractive sector multifocal IOL (LS-312), 5. AMO Tecnis diffractive multifocal IOL (ZMA00), 6. Alcon ReSTOR apodized diffractive multifocal IOL (SA60D3), 7. Prototype of vortex IOL, and 8. Prototype of modified vortex IOL.
Figure 34:
FIG. 34 shows Landolt C images for eight different IOLs at 3.0 mm pupil size with corneal astigmatism of 1.0 D. The IOLs from top to bottom are: 1. A typical spherical IOL, 2. HOYA extended depth of focus IOL (751 model), 3. AMO refractive multifocal IOL (NXG1), 4. Topcon MPlus refractive sector multifocal IOL (LS-312), 5. AMO Tecnis diffractive multifocal IOL (ZMA00), 6. Alcon ReSTOR apodized diffractive multifocal IOL (SA60D3), 7. Prototype of vortex IOL, and 8. Prototype of modified vortex IOL.
Figure 35:
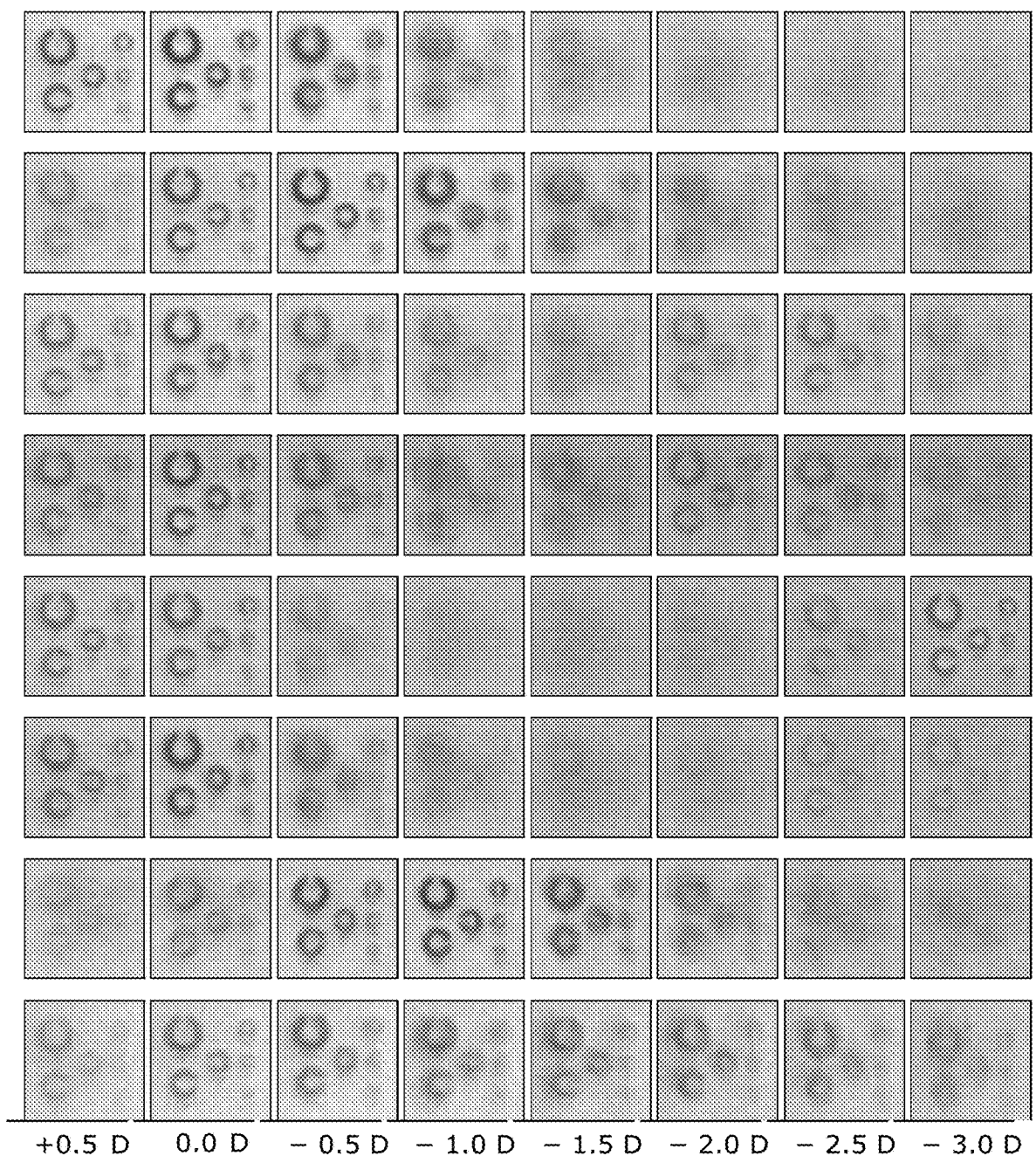
FIG. 35 shows Landolt C images for eight different IOLs at 4.5 mm pupil size. The IOLs from top to bottom are: 1. A typical spherical IOL, 2. HOYA extended depth of focus IOL (751 model), 3. AMO refractive multifocal IOL (NXG1), 4. Topcon MPlus refractive sector multifocal IOL (LS-312), 5. AMO Tecnis diffractive multifocal IOL (ZMA00), 6. Alcon ReSTOR apodized diffractive multifocal IOL (SA60D3), 7. Prototype of vortex IOL, and 8. Prototype of modified vortex IOL.
Figure 36:
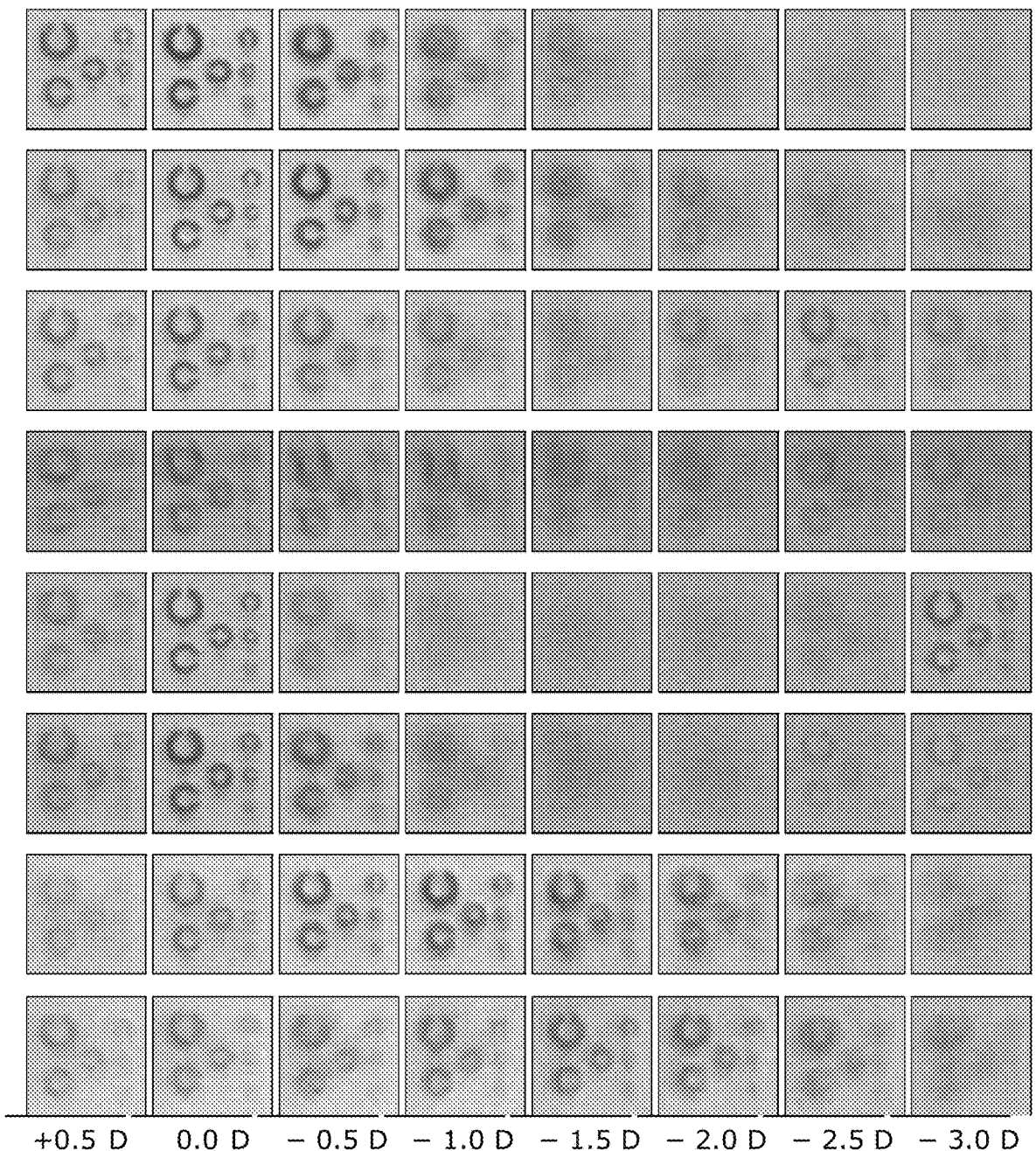
FIG. 36 shows Landolt C images for eight different IOLs at 4.5 mm pupil size with 0.5 mm IOL decentration. The IOLs from top to bottom are: 1. A typical spherical IOL, 2. HOYA extended depth of focus IOL (751 model), 3. AMO refractive multifocal IOL (NXG1), 4. Topcon MPlus refractive sector multifocal IOL (LS-312), 5. AMO Tecnis diffractive multifocal IOL (ZMA00), 6. Alcon ReSTOR apodized diffractive multifocal IOL (SA60D3), 7. Prototype of vortex IOL, and 8. Prototype of modified vortex IOL.
Figure 37:
FIG. 37 shows Landolt C images for eight different IOLs at 4.5 mm pupil size with corneal astigmatism of 1.0 D. The IOLs from top to bottom are: 1. A typical spherical IOL, 2. HOYA extended depth of focus IOL (751 model), 3. AMO refractive multifocal IOL (NXG1), 4. Topcon MPlus refractive sector multifocal IOL (LS-312), 5. AMO Tecnis diffractive multifocal IOL (ZMA00), 6. Alcon ReSTOR apodized diffractive multifocal IOL (SA60D3), 7. Prototype of vortex IOL, and 8. Prototype of modified vortex IOL.

FIGS. 32-37 show the Landolt C images for eight different IOLs, listed the figure captions below the figures. In each of these figures, the IOLs from top to bottom are: 1. A typical spherical IOL, 2. HOYA extended depth of focus IOL (751 model), 3. AMO refractive multifocal IOL (NXG1), 4. Topcon MPlus refractive sector multifocal IOL (LS-312), 5. AMO Tecnis diffractive multifocal IOL (ZMA00), 6. Alcon ReSTOR apodized diffractive multifocal IOL (SA60D3), 7. Prototype of vortex IOL, and 8. Prototype of modified vortex IOL. The dioptric power of all IOLs were 20.0 D, except 21.5 D for vortex IOLs. FIGS. 32, 33 and 34 show Landolt C images for the eight different IOLs at 3.0 mm pupil size, at 3.0 mm pupil size with 0.5 mm IOL decentration, and at 3.0 mm pupil size with corneal astigmatism of 1.0 D, respectively. FIGS. 35, 36 and 37 show Landolt C images for the eight different IOLs at 4.5 mm pupil size, at 4.5 mm pupil size with 0.5 mm IOL decentration, and at 4.5 mm pupil size with corneal astigmatism of 1.0 D, respectively. At the optical axis (FIGS. 32 and 35), both vortex and modified vortex were superior compared to other IOL types at 3.0 mm, as well as at 4.5 mm pupil size and they coincide well with the numerical simulations. The 0.5 mm IOL decentration (FIGS. 33 and 36) did not significantly affect the Landolt C images. When a 1.0 D cylinder lens was used to simulate corneal astigmatism (FIGS. 34 and 37), deteriorated images were the result (as would be expected) for all of the IOLs, especially in the multifocal IOL designs. However, for both the vortex and modified vortex IOLs, the effects of corneal astigmatism on their corresponding images were similar or even better compared to the typical spherical IOL. These results show a great benefit of this vortex design for cataract surgery.

Figure 38:
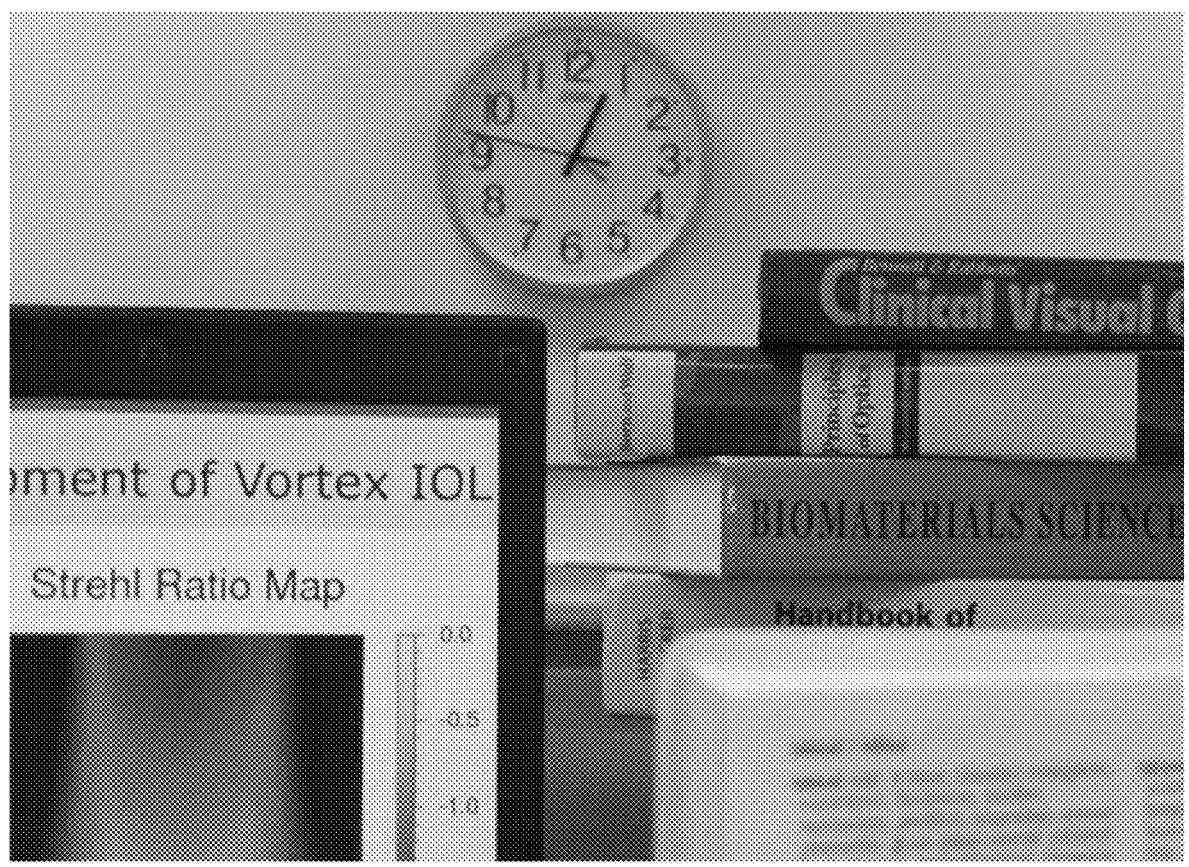
FIG. 38 is a photograph of the 3D scene (used in the experiment) consisting of objects located at different distances. A clock at 4 m, books at 1 m, a laptop PC's monitor at 60 cm, and an opened thesaurus at 30 cm are used for objects.
Figure 40:
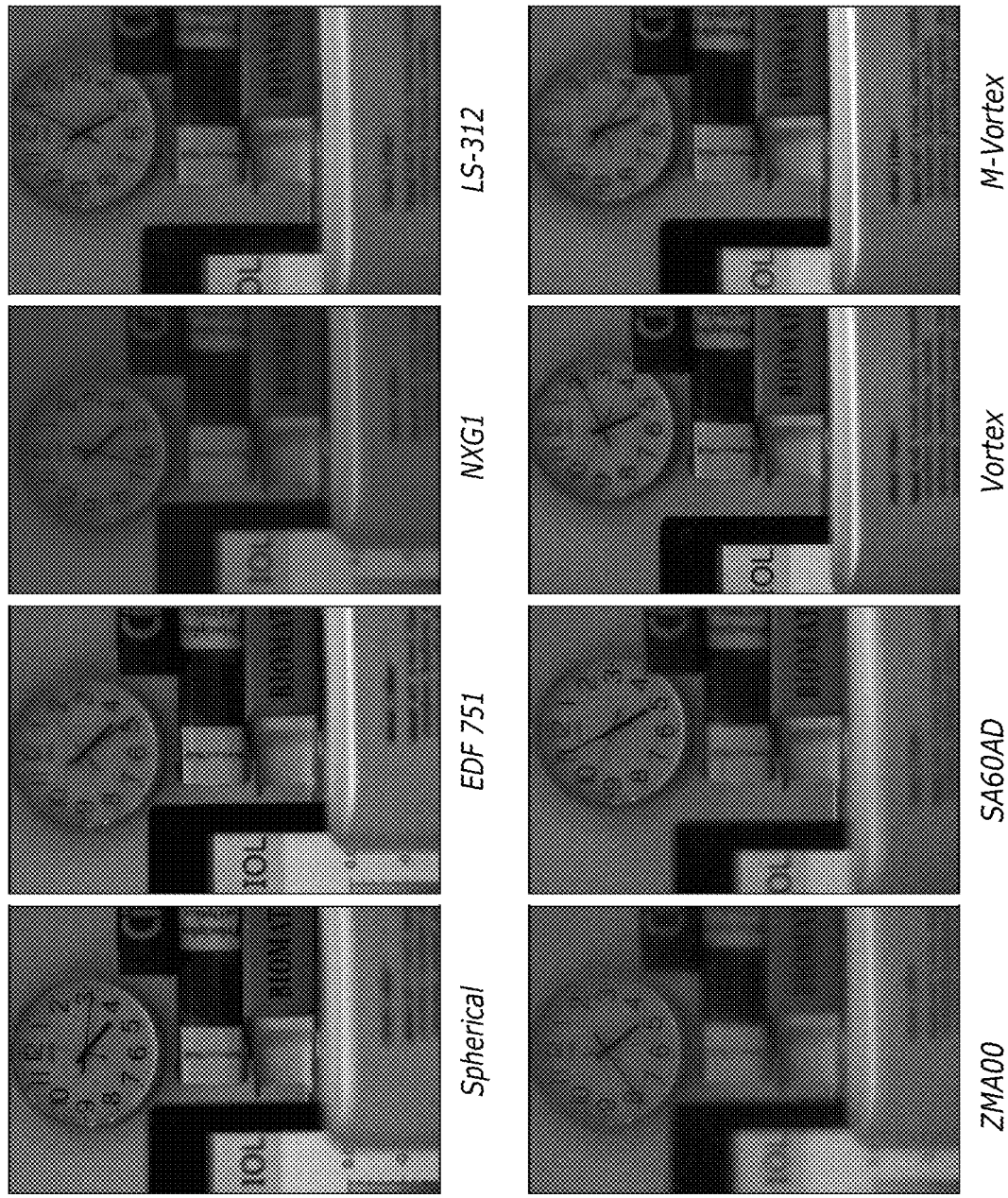
FIG. 40 shows 3D scene images for eight different IOLs at 4.5 mm pupil size.

For a more easy understanding, the Landolt C optotypes were changed with a 3D scene consisting of objects located at different distances. FIG. 38 shows the photograph of the scene consisting of a clock at 4 m, books at 1 m, a laptop PC's monitor at 60 cm, and an opened thesaurus at 30 cm. Even a quality digital camera typically cannot (simultaneously obtain) focus at all objects (that is, at all object depths or distances in relation to the focal plane). The clock and especially the thesaurus are out of focus. FIG. 39 shows 3D scene images (taken under this setting) for eight different IOLs at 3.0 mm pupil size. FIG. 40 shows 3D scene images (taken under this setting) for eight different IOLs at 4.5 mm pupil size. Again, these results show the wide depth of focus visual range superiority of both vortex and modified vortex IOLs compared to the typical spherical IOL.

With respect to the "modified" vortex IOLs themselves, and as discussed above, the vortex IOLs of the present invention(s) improve depth of focus by controlling the amount of spherical aberrations of the eye. One such vortex IOL, which is identified by reference numeral 100 in FIG. 41, has a lens body 110 including an anterior lens surface (or portion) 112 and a posterior lens surface (or portion) 113 implemented as described herein. The IOL 100 is shown as part of an optical system that also includes an eye 140 with a cornea 160 and retina 180. Haptics (not shown in this figure) may also be provided.

In example embodiments and implementations, the IOL 100 is composed of entirely refractive optical element(s) implementing an angular modulation of a transmittance of said lens. For example, the anterior lens surface (or portion) 112 includes spiral or helical structure implemented as described herein to control the refractive foci of incident light.

In example embodiments and implementations, the lens body 110 is (or includes) an entirely refractive (true) multifocal optical element (e.g., implemented as described herein). The posterior lens surface (or portion) 113 can be spherical or, alternatively or in addition, aspheric.

Figure 43B:
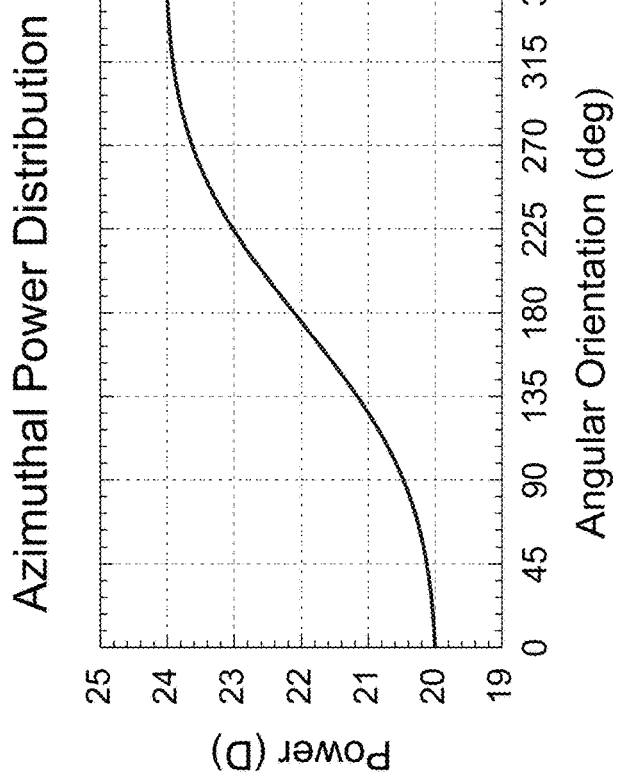
FIGS. 43A and 43B show the optical power distribution for another example modified vortex IOL with surface step reduction of $\alpha=10°$ according to the IOL power stretched from 20.0 D to 24.0 D using an error function with $\alpha=0.3$.
Figure 43A:
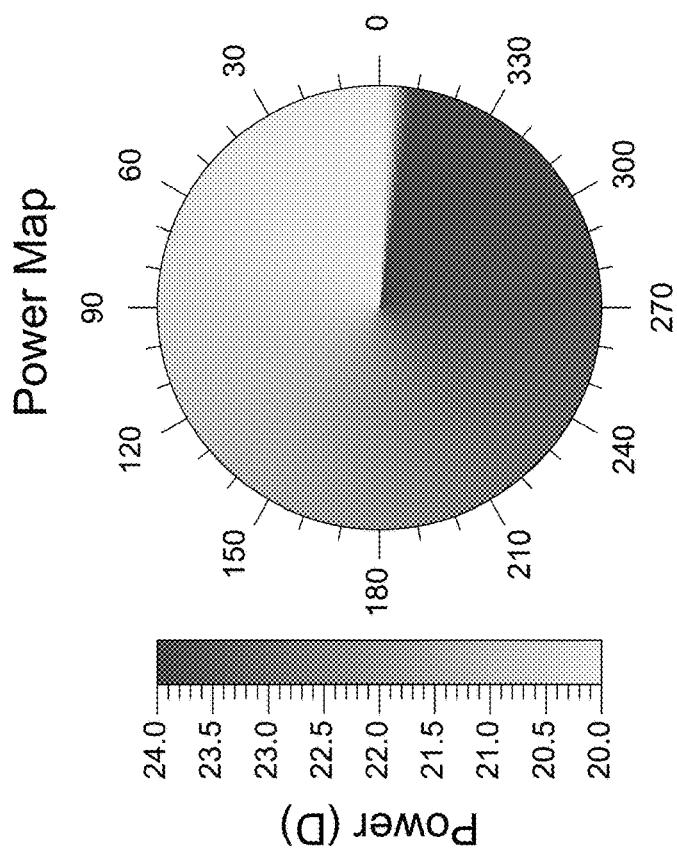
Figures 44A, 44B:
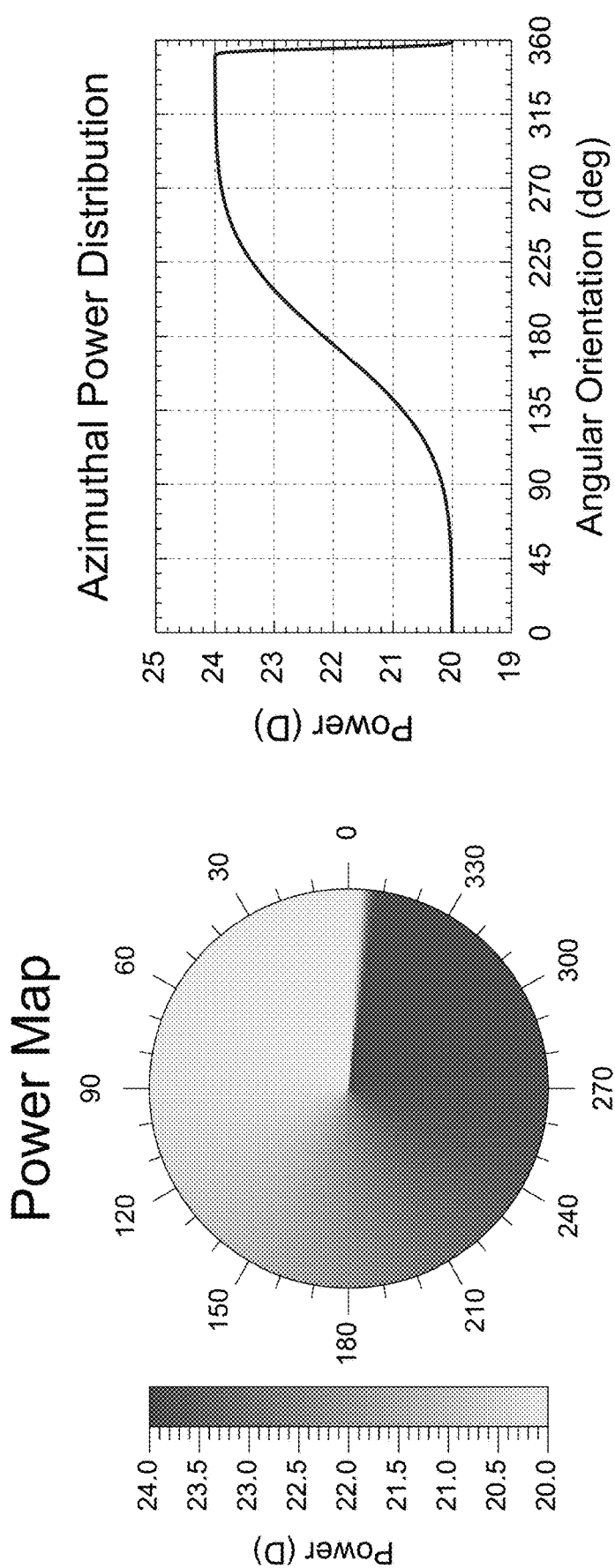
FIGS. 44A and 44B show the optical power distribution for another example modified vortex IOL with surface step reduction of $\alpha=10°$ according to the IOL power stretched from 20.0 D to 24.0 D using an error function with $\alpha=0.2$.

Modified vortex IOLs of various optical designs have been implemented and tested. Vortex IOLs referred to herein as Vortex model 1 and model 2 lenses were designed with surface step reduction of 10° and based on an error function with $\sigma=0.3$ and $0.2$, respectively. Both models were with 4.0 D power stretched ($\Delta P$). The azimuthal power distribution is a function of $\sigma$. Higher $\sigma$ value will result in the azimuthal power distribution to approach a linear change, and conversely, lower $\sigma$ value will result in the azimuthal power distribution to approach a step change. In this example implementation, $\sigma=0.3$ produces a sinusoidal like azimuthal power distribution, and $\sigma=0.2$ an azimuthal power distribution more in lower and higher powers (i.e., predominantly/principally implementing lower and higher power vision zones). FIGS. 43A and 43B show the optical power distribution (power map distribution and azimuthal plot, respectively) for the first example (Vortex model 1) type with surface step reduction of $\sigma=10°$ according to the IOL power stretched from 20.0 D to 24.0 D using an error function with $\sigma=0.3$. FIGS. 44A and 44B show the optical power distribution (power map distribution and azimuthal plot, respectively) for the other example (Vortex model 2) type with surface step reduction of σ=10° according to the IOL power stretched from 20.0 D to 24.0 D using an error function with σ=0.2. Power is constant in the radial direction as is indicated by the lack of change in color in the radial direction for each radial direction in FIG. 44A. For the aspheric portion of the design, the posterior apex radius is fixed and the 4-th and 6-th order aspheric coefficients are optimized to meet the aberration requirement, i.e. to compensate the corneal spherical aberration (about 0.12 μm at 6 mm entrance pupil) such that no spherical aberration in the ocular system is used for the design. The lenses were fabricated from PMMA material with spherical or plane on anterior surface and vortex aspheric on posterior surface. The obtained design parameters for shape factor, anterior radius, posterior radius and its aspheric coefficients, center thickness, and edge thickness are summarized in Table 4.

TABLE 4

Optical design parameters for both Vortex Model 1 (σ = 0.3) and Vortex Model 2 (σ = 0.2).

| Type of IOL | IOL | IOL | IOL | Cancel lens |
|---|---|---|---|---|
| Power (D) | 10.0 | 20.0 | 30.0 | Plano |
| Shape factor | −0.065776731574322 | −0.06399176033317 | −0.061301477522793 | N/A |
| Anterior radius (mm) | 30.0 | 15.0 | 10.0 | ∞ |
| Posterior radius (mm) | −34.2244761266865 | −17.0509999043154 | −11.3060951105157 | ∞ |
| Posterior aspheric 4-th | 0.3161412816537e−3 | 0.4765459705548e−3 | 0.7837959851963e−3 | 0 |
| Posterior aspheric 6-th | −1.976276618252e−6 | −4.225711852511e−6 | −8.598406735955e−6 | 0 |
| Center thickness (mm) | 0.50 | 0.75 | 1.00 | 0.50 |
| Edge thickness (mm) | 0.24205145789151 | 0.216469335330111 | 0.191332010695611 | 0.50 |

Example embodiments of modified vortex IOL designs can be implemented utilizing one or more procedures such as for example, as previously indicated, a cutting procedure (e.g., a lathe cutting procedure). Alternatively or additionally, a molding procedure (e.g., a cast molding procedure) can be utilized to fabricate example embodiments and implementations of modified vortex IOLs as described herein.

A modified vortex IOL (referred to herein as Vortex model 3 IOL) was cast molded with HOYA material A, and an aspheric applied as described below. The Vortex model 3 IOL was designed with 4.0 D power stretched (ΔP) based on an error function azimuthal power distribution with α=0.3 in a surface step reduction of 10°. See also FIGS. 43A and 43B (which respectively show the power map distribution and azimuthal plot for this model as well). For the aspheric portion of the design, the posterior apex radius is fixed and the conic constant and even asphere polynomial coefficients are optimized to meet the aberration requirement. The obtained design parameters for shape factor, anterior radius, posterior radius and its aspheric parameters, center thickness, and edge thickness are summarized in Table 5.

TABLE 5

Optical design parameters for Vortex Model 3 and PMMA cancellation lens.

| Type of IOL | Vortex Model 3 | Cancelation lens |
|---|---|---|
| Power (D) | 20.0 | Plano |
| Shape factor | −0.101319108450608 | N/A |
| Anterior radius (mm) | 18.8496943669637 | ∞ |
| Posterior radius (mm) | −23.10 | ∞ |
| Posterior conic constant | −48.40176251 | 0 |
| Posterior asphere 2-th | −5.357687804E−04 | 0 |
| Posterior asphere 4-th | 1.419461278E−03 | 0 |
| Posterior asphere 6-th | −9.406767891E−04 | 0 |

TABLE 5-continued

Optical design parameters for Vortex Model 3 and PMMA cancellation lens.

| Type of IOL | Vortex Model 3 | Cancelation lens |
|---|---|---|
| Posterior aspheric 8-th | 2.736344547E−04 | 0 |
| Posterior asphere 10-th | −4.050244753E−05 | 0 |
| Posterior asphere 12-th | 3.001723709E−06 | 0 |
| Posterior asphere 14-th | −8.838515192E−08 | 0 |
| Posterior asphere 16-th | 0 | 0 |
| Center thickness (mm) | 0.576075574040744 | 0.50 |
| Edge thickness (mm) | 0.17 | 0.50 |

In example embodiments and implementations, a technique (e.g., such as described herein) is utilized to overcome the rapidly changed surface step profile at the boundary between the angular sectors corresponding to the lowest dioptric power and the highest dioptric power.

The optics of the human eye in general is very complex optical system, and therefore, the visual outcome also depends on many parameters, such as the biometry (corneal shape, axial length, pupil size, etc.) as well as rods, cones and nerve layers in the retina, and the psychological process of visual information or visual perception.

In example embodiments and implementations, an IOL designed for (and that fulfills) a visual system utilizes or is modified using an arbitrary azimuthal power distribution, such as for example, a power distribution provided as a function of angle (azimuthal/angular) where the value at a given angle is any arbitrary value between a minimum power and a maximum power associated with that angle, that is, any value provided it meets the spread conditions. FIGS. 45-53 embody examples of arbitrary azimuthal power distributions.

In example embodiments and implementations, modifications based on a Vortex azimuthal power distribution design (e.g., such as described herein) can be made using arbitrary azimuthal power distribution.

Best results (thus far) in relation to the aforementioned modification(s) were observed for power distributions having 3 different power ranges to represent distance, intermediate, and near visual ranges, respectively. In at least some alternative implementations, the power ranges include (or consist of) 4 different power ranges. The energy of each power range and the intermediate and near powers can be set to fit the patient's needs.

Figure 45:
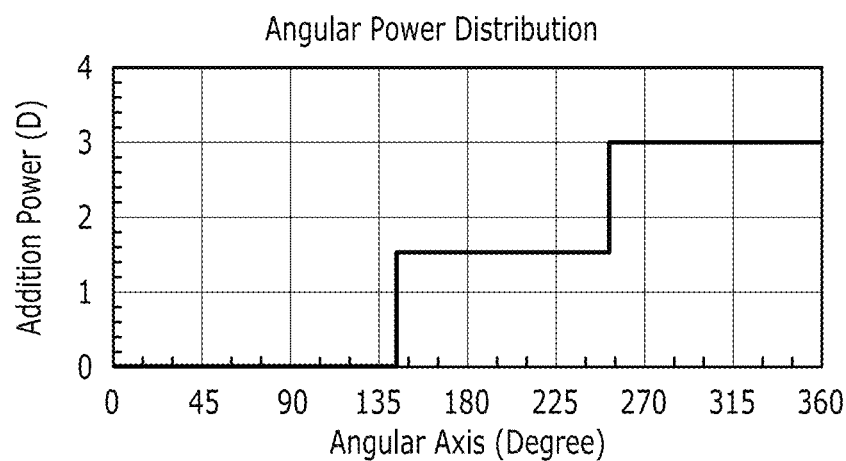
FIG. 45 shows an example angular power distribution of a Vortex azimuthal power distribution design with three different power ranges for distance, intermediate, and near (0.0 D, 1.5 D, and 3.0 D) with energy of 40%, 30%, and 30%, respectively.
Figure 46:
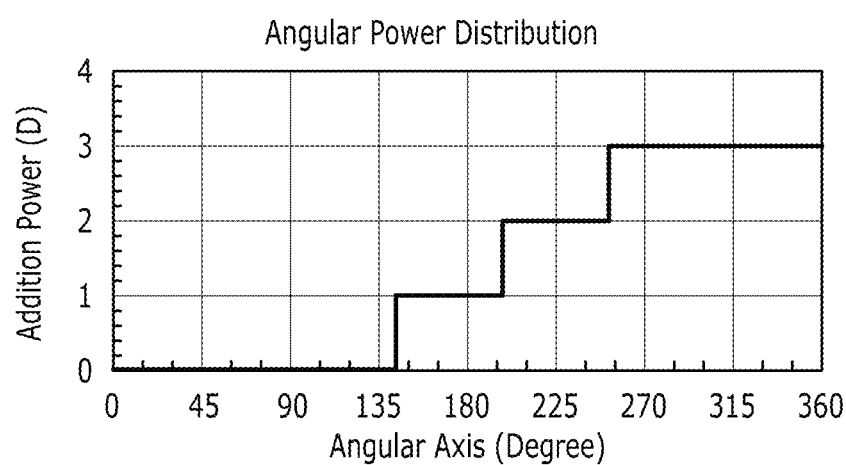
FIG. 46 shows an example angular power distribution of a Vortex azimuthal power distribution design with four different power ranges for distance, lower intermediate, higher intermediate, and near (0.0 D, 1.0 D, 2.0 D, and 3.0 D) with energy of 40%, 15%, 15%, and 30%, respectively.

FIG. 45 shows an example of such a design with 3 different power ranges for distance, intermediate, and near (0.0 D, 1.5 D, and 3.0 D) with energy of 40%, 30%, and 30%, respectively. FIG. 46 shows another example of such a design with 4 different power ranges for distance, lower intermediate, higher intermediate, and near (0.0 D, 1.0 D, 2.0 D, and 3.0 D) with energy of 40%, 15%, 15%, and 30%, respectively.

Figure 47:
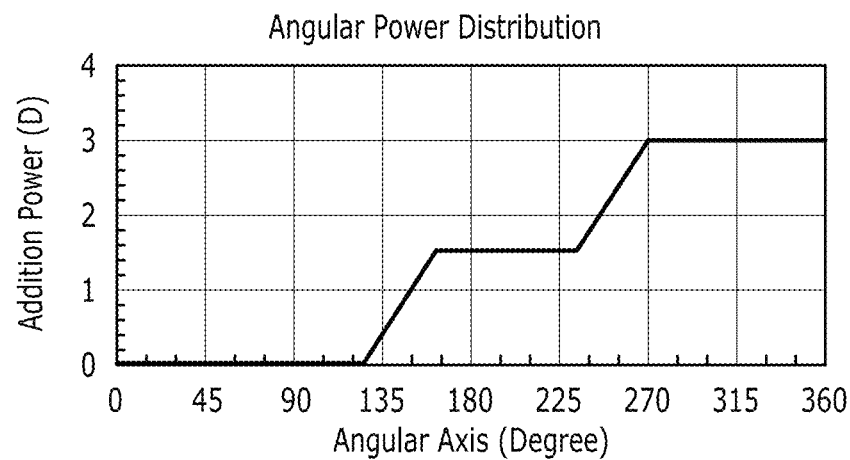
FIG. 47 shows the angular power distribution of FIG. 45 after applying to the Vortex design a linear azimuthal power distribution within specified azimuthal ranges.
Figure 48:
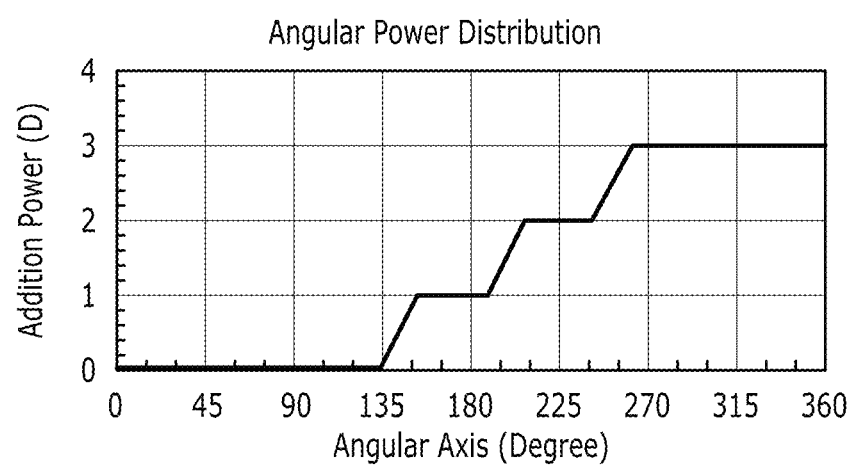
FIG. 48 shows the angular power distribution of FIG. 46 after applying to the Vortex design a linear azimuthal power distribution within specified azimuthal ranges.
Figure 49:
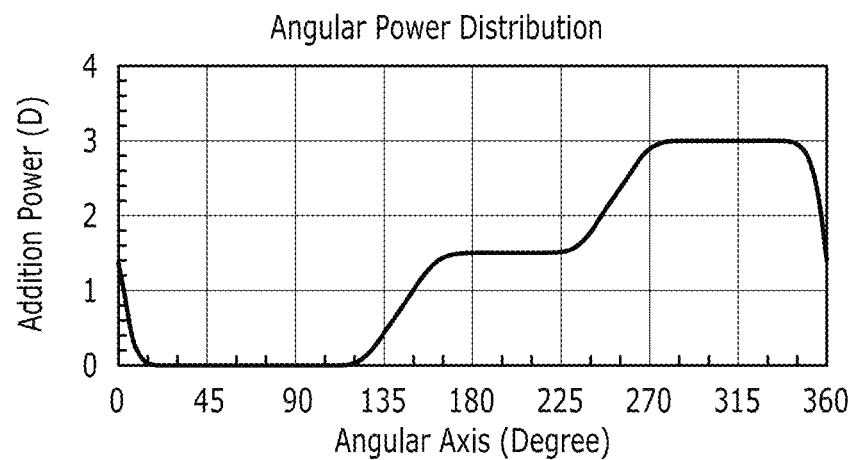
FIGS. 49 and 50 show the smoothed angular power distributions of FIGS. 47 and 48, respectively.
Figure 50:
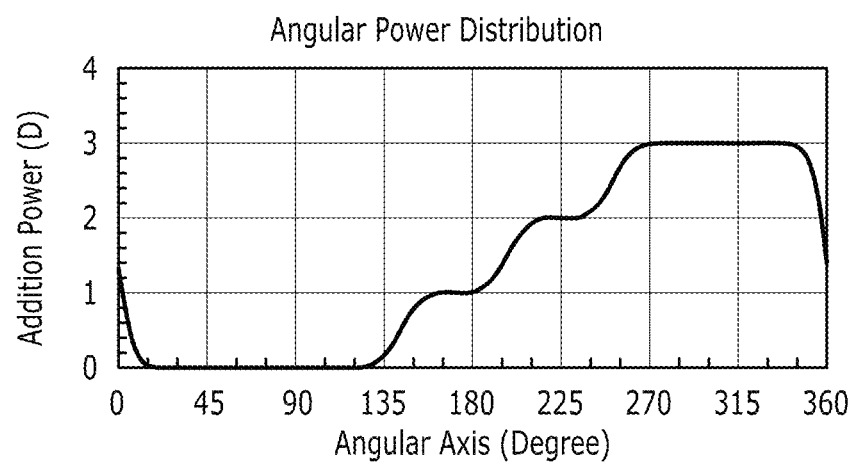

Applying the vortex design with linear azimuthal power distribution within specified azimuthal ranges to the angular power distributions of FIGS. 45 and 46 results in the angular power distributions of FIGS. 47 and 48, respectively. Discontinuities points (points at which there are, or at which discontinuities result) can be smoothed, for example, using a standard (conventional) Gaussian smoothing procedure. FIGS. 49 and 50 show the smoothed angular power distributions of FIGS. 47 and 48, respectively.

Figure 51:
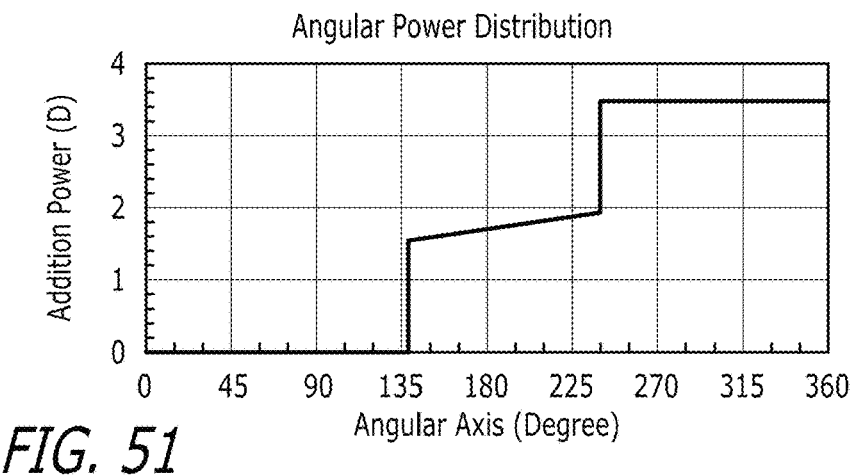
FIG. 51 shows an example angular power distribution of a Vortex azimuthal power distribution design with 3 different power ranges for distance, progressive intermediate, and near (0.0 D, 1.75 D, and 3.5 D) with energy of 38.33%, 28.22%, and 33.33%, respectively.
Figure 52:
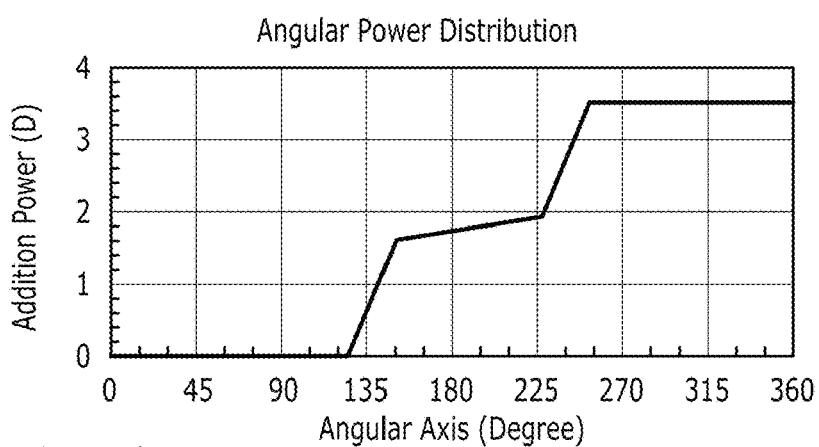
FIG. 52 shows the angular power distribution of FIG. 51 after applying to the Vortex design a linear azimuthal power distribution within specified azimuthal ranges.
Figure 53:
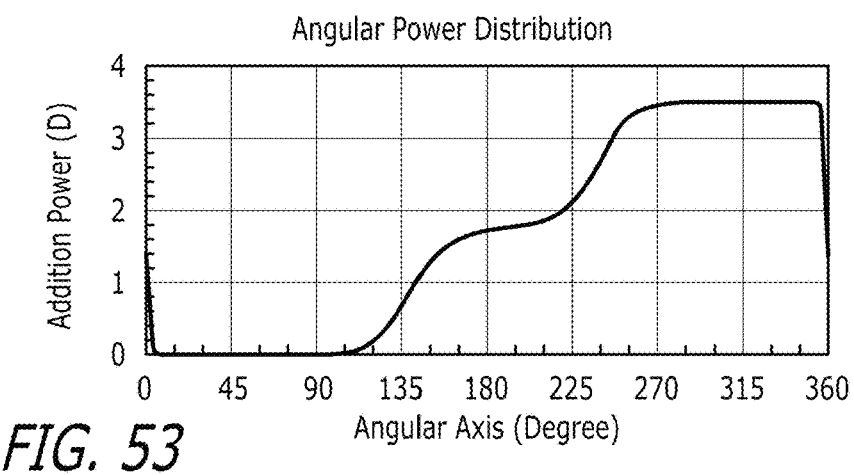
FIG. 53 shows the smoothed angular power distribution of FIG. 52.

In example embodiments and implementations in which a wider intermediate depth of focus is desired, a linear change in azimuthal power distribution for intermediate (the intermediate power range) can also be considered (utilized), and the linear change in azimuthal power distribution for intermediate will have a "progressive" property similar to those of the preceding examples. FIG. 51 shows an example of such a design with 3 different power ranges for distance, progressive intermediate, and near (0.0 D, 1.75 D, and 3.5 D) with energy of 38.33%, 28.22%, and 33.33%, respectively. Again, similar to the process utilized to obtain the angular power distributions of FIGS. 47 and 48, by applying the vortex design with linear azimuthal power distribution within specified azimuthal ranges then the angular power distribution of FIG. 51 becomes the angular power distribution of FIG. 52. FIG. 53 shows the smoothed angular power distribution of FIG. 52, and in this example, smoothing parameters of the change between distance power to intermediate and intermediate to near power are set to more smooth compared to the smoothing parameters of the change between the angle of 0 and 360 degrees.

By way of example, smoothing parameters can be selected or otherwise determined in relation to providing an azimuthal power distribution that satisfies one or more smoothness requirements or a power distribution having a particular profile or other characteristic(s) or that falls within a range of power distribution profiles or power distribution profile boundaries.

In example embodiments and implementations, smoothing (and/or other) parameters are selected/determined to provide additional smoothness to (or of) a power distribution, or to enhance or provide smoothness in one or more portions of a power distribution.

In example embodiments and implementations, smoothing (and/or other) parameters are selected/determined—e.g., set to "more smooth" (for example, an enhanced or additional amount/degree/extent of smoothness or smoothening applied)—in relation to parameters of or associated with a transition between the lowest dioptric power sector and the highest dioptric power sector such as in the examples depicted in FIGS. 45-53 the change in Addition Power at and adjacent to (transitioning through) the 0°/360° angle of the power distribution.

In example embodiments and implementations, smoothing (and/or other) parameters are selected/determined in relation to one or more smoothness or other power distribution requirements of an azimuthal power distribution, e.g., to provide additional smoothness to (or of) the azimuthal power distribution or to enhance or provide smoothness in one or more portions of the power distribution.

Smoothed angular power distributions (e.g., such as shown in FIGS. 49, 50 and 53) can be implemented/obtained utilizing a procedure such as Gaussian smoothing (for example, see U.S. Pat. No. 8,556,416, which is hereby incorporated by reference).

In example embodiments and implementations, vortex IOLs are composed of optical element(s) implementing amplitude apodization, that is, a modulation in light amplitude that changes the amplitude intensity from one portion of the lens to another (e.g., gradually decreasing from the center of the lens moving toward peripheral portion(s) of the lens). In optics, a modulation in light amplitude can be effected by a modulation in the light transmittance of a lens. An example design of amplitude apodization effects 100% transmittance (or close to 100% transmittance) at the center of the lens with transmittance gradually decreasing moving toward a peripheral location on the lens.

The effect of amplitude apodization is to enhance the contrast in lower frequencies, although as a consequence contrast in higher frequencies may be degraded. Fortunately, a human eye (dependent) ocular system is not capable (of facilitating vision) for higher frequencies. Amplitude apodization is generally in effect a form of pupil masking, and in some implementations significantly reduces the dependency of the optical (design) properties to the pupil size, for example, the degradation (of contrast) within bigger pupil size ocular systems can be much reduced.

Figure 41:
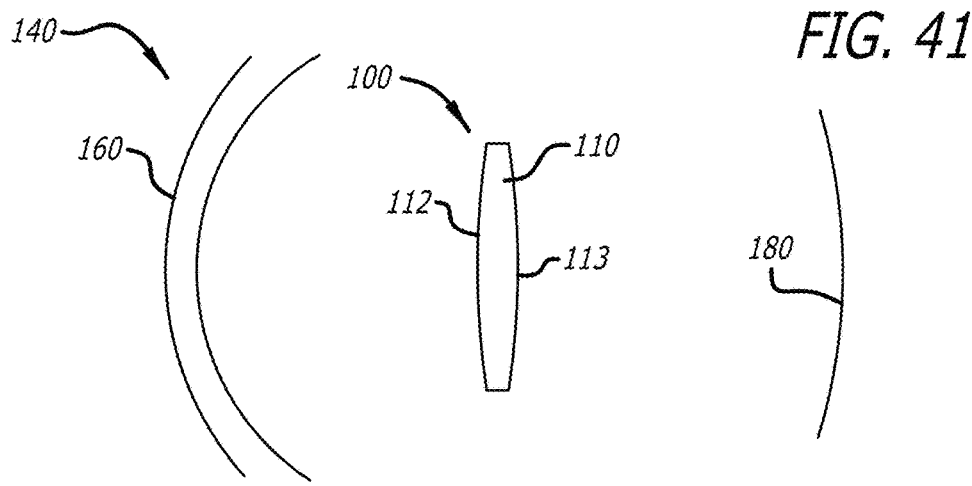
FIG. 41 is a schematic view of an optical system, including an IOL and an eye, in accordance with at least one embodiment of a present invention.
Figure 42:
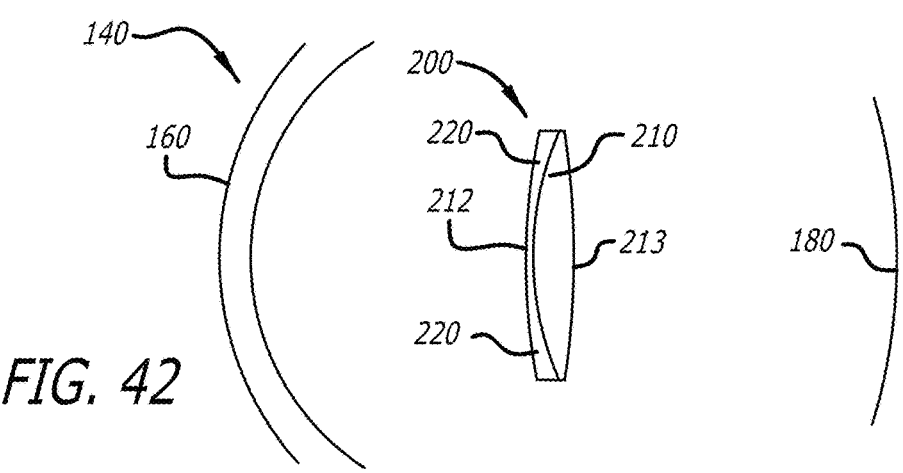
FIG. 42 is a schematic view of an optical system, including an IOL and an eye, in accordance with at least one embodiment of a present invention in which amplitude apodization is implemented.

A reduction in light transmittance can be effected by a lens or one or more portions thereof implemented such that transmissibility of the lens material varies (decreases) from the center to one or more edge, periphery or optical boundary (portion(s)) of said lens, the transmissibility varying for example according to a Gaussian (bell shape) function which will minimize the side lobe of the point spread function. Example embodiments and implementations involve providing, adapting and/or implementing the lens (or one or more portions thereof) such that transmissibility of the lens material is controlled from one portion of the lens to another (e.g., from the center to one or more edge, periphery or optical boundary (portion(s)) of said lens) to implement amplitude apodization. Amplitude apodization can be implemented in IOLs (e.g., such as the vortex IOLs described herein) as well as other optical devices. One such vortex IOL, which is identified by reference numeral 200 in FIG. 42, has a lens body 210 including an anterior lens surface (or portion) 212 and a posterior lens surface (or portion) 213 implemented as described herein (e.g. as with the IOL 100 and anterior and posterior surfaces 112, 113 thereof shown in FIG. 41). As with the IOL 100, the IOL 200 is shown as part of an optical system that also includes an eye 140 with a cornea 160 and retina 180. Haptics (not shown in this figure) may also be provided. The IOL 200 differs (from IOL 100) in that one or more portions, denoted by reference numeral 220, are provided, adapted, or implemented to implement (or effect implementation of a lens or other optics design inclusive of) amplitude apodization. In FIG. 42, the portion(s) 220 are shown as including (e.g., permeating into) part of the lens body 210. In example embodiments and implementations, the portion(s) 220 are inclusive of at least some optically relevant portion(s) of the IOL 200 (e.g., the anterior lens surface 212 and, in some implementations, lens material adjacent to the anterior lens surface and/or further within the lens body 210).

In example embodiments and implementations, the transmissibility of lens material (of or within the portion(s) 220) is controlled or effected via utilization of one or more substances, elements, components, or structures adapted to influence (attenuate) amplitude intensity to varying degrees from one portion of the lens to another. For example, the transmissibility of the lens material is controlled or effected via utilization of one or more dyes (e.g., selected taking into account biocompatibility of the dye(s) in relation to the ocular system or an element or portion thereof).

Figure 42A:
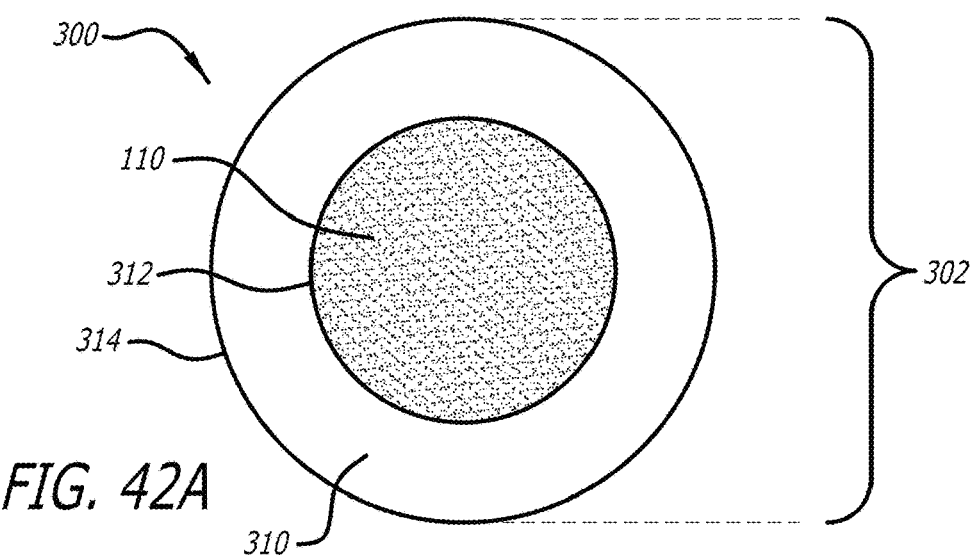
FIG. 42A is a plan view showing an example embodiment of an optical device, the optical device including a lens such as shown in FIG. 41 and a peripheral portion thereabout that is devoid, or substantially devoid, of azimuthal power distribution (non-azimuthal, e.g., monofocal), the peripheral portion being implemented to provide a refractive focus (e.g., corresponding to far or intermediate vision).

Example embodiments and implementations involve providing, adapting and/or implementing an optical device or optic (e.g., an IOL) that includes (e.g., at a central portion thereof) a lens composed of entirely refractive optical element(s) (e.g., implemented such as previously described), and a peripheral portion thereabout that is devoid (or substantially devoid) of azimuthal power distribution (non-azimuthal, e.g., monofocal). The peripheral portion is, for example, implemented to provide a refractive focus region (e.g., that provides or at least in part facilitates far or intermediate vision). One such optical device or optic, which is identified by reference numeral 300 in FIG. 42A, including a lens such as shown in FIG. 41 (denoted lens 110 in FIG. 42A) and a peripheral (lens) portion 310 thereabout, which together provide an active region 302 (of the optical device or optic). In example embodiments and implementations, the lens 110 and the lens portion 310 are implemented to provide central and peripheral portions (of the optical device or optic), respectively. In example embodiments and implementations, the lens portion 310 extends from an optical interface/transition 312 (e.g., at or adjacent to an outer periphery of the lens 110) to an outer periphery 314 (e.g., at or adjacent to an outer periphery of the optical device or optic 300). In example embodiments and implementations, the lens portion 310 is implemented to provide an outer optic region having one or more portions or sectors (e.g., only a single peripheral optic portion/sector, or multiple portions or sectors implemented such that at least one of the portions or sectors provides a different refractive focus than provided by another of the portions or sectors). As with the IOL 100, the optical device or optic 300 can be part of an optical system that also includes an eye 140 with a cornea 160 and retina 180. Haptics (not shown in this figure) may also be provided. In FIG. 42A, the active region 302 is shown as extending to the outer periphery 314 of the lens portion 310. In example embodiments and implementations, the active region 302 is otherwise provided, e.g., an outer boundary (of the active region 302) being provided at least in part at one or more portions (of the optical device or optic) located radially inward in relation to the outer periphery 314.

Thus, in example embodiments and implementations, an optical device includes an intraocular lens (IOL) comprising (or consisting of) entirely refractive optical element(s) implementing an angular modulation of a transmittance of said lens. In example embodiments and implementations, an optical device includes an intraocular lens (IOL) comprising (or consisting of) an entirely refractive (multifocal) optical element with spiral or helical structure implemented to control the refractive foci of incident light. In example embodiments and implementations, an optical device includes an intraocular lens (IOL) comprising (or consisting of) an entirely refractive multifocal optical element (e.g., with spiral or helical structure) implemented to control the refractive foci of incident light.

In example embodiments and implementations, an optical device includes an intraocular lens (IOL) implementing a modified vortex design such as described herein, and the lens provides total visual depth of focus (DOF) for the optical device of about 2.0 D to 3.0 D (e.g., DOF being the dioptric range for which the visual Strehl ratio of the optical device is greater than 0.12 at 3 mm pupil size diameter). In at least some alternative implementations, the optical device may be about 1.0 D to 3.0 D, about 1.0 D to 2.0 D, or about 0.5 D to 1.0 D.

In example embodiments and implementations, an optical device includes an intraocular lens (IOL) implementing a modified vortex design such as described herein, and the lens provides a (relatively less wide) total visual depth of focus (DOF) for the optical device of about 1.0 D to 2.0 D (e.g., DOF being the dioptric range for which the visual Strehl ratio of the optical device is greater than 0.12 at 3 mm pupil size diameter). With visual DOF about 1.0 D to 2.0 D, an eye is enabled to see distance to intermediate objects, which are distances suitable for daily life but not proper for reading, a potentially desirable vision enhancement for a person who does not read much in his/her daily life.

In example embodiments and implementations, an optical device includes an intraocular lens (IOL) implementing a modified vortex design such as described herein, and the lens provides a total visual depth of focus (DOF) for the optical device of about 0.5 D to 1.0 D (e.g., DOF being the dioptric range for which the visual Strehl ratio of the optical device is greater than 0.12 at 3 mm pupil size diameter). With visual DOF about 0.5 D to 1.0 D, an eye is enabled to see distance (e.g., enabled to see distance only, as in a monofocal) with DOF enhanced to be slightly wider to correct the refractive error due to IOL power calculation deviation. Such an enhancement provides the IOL with tolerance to (in effect) absorb error (e.g., refractive error) after implantation.

Current IOL power calculation such as traditional SRK II, SRK/T or more modern formula such as Holladay 1, Hoffer Q, Haigis, or even formula using ray trace method still remaining about +/−1.0 D. If the lens is designed with visual DOF of 0.5 D to 1.0 D, then the spherical error risk due to IOL power calculation can be suppressed, and therefore will increased the patient's satisfaction as the dependency on distance correcting spectacles is decreased.

In example embodiments and implementations, an optical device includes an intraocular lens (IOL) implementing a modified vortex design such as described herein, and the lens includes one or more surfaces implementing an azimuthal power distribution. The azimuthal power distribution can be linear or nonlinear. For example, the azimuthal power distribution corresponds to a nonlinear dioptric power distribution determined based on a sinusoidal function or an error function. Also, and as previously discussed, modifications using (or implementing) an arbitrary azimuthal power distribution can also be provided, for example, over 3 or 4 power ranges (see e.g., FIGS. 45-53).

In example embodiments and implementations of modified vortex IOL designs, the azimuthal power distribution is implemented for $0 \leq \theta < 2\pi - \alpha$, where $\alpha$ is one or more of: a nonzero angle, no less than a minimum angle, no greater than a maximum angle, and within a range of angles (for example, $10° \leq \alpha \leq 30°$).

In example embodiments and implementations of modified vortex IOL designs, the azimuthal power distribution is implemented for $0 \leq \theta < 2\pi - \alpha$, where $\alpha$ is an angle, and a distribution that is complementary to (e.g., similar to/approximately the opposite of) the azimuthal power distribution is implemented for $2\pi - \alpha \leq \theta < 2\pi$, which is stretching from high to low dioptric power.

In example embodiments and implementations of modified vortex IOL designs, the azimuthal power distribution is implemented (e.g., based on an error function with $\sigma = 0.2$ or 0.3) in an angular dioptic power zone ranging from a lowest dioptric power sector to a highest dioptic power sector, the lens including a surface step reduction (e.g., of 10°) between the lowest dioptric power sector and the highest dioptric power sector (of the azimuthal power distribution).

In example embodiments and implementations, the azimuthal power distribution principally (or predominantly) implements one or more of, for example: a distance (lower diopter) vision zone, an intermediate (medium power) vision zone, and a near (higher diopter) vision zone—for example, an azimuthal power distribution that principally (or predominantly) implements a distance vision zone and an intermediate vision zone (e.g., to provide DOF ranges from 1.0 D to 2.0 D). In example embodiments and implementations, the azimuthal power distribution principally implements a distance (lower diopter) vision zone and a near (higher diopter) vision zone. Alternatively, the azimuthal power distribution principally implements an intermediate (medium power) vision zone. Alternatively, the azimuthal power distribution principally implements a distance vision zone extending visual depth of focus, e.g., with DOF <1.0 D (wider visual DOF).

In example embodiments and implementations, the azimuthal power distribution changes (e.g., raises) slower in one or more of a low power portion, a medium power portion, and a high power portions thereof as compared to an adjacent portion of (along) the azimuthal power distribution. In example embodiments and implementations, the azimuthal power distribution changes (e.g., raises) slower in low and high power portions thereof as compared to a (medium power) portion of the azimuthal power distribution between the low and high power portions. In example embodiments and implementations, the azimuthal power distribution changes (e.g., raises) slower in a generally centrally located (medium power) portion thereof as compared to one or more adjacent portions of said lens along the azimuthal power distribution.

In example embodiments and implementations, the lens includes angular sectors and one or more surfaces implementing a spherical design (portion of said lens) for each (infinitesimal) angular sector of said lens (along the azimuthal power distribution) (e.g., such that each infinitesimal angular sector corresponds to a spherical lens with a focal length of f+Δf θ/(2π)). In example embodiments and implementations, the lens includes angular sectors and one or more surfaces implementing an aspheric design (portion of said lens) for each (infinitesimal) angular sector of said lens (along the azimuthal power distribution).

In example embodiments and implementations, the lens includes one or more surfaces implementing spherical aberration control (e.g., to compensate for corneal spherical aberration) (e.g., by effecting one or more radial power distributions). In example embodiments and implementations, the lens includes one or more surfaces implementing astigmatism control. In example embodiments and implementations, the lens includes one or more surfaces implementing (both) spherical aberration control and astigmatism control.

In example embodiments and implementations, an optical device includes an intraocular lens (IOL) comprising (or consisting of) entirely refractive optical element(s) (e.g., an entirely refractive optical element with spiral or helical structure) (e.g., an entirely refractive multifocal optical element) implementing amplitude apodization that changes the amplitude intensity (e.g., imposes amplitude intensity profile(s)) from the center to one or more edge, periphery or optical boundary (portion(s)) of the lens. For example, the amplitude apodization is implemented by transmissibility of the lens material (e.g., transmissibility that changes from the center to one or more edge, periphery or optical boundary of the lens), the transmissibility being controlled or effected via one or more substances, elements, components, or structures of or within the lens (e.g., inclusive of one or more dyes) adapted to influence (attenuate) amplitude intensity to varying degrees from one portion of the lens to another. In example embodiments and implementations, the transmissibility of the lens material is controlled or effected via utilization of one or more dyes (e.g., selected taking into account biocompatibility of the dye(s) in relation to the ocular system or an element or portion thereof).

In example embodiments and implementations, an optical device includes an intraocular lens (IOL) comprising an intraocular lens (IOL) having entirely refractive optical element(s) including one or more surfaces implementing an azimuthal power distribution, and a peripheral optic (or lens) portion that is devoid (or substantially devoid) of azimuthal power distribution. The peripheral optic (or lens) is implemented, for example, to provide a refractive focus corresponding to far or intermediate vision.

Thus, in example embodiments and implementations, a process for manufacturing an optical device includes the step(s) of: molding and/or cutting a material to form an intraocular lens (IOL) implementing an angular modulation of a transmittance of said lens, the lens including one or more surfaces implementing an azimuthal power distribution, and entirely (or substantially) eliminating any discontinuity (e.g., at zero degree) along said azimuthal power distribution. In example embodiments and implementations, the lens is molded and/or cut to provide entirely refractive optical element(s) implementing the angular modulation (of a transmittance of said lens). In example embodiments and implementations, the lens is molded and/or cut to provide an entirely refractive (e.g., multifocal) optical element with spiral or helical structure implementing the angular modulation (of a transmittance of said lens). In example embodiments and implementations, the lens is molded and/or cut to provide an entirely refractive multifocal optical element (e.g., with spiral or helical structure) implementing the angular modulation (of a transmittance of said lens).

In example embodiments and implementations of a process for manufacturing an optical device, the step(s) of molding and/cutting include utilizing a cast molding procedure and/or a lathe cut procedure (e.g., to provide the profile of at least a portion of the lens). In example embodiments and implementations, the step(s) of molding and/cutting include utilizing a control scheme (e.g., erfc function) to effect a smoothing (step reduction) of the material (e.g., to provide at least a portion of the azimuthal power distribution).

In example embodiments and implementations, the process for manufacturing an optical device further includes providing, adapting and/or implementing the lens such that transmissibility of the lens material varies at different portion(s) of the lens. By way of example, the lens is provided, adapted and/or implemented such that transmissibility of the lens material varies (decreases) from the center to one or more edge, periphery or optical boundary (portion(s)) of the lens, thereby effecting (implementing) amplitude apodization such as described herein.

In example embodiments and implementations, the process for manufacturing an optical device further includes providing, adapting and/or implementing the lens such that transmissibility of the lens material is controlled to implement amplitude apodization that changes the amplitude intensity (e.g., imposes amplitude intensity profile(s)) from the center to one or more edge, periphery or optical boundary (portion(s) of the lens. By way of example, the transmissibility is controlled or effected via utilization of one or more substances, elements, components, or structures adapted to influence (attenuate) amplitude intensity to varying degrees from one portion of the lens to another. In example embodiments and implementations, the transmissibility of the lens material is controlled or effected via utilization of one or more dyes (e.g., selected taking into account biocompatibility of the dye(s) in relation to the ocular system or an element or portion thereof).

Although the present invention(s) has(have) been described in terms of the example embodiments above, numerous modifications and/or additions to the above-described embodiments would be readily apparent to one skilled in the art. It is intended that the scope of the present invention(s) extend to all such modifications and/or additions.

What is claimed is:

1. An optical device comprising:
    an intraocular lens (IOL) composed entirely of a refractive multifocal optical element implementing an angular modulation of a transmittance of said lens and defining a center and an optical boundary;
    wherein the lens includes one or more surfaces implementing a power that varies in the azimuthal direction, thereby defining an azimuthal power distribution, and that does not vary in the radial direction from the center to the optical boundary, and
    wherein the refractive multifocal optical element includes spiral or helical structure implemented to control the refractive foci of incident light.

2. The optical device of claim 1, wherein the lens provides total visual depth of focus (DOF) for the optical device of about 2.0 D to 3.0 D.

3. The optical device of claim 1, wherein the lens provides total visual depth of focus (DOF) for the optical device of about 1.0 D to 2.0 D.

4. The optical device of claim 1, wherein the lens provides total visual depth of focus (DOF) for the optical device of about 0.5 D to 1.0 D.

5. The optical device of claim 1, wherein the azimuthal power distribution is linear.

6. The optical device of claim 1, wherein the azimuthal power distribution is nonlinear.

7. The optical device of claim 6, wherein the azimuthal power distribution corresponds to a nonlinear dioptric power distribution determined based on a sinusoidal function.

8. The optical device of claim 6, wherein the azimuthal power distribution corresponds to a nonlinear dioptric power distribution determined based on an error function.

9. The optical device of claim 1, wherein the azimuthal power distribution is implemented in an angular dioptic power zone ranging from a lowest dioptic power sector to a highest dioptic power sector, the lens including a surface step reduction between the lowest dioptric power sector and the highest dioptric power sector.

10. The optical device of claim 1, wherein the azimuthal power distribution provides more power in one or more of a distance vision zone, an intermediate vision zone, and a near vision zone.

11. The optical device of claim 1, wherein the azimuthal power distribution provides more power in one of a distance vision zone and an intermediate vision zone.

12. The optical device of claim 1, wherein the azimuthal power distribution provides more power in an intermediate vision zone.

13. The optical device of claim 1, wherein the azimuthal power distribution provides less power in a distance vision zone extending visual depth of focus.

14. The optical device of claim 1, wherein the azimuthal power distribution changes slower in one or more of a low power portion, a medium power portion, and a high power portions thereof as compared to an adjacent portion of the azimuthal power distribution.

15. The optical device of claim 1, wherein the azimuthal power distribution changes slower in low and high power portions thereof as compared to a portion of the azimuthal power distribution between said low and high power portions.

16. The optical device of claim 1, wherein the azimuthal power distribution changes slower in a portion of the lens along the azimuthal power distribution as compared to one or more adjacent portions of the lens.

17. The optical device of claim 1, wherein the lens is an extended depth of focus lens.

18. The optical device of claim 1, wherein the azimuthal power distribution provides more power in high and low intermediate vision zones.

* * * * *